US009017938B2

(12) United States Patent
Zollo

(10) Patent No.: US 9,017,938 B2
(45) Date of Patent: Apr. 28, 2015

(54) USE OF MICRORNA-199B-5P IN MEDICAL AND DIAGNOSTIC FIELD

(75) Inventor: Massimo Zollo, Naples (IT)

(73) Assignee: Advanced Accelerator Applications, Saint-Genis Pouilly (FR)

( * ) Notice: Subject to any disclaimer, the term of this patent is extended or adjusted under 35 U.S.C. 154(b) by 173 days.

(21) Appl. No.: 13/260,214

(22) PCT Filed: Mar. 23, 2010

(86) PCT No.: PCT/IT2010/000125
§ 371 (c)(1),
(2), (4) Date: Dec. 16, 2011

(87) PCT Pub. No.: WO2010/009511
PCT Pub. Date: Sep. 30, 2010

(65) Prior Publication Data
US 2012/0108656 A1 May 3, 2012

(30) Foreign Application Priority Data
Mar. 24, 2009 (IT) .............................. RM2009A0136

(51) Int. Cl.
C12Q 1/68 (2006.01)
C12N 15/113 (2010.01)

(52) U.S. Cl.
CPC ........ C12N 15/113 (2013.01); C12N 2310/141 (2013.01)

(58) Field of Classification Search
None
See application file for complete search history.

(56) References Cited

U.S. PATENT DOCUMENTS

2006/0105360 A1* 5/2006 Croce et al. .................... 435/6

FOREIGN PATENT DOCUMENTS

| CN | 1768139 | 9/2004 |
| JP | 2007532130 | 11/2007 |
| WO | 2004/076622 | 9/2004 |
| WO | 2007/081720 | 7/2007 |
| WO | 2008/015028 | 2/2008 |
| WO | 2008/094545 | 8/2008 |
| WO | 2005/099770 | 10/2008 |

OTHER PUBLICATIONS

Chinese Office Action mailed on Dec. 17, 2012 for Application 201080023615.6 filed on Mar. 23, 2010 in the name of Advanced Accelerator Applications—English Translation.
Albano Francesco et al.: "MicroRNAs as the target of deletions on der(9) in chronic myeloid leukemia" Blood, vol. 110, No. 11, Part 1, Nov. 2007, p. 860A, XP002554497.
Albano Francesco et al.: "Chronic Myeloid Leukemia with deletions on Der(9) shows Mir-199b downregulated dxpression", Blood, vol. 112, No. 11, Nov. 2008, p. 396, XP002554498.
Pizzimenti Stefania et al: "MicroRNA expression changes during human leukemic HL-60 cell differentiation induced by 4-hydroxynonenal, a product of lipid peroxidation", Free Radical Biology & Medicine, vol. 46, No. 2, Jan. 2009, pp. 282-288, XP002554499.
Pizzimenti Stefania et al: "Supplementary data S1 and Supplementary data S2" Free Radical Biology & Medicine, [Online] Jan. 2009, XP002554500.
Chaubey A. et al.: "MicroRNAs and deletion of the derivative chromosome 9 in chronic myeloid leukemia" Leukemia: Official Journal of the Leukemia Society of America, vol. 23, No. 1, Jan. 2009, pp. 186-188, XP002554503.
Garzia Livia et al: "MicroRNA-199b-5p Impairs Cancer Stem Cells through Negative Regulation of HES1 in Medulloblastoma", PLOS One, vol. 4, No. 3, Mar. 24, 2009, XP002591555.
Buhren J, et al. "Expression of the neurotrophin receptor p75NTR in medulloblastomas is correlated with distinct histological and clinical features: evidence for a medulloblastoma subtype derived from the external granule cell layer." J Neuropathol Exp Neurol 59: 229-240 (2000).
Katsetos CD, et al. "A cytomorphological scheme of differentiating neuronal phenotypes in cerebellar medulloblastomas based on immunolocalization of class III beta-tubulin isotype (beta III) and proliferating cell nuclear antigen" (PCNA)/cyclin. Clin Neuropathol14: 72-81. (1995).
Yang SY, et al." Radiation-induced cerebellar glioblastoma at the site of a treated medulloblastoma: case report." J Neurosurg 102: 417-422. (2005).
Patrice SJ, et al. "Results of radiosurgery in the management of recurrent and residual medulloblastoma." Pediatr Neurosurg 22: 197-203. (1995).
Huntly BJ, "Summing up cancer stem cells." Nature 435: 1169-1170. (2005).
Eberhart CG "In search of the medulloblast: neural stem cells and embryonal brain tumors." Neurosurg Clin N Am 18: 59-69, (2007).
Fan X, et al. "Medulloblastoma stem cells." J Clin Oncol 5 26: 2821-2827. (2008).
Friedman HS, et al. Establishment and characterization of the human medulloblastoma cell line and transplantable xenograft 0283 Med. J Neuropathol Exp Neurol 44: 592-605. (1985).
Jacobsen PF et al. "Establishment of a human medulloblastoma cell line and its heterotransplantation into nude mice." J Neuropathol Exp Neuro144: 472-485. (1985).
Bartel D.P., MicroRNAs: genomics, biogenesis, mechanism, and function. Cell (2004), 116: pp. 281-297.
Hammond, S.M. MicroRNAs as oncogenes. Curr Opin Genet Dev (2006), 16: 4-9.
O'Donnell K.A. et al. c-Myc-regulated microRNAs modulate E2F1 expression, Nature (2005), 435: pp. 839-843.
Calin, G.A. et al. Frequent deletions and down-regulation of microRNA genes miR15 and miR16 at 13q14 in chronic lymphocytic leukemia, Proc. Natl. Acad. Sci. U.S.A. (2002) 99: pp. 15524-15529.
Ciafre, S.A. et al. Extensive modulation of a set of microRNAs in primary glioblastoma, Biochem Biophys Res. Commun (2005) 334: pp. 1351-1358.

(Continued)

Primary Examiner — Stephanie K Mummert
Assistant Examiner — Aaron Priest
(74) Attorney, Agent, or Firm — Steinfl & Bruno LLP

(57) ABSTRACT

This invention concerns the use of MicroRNA-199b-5p in medical and diagnostic fields. Particularly, this invention concerns the use of the miR199b-5p in the anti-cancer therapy and as a histophatological and metastasis marker.

11 Claims, 23 Drawing Sheets

(56) References Cited

OTHER PUBLICATIONS

Michael, M.Z. et al, Reduced accumulation of specific microRNAs in colorectal neoplasia, *Mol. Cancer Res.* (2003) 1: pp. 882-891.
Fabbri, M. et al. MicroRNA-29 family reverts aberrant methylation in lung cancer by targeting DNA methyltransferases 3A and 3B, *Proc. Natl. Acad. Sci. U.S.A.* (2007) 104: 15805-15810.
Ma, L. et al. Tumour invasion and metastasis initiated by microRNA-10b in breast cancer. *Nature* (2007) 449: pp. 682-688.
Gilbertson, R.J. et al. The origins of medulloblastoma subtypes, *Annu. Rev. Pathol.* (2008) 3: pp. 341-365.
Marino S. Medulloblastoma: developmental mechanisms out of control, *Trend Mol. Med.* (2005) 11: pp. 17-22.
MacDonald, T.J. Aggressive infantile embryonal tumors, *J. Child Neurol.* (2008) 23: pp. 1195-1204.
Kombogiorgas, D. et al. Outcome of children with posterior fossa medulloblastoma: a single institution experience over the decade 1994-2003, Childs. Nerv. Syst. (2007) 23: pp. 399-405.
Singh, S.K. et al. Cancer stem cells in nervous system tumors, *Oncogene* (2004) 23: pp. 7267-7273.
Yang, Z.J. et al. Medulloblastoma can be initiated by deletion of Patched in lineage-restricted progenitors or stem cells, *Cancer Cell* (2008) 14: pp. 135-145.
Solecki, D.J. et al. Activated Notch2 signaling inhibits differentiation of cerebellar granule neuron precursors by maintaining proliferation, *Neuron* (2001) 31: pp. 557-568.
Ishibashi M. et al. Persistent expression of helix-loop-helix factor HES-1 prevents mammalian neural differentiation in the central nervous system, *Embo. J.* (1994) 13: pp. 1799-1805.
Ishibashi, M. et al. Targeted disruption of mammalian hairy and Enhancer of split homolog-1 (HES-1) leads to up-regulation of neural helix-loop-helix factors, premature neurogenesis, and severe neural tube defects, *Genes Dev.* (1995) 9: pp. 3136-3148.
Nakamura, Y. et al. The bHLH gene hes1 as a repressor of the neuronal commitment of CNS stem cells, *J. Neurosci.* (2000) 20: pp. 283-293.
Fan, X. et al. Notch1 and notch2 have opposite effects on embryonal brain tumor growth, *Cancer Res.* (2004) 64: pp. 7787-7793.
Hallahan, A.R. et al. The SmoA1 mouse model reveals that notch signaling is critical for the growth and survival of sonic hedgehog-induced medulloblastomas, *Cancer Res.* (2004) 64: pp. 7794-7800.
Leung, C. et al. Bmi1 is essential for cerebellar development and is overexpressed in human medulloblastomas, *Nature* (2004) 428: pp. 337-341.
Griffiths-Jones S. The microRNA Registry, *Nucleic Acids Res.* (2004) 32: pp. D109-D111.
Yanaihara, N. et al. Unique microRNA molecular profiles in lung cancer diagnosis and prognosis, *Cancer Cell* (2006) 9: pp. 189-198.
Sandberg, A.A. Cytogenetics and molecular genetics of bladder cancer: a personal view, *Am. J. Med. Genet* (2002) 115: pp. 173-182.
Gramantieri, L. et al. Cyclin G1 is a target of miR-122a, a microRNA frequently down-regulated in human hepatocellular carcinoma, *Cancer Res.* (2007) 67: pp. 6092-6099.
Jiang, J. et al. Association of MicroRNA expression in hepatocellular carcinomas with hepatitis infection, cirrhosis, and patient survival, *Clin. Cancer Res.* (2008) 14: pp. 419-427.
Murakami, Y. et al. Comprehensive analysis of microRNA expression patterns in hepatocellular carcinoma and non-tumorous tissues, *Oncogene* (2006) 25: pp. 2537-2545.
Izant, J.G. et al. Microtubule-associated proteins: a monoclonal antibody to MAP2 binds to differentiated neurons, *Proc. Natl. Acad. Sci. U.S.A.* (1980) 77: pp. 4741-4745.
Li, X.N. et al. Phenylbutyrate and phenylacetate induce differentiation and inhibit proliferation of human medulloblastoma cells, *Clin. Cancer Res.* (2004) 10: pp. 1150-1159.
Hatakeyama, J. et al. Has genes regulate size, shape and hitogenesis of the nervous system by control of the timing of neural stem cell differentiation, *Development* (2004) 131: pp. 5539-5550.

Fan, X. et al. Notch pathway inhibition depletes stem-like cells and blocks engraftment in embryonal brain tumors, *Cancer Res.* (2006) 66: pp. 7445-7452.
Kondo, T. et al. Persistence of a small subpopulation of cancer stem-like cells in the C6 glioma cell line, *Proc. Natl. Acad. Sci. U.S.A.* (2004) 101: pp. 781-786.
Goodell, M.A. et al. Isolation and functional properties of murine hematopoietic stem cells that are replicating in vivo, *J. Exp. Med.* (1996) 183: pp. 1797-1806.
Singh, S.K. et al. Identification of human brain tumour initiating cells, *Nature* (2004) 432: pp. 396-401.
Kertesz, M. et al. The role of site accessibility in microRNA target recognition, *Nat. Genet.* (2007) 39: pp. 1278-1284.
Kim, S. et al. MicroRNA miR199a regulates the MET proto-oncogene and the downstream extracellular signal-regulated kinase 2 (ERK2), *J. Biol. Chem.* (2008) 283: pp. 18158-18166.
Pogoriler, J. et al. Loss of cyclin D1 impairs cerebellar development and suppresses medulloblastoma formation, *Development* (2006) 133: pp. 3929-3937.
Gilbertson, R.J. et al. PDGFRB is overexpressed in metastatic medulloblastoma, *Nat. Genet.*, 2003, 35: pp. 197-198.
MacDonald, T.J. et al. Expression profiling of medulloblastoma: PDGFRA and the RAS/MAPK pathway as therapeutic targets for metastatic disease, *Nat. Genet.* (2001) 29: pp. 143-152.
Hatton, B.A. et al. The Smo/Smo model: hedgehog-induced medulloblastoma with 90% incidence and leptomeningeal spread, *Cancer Res.* (2008) 68: pp. 1768-1776.
Bao, S. et al. Glioma stem cells promote radioresistance by preferential activation of the DNA damage response, *Nature* (2006) 444: pp. 756-760.
Blazek, E.R. et al. Daoy medulloblastoma cells that express CD133 are radioresistant relative to CD133-cells, and the CD133+ sector is enlarged by hypoxia, *Int. J. Radiat Oncol. Biol. Phys.* (2007) 67: pp. 1-5.
Ben-Porath, I. et al. An embryonic stem cell-like gene expression signature in poorly differentiated aggressive human tumors, *Nat. Genet.* (2008) 40: pp. 499-507.
Gao, J.X. Cancer stem cells: the lessons from pre-cancerous stem cells, *J. Cell Mol. Med.* (2008) 12: pp. 67-96.
Grill, J. et al. High-dose chemotherapy in children with newly-diagnosed medulloblastoma, *Lancet. Oncol.* (2006) 7: pp. 787-789.
Grill, J. et al. treatment of medulloblastoma with postoperative chemotherapy along: an SFOP prospective trial in young children, *Lancet. Oncol.* (2005) 6: pp. 573-580.
Zimmermann, T.S. RNAi-mediated gene silencing in non-human primates, *Nature* (2006) 441: pp. 111-114.
Rubin, J.B. et al. A small-molecule antagonist of CXCR4 inhibits intracranial growth of primary brain tumors, *Proc. Natl. Acad. Sci. U.S.A.* (2003) 100: pp. 13513-13518.
Dovey, H.F. et al. Functional gamma-secretase inhibitors reduce beta-amyloid peptide levels in brain, *J. Neurochem.* (2001) 76: pp. 173-181.
Geling, A. et al. A gamma-secretase inhibitor blocks Notch signaling in vivo and causes a severe neurogenic phenotype in zebrafish, *EMBO Rep.* (2002) 3: pp. 688-694.
Ferretti, E. et al. MicroRNA profiling in human medulloblastoma, *Int. J. Cancer* (2008) 124: pp. 568-577.
Gilbertson, R.J. et al. Prognostic significance of the c-erbB-2 oncogene product in childhood medulloblastoma, *Br. J. Cancer* (1995) 71: pp. 473-477.
Giangaspero, F. et al. Stratification of medulloblastoma on the basis of histopathological grading, *Acta Neuropathot* (2006) 112: pp. 5-12.
Yang, S.-Y. et al., Radiation-induced cerebellar glioblastoma at the site of a treated medulloblastoma, *J. Neurosurg.* (Pediatrics 4), 2005, vol. 102, pp. 417-422.
PCT International Search Report for PCT/IT2010/000125 filed on Mar. 23, 2010 in the name of Massimo Zollo, mail date: Sep. 30, 2010.
PCT Written Opinion for PCT/IT2010/000125 filed on Mar. 23, 2010 in the name of Massimo Zollo, mail date: Sep. 24, 2011.
Albano, F. et al., Mirn199B downregulation in chronic myeloid leukaemia is associated with deletions on der(9), *British Journal of Haematology*, Jan. 2009, vol. 144, No. 2, pp. 271-273.

(56) References Cited

OTHER PUBLICATIONS

Kalscheuer, S. et al., Differential expression of microRNAs in early-stage neoplastic transformation in the lungs of F344 rats chronically treated with the tobacco carcinogen 4-(methylnitrosamino)-1-(3-pyridyl)-1-butanone, *Carcinogenesis*, Dec. 2008, vol. 29, No. 12, pp. 2394-2399.

Kalscheuer, S. et al., Supplementary data: Differential expression of microRNAs in early stage neoplastic transformation in the lungs of F344 rats chronically treated with the tobacco carcinogen 4-(methylnitrosamino)-1-(3-pyridy1)-1-buta none, *Carcinogenesis*, Dec. 2008.

Volinia, S. et al., A microRNA expression signature of human solid tumors defines cancer gene targets, *Proceedings of the National Academy of Sciences of the United States of America*, Feb. 14, 2006, vol. 103, No. 7, pp. 2257-2261.

Volinia, S. et al., Supporting information: A microRNA expression signature of human solid tumors defines cancer gene targets, *Proceedings of the National Academy of Sciences of the United States of America*, Feb. 14, 2006, pp. 1-23.

Garzia, L. et al., MicroRNA-199b-5p Imparis Cancer Stem Cells through Negative Regulation of HES1 in Medulloblastoma, *PLOS One*, Mar. 24, 2009, vol. 4, No. 3.

Zolfo, M. et al. The miR-199b-5p oncosuppressor targets HES1 in medulloblastoma, *Clinical & Experimental Metastasis*, Oct. 2009, vol. 26, No. 7, C30, p. 914.

\* cited by examiner

Ad5-CMV-KpnI-NotI pA
6217 BP

```
misc_feature    1..26
                /note="PacI restriction site TTAATTAA"
misc_feature    11..16
                /note="NheI site GCTAGC"
frag            <27..>365
                /note="1 to 353 of Adenovirus-5"
misc_feature    913..1002
                /note="Multiple cloning site KpnI to NotI"
misc_feature    1437..1442
                /note="BglII restriction site AGATCT"
polyA_signal    995..1442
                /note="SV40 pREP8"
frag            <1443..>3897
                /note="3328 to 5792 of Adenovirus-5"
frag            3898..4344
                /note="652 to 1098 of pBR322"
frag            4345..6217
                /note="2489 to 4361 of pBR322"
CDS             complement(5149..6009)
                /note="beta-lactamase; E-286"
promoter        374..912
                /note="CMV promoter"

underlined polyA rev primer site

BASE COUNT    1391 A    1543 C    1732 G    1550 T    1 OTHER
ORIGIN
    1 AATTAATTAA GCTAGCATCA TCAATAATAT ACCTTATTTT GGATTGAAGC CAATATGATA
   61 ATGAGGGGGT GGAGTTTGTG ACGTGGCGCG GGGCGTGGGA ACGGGGCGGG TGACGTAGTA
  121 GTGTGGCGGA AGTGTGATGT TGCAAGTGTG GCGGAACACA TGTAAGCGAC GGATGTGGCA
  181 AAAGTGACGT TTTTGGTGTG CGCCGGTGTA CACAGGAAGT GACAATTTTC GCGCGGTTTT
  241 AGGCGGATGT TGTAGTAAAT TTGGGCGTAA CCGAGTAAGA TTTGGCCATT TTCGCGGGAA
  301 AACTGAATAA GAGGAAGTGA AATCTGAATA ATTTTGTGTT ACTCATAGCG CGTAATATTT
  361 GTCTAGGGAG ATCAGCCTGC AGGTCGTTAC ATAACTTACG GTAAATGGCC CGCCTGGCTG
  421 ACCGCCCAAC GACCCCCGCC CATTGACGTC AATAATGACG TATGTTCCCA TAGTAACGCC
  481 AATAGGGACT TTCCATTGAC GTCAATGGGT GGAGTATTTA CGGTAAACTG CCCACTTGGC
  541 AGTACATCAA GTGTATCATA TGCCAAGTAC GCCCCCTATT GACGTCAATG ACGGTAAATG
  601 GCCCGCCTGG CATTATGCCC AGTACATGAC CTTATGGGAC TTTCCTACTT GGCAGTACAT
  661 CTACGTATTA GTCATCGCTA TTACCATGGT GATGCGGTTT TGGCAGTACA TCAATGGGCG
  721 TGGATAGCGG TTTGACTCAC GGGGATTTCC AAGTCTCCAC CCCATTGACG TCAATGGGAG
  781 TTTGTTTTGG CACCAAAATC AACGGGACTT TCCAAAATGT CGTAACAACT CCGCCCCATT
  841 GACGCAAATG GGCGGTAGGC GTGTACGGTG GGAGGTCTAT ATAAGCAGAG CTCGTTTAGT
  901 GAACCGTCAG ATGGTACCGT TTAAACTCGA GGTCGACGGT ATCGATAAGC TTGATATCGA
  961 ATTCCTGCAG CCCGGGGGAT CCACTAGTTC TAGAGCGGCC GCCACCGCGG GGAGATCCAG
 1021 ACATGATAAG ATACATTGAT GAGTTTGGAC AAACCACAAC TAGAATGCAG TGAAAAAAAT
 1081 GCTTTATTTG TGAAATTTGT GATGCTATTG CTTTATTTGT AACCATTATA AGCTGCAATA
 1141 AACAAGTTAA CAACAACAAT TGCATTCATT TTATGTTTCA GGTTCAGGGG GAGGTGTGGG
 1201 AGGTTTTTTA AAGCAAGTAA AACCTCTACA AATGTGGTAT GGCTGATTAT GATCCCGGCT
 1261 GCCTCGCGCG TTTCGGTGAT GACGGTGAAA ACCTCTTGAC ACATGCAGCT CCCGGAGACG
 1321 GTCACAGCTT GTCTGTAAGC GGATGCCGGG AGCAGACAAG CCCGTCAGGG CGCGTCAGCG
```

Fig. 16a

```
1381 GGTGTTGGCG GGTGTCGGGG CGCAGCCATG AGGTCGACTC TAGTCCCCGC GGTGGCAGAT
1441 CTGGAAGGTG CTGAGGTACG ATGAGACCCG CACCAGGTGC AGACCCTGCG AGTGTGGCGG
1501 TAAACATATT AGGAACCAGC CTGTGATGCT GGATGTGACC GAGGAGCTGA GGCCCGATCA
1561 CTTGGTGCTG GCCTGCACCC GCGCTGAGTT TGGCTCTAGC GATGAAGATA CAGATTGAGG
1621 TACTGAAATG TGTGGGCGTG GCTTAAGGGT GGGAAAGAAT ATATAAGGTG GGGGTCTTAT
1681 GTAGTTTTGT ATCTGTTTTG CAGCAGCCGC CGCCGCCATG AGCACCAACT CGTTTGATGG
1741 AAGCATTGTG AGCTCATATT TGACAACGCG CATGCCCCCA TGGGCCGGGG TGCGTCAGAA
1801 TGTGATGGGC TCCAGCATTG ATGGTCGCCC CGTCCTGCCC GCAAACTCTA CTACCTTGAC
1861 CTACGAGACC GTGTCTGGAA CGCCGTTGGA GACTGCAGCC TCCGCCGCCG CTTCAGCCGC
1921 TGCAGCCACC GCCCGCGGGA TTGTGACTGA CTTTGCTTTC CTGAGCCCGC TTGCAAGCAG
1981 TGCAGCTTCC CGTTCATCCG CCCGCGATGA CAAGTTGACG GCTCTTTTGG CACAATTGGA
2041 TTCTTTGACC CGGGAACTTA ATGTCGTTTC TCAGCAGCTG TTGGATCTGC GCCAGCAGGT
2101 TTCTGCCCTG AAGGCTTCCT CCCCTCCCAA TGCGGTTTAA AACATAAATA AAAAACCAGA
2161 CTCTGTTTGG ATTTGGATCA AGCAAGTGTC TTGCTGTCTT TATTTAGGGG TTTTGCGCGC
2221 GCGGTAGGCC CGGGACCAGC GGTCTCGGTC GTTGAGGGTC CTGTGTATTT TTTCCAGGAC
2281 GTGGTAAAGG TGACTCTGGA TGTTCAGATA CATGGGCATA AGCCCGTCTC TGGGGTGGAG
2341 GTAGCACCAC TGCAGAGCTT CATGCTGCGG GGTGGTGTTG TAGATGATCC AGTCGTAGCA
2401 GGAGCGCTGG GCGTGGTGCC TAAAAATGTC TTTCAGTAGC AAGCTGATTG CCAGGGGCAG
2461 GCCCTTGGTG TAAGTGTTTA CAAAGCGGTT AAGCTGGGAT GGGTGCATAC GTGGGGATAT
2521 GAGATGCATC TTGGACTGTA TTTTTAGGTT GGCTATGTTC CCAGCCATAT CCCTCCGGGG
2581 ATTCATGTTG TGCAGAACCA CCAGCACAGT GTATCCGGTG CACTTGGGAA ATTTGTCATG
2641 TAGCTTAGAA GGAAATGCGT GGAAGAACTT GGAGACGCCC TTGTGACCTC CAAGATTTTC
2701 CATGCATTCG TCCATAATGA TGGCAATGGG CCCACGGGCG GCGGCCTGGG CGAAGATATT
2761 TCTGGGATCA CTAACGTCAT AGTTGTGTTC CAGGATGAGA TCGTCATAGG CCATTTTTAC
2821 AAAGCGCGGG CGGAGGGTGC CAGACTGCGG TATAATGGTT CCATCCGGCC CAGGGGCGTA
2881 GTTACCCTCA CAGATTTGCA TTTCCCACGC TTTGAGTTCA GATGGGGGGA TCATGTCTAC
2941 CTGCGGGGCG ATGAAGAAAA CGGTTTCCGG GGTAGGGGAG ATCAGCTGGG AAGAAAGCAG
3001 GTTCCTGAGC AGCTGCGACT TACCGCAGCC GGTGGGCCCG TAAATCACAC CTATTACCGG
3061 GTGCAACTGG TAGTTAAGAG AGCTGCAGCT GCCGTCATCC CTGAGCAGGG GGGCCACTTC
3121 GTTAAGCATG TCCCTGACTC GCATGTTTTC CCTGACCAAA TCCGCCAGAA GGCGCTCGCC
3181 GCCCAGCGAT AGCAGTTCTT GCAAGGAAGC AAAGTTTTTC AACGGTTTGA GACCGTCCGC
3241 CGTAGGCATG CTTTTGAGCG TTTGACCAAG CAGTTCCAGG CGGTCCCACA GCTCGGTCAC
3301 CTGCTCTACG GCATCTCGAT CCAGCATATC TCCTCGTTTC GCGGGTTGGG GCGGCTTTCG
3361 CTGTACGGCA GTAGTCGGTG CTCGTCCAGA CGGGCCAGGG TCATGTCTTT CCACGGGCGC
3421 AGGGTCCTCG TCAGCGTAGT CTGGGTCACG GTGAAGGGGT GCGCTCCGGG CTGCGCGCTG
3481 GCCAGGGTGC GCTTGAGGCT GGTCCTGCTG GTGCTGAAGC GCTGCCGGTC TTCGCCCTGC
3541 GCGTCGGCCA GGTAGCATTT GACCATGGTG TCATAGTCCA GCCCCTCCGC GGCGTGGCCC
3601 TTGGCGCGCA GCTTGCCCTT GGAGGAGGCG CCGCACGAGG GGCAGTGCAG ACTTTTGAGG
3661 GCGTAGAGCT TGGGCGCGAG AAATACCGAT TCCGGGGAGT AGGCATCCGC GCCGCAGGCC
3721 CCGCAGACGG TCTCGCATTC CACGAGCGTG GCCGTTCGGG GTCAAAAACC
3781 AGGTTTCCCC CATGCTTTTT GATGCGTTTC TTACCTCTGG TTTCCATGAG CCGGTGTCCA
3841 CGCTCGGTGA CGAAAAGGCT GTCCGTGTCC CCGTATACAG ACTTGAGAGG CCTGTCCTCG
3901 ACCGATGCCC TTGAGAGCCT TCAACCCAGT CAGCTCCTTC CGGTGGGCGC GGGGCATGAC
3961 TATCGTCGCC GCACTTATGA CTGTCTTCTT TATCATGCAA CTCGTAGGAC AGGTGCCGGC
4021 AGCGCTCTGG GTCATTTTCG GCGAGGACCG CTTTCGCTGG AGCGCGACGA TGATCGGCCT
4081 GTCGCTTGCG GTATTCGGAA TCTTGCACGC CCTCGCTCAA GCCTTCGTCA CTGGTCCCGC
4141 CACCAAACGT TTCGGCGAGA AGCAGGCCAT TATCGCCGGC ATGGCGGCCG ACGCGCTGGG
4201 CTACGTCTTG CTGGCGTTCG CGACGCGAGG CTGGATGGCC TTCCCCATTA TGATTCTTCT
4261 CGCTTCCGGC GGCATCGGGA TGCCCGCGTT GCAGGCCATG CTGTCCAGGC AGGTAGATGA
4321 CGACCATCAG GGACAGCTTC AAGGCCAGCA AAAGGCCAGG AACCGTAAAA AGGCCGCGTT
4381 GCTGGCGTTT TTCCATAGGC TCCGCCCCCC TGACGAGCAT CACAAAAATC GACGCTCAAG
4441 TCAGAGGTGG CGAAACCCGA CAGGACTATA AAGATACCAG GCGTTTCCCC CTGGAAGCTC
4501 CCTCGTGCGC TCTCCTGTTC CGACCCTGCC GCTTACCGGA TACCTGTCCG CCTTTCTCCC
4561 TTCGGGAAGC GTGGCGCTTT CTCATAGCTC ACGCTGTAGG TATCTCAGTT CGGTGTAGGT
4621 CGTTCGCTCC AAGCTGGGCT GTGTGCACGA ACCCCCCGTT CAGCCCGACC GCTGCGCCTT
4681 ATCCGGTAAC TATCGTCTTG AGTCCAACCC GGTAAGACAC GACTTATCGC CACTGGCAGC
4741 AGCCACTGGT AACAGGATTA GCAGAGCGAG GTATGTAGGC GGTGCTACAG AGTTCTTGAA
```

Fig. 16b

```
4801  GTGGTGGCCT AACTACGGCT ACACTAGAAG GACAGTATTT GGTATCTGCG CTCTGCTGAA
4861  GCCAGTTACC TTCGGAAAAA GAGTTGGTAG CTCTTGATCC GGCAAACAAA CCACCGCTGG
4921  TAGCGGTGGT TTTTTTGTTT GCAAGCAGCA GATTACGCGC AGAAAAAAAG GATCTCAAGA
4981  AGATCCTTTG ATCTTTTCTA CGGGGTCTGA CGCTCAGTGG AACGAAAACT CACGTTAAGG
5041  GATTTTGGTC ATGAGATTAT CAAAAAGGAT CTTCACCTAG ATCCTTTTAA ATTAAAAATG
5101  AAGTTTTAAA TCAATCTAAA GTATATATGA GTAAACTTGG TCTGACAGTT ACCAATGCTT
5161  AATCAGTGAG GCACCTATCT CAGCGATCTG TCTATTTCGT TCATCCATAG TTGCCTGACT
5221  CCCCGTCGTG TAGATAACTA CGATACGGGA GGGCTTACCA TCTGGCCCCA GTGCTGCAAT
5281  GATACCGCGA GACCCACGCT CACCGGCTCC AGATTTATCA GCAATAAACC AGCCAGCCGG
5341  AAGGGCCGAG CGCAGAAGTG GTCCTGCAAC TTTATCCGCC TCCATCCAGT CTATTAATTG
5401  TTGCCGGGAA GCTAGAGTAA GTAGTTCGCC AGTTAATAGT TTGCGCAACG TTGTTGCCAT
5461  TGCTGCAGGC ATCGTGGTGT CACGCTCGTC GTTTGGTATG GCTTCATTCA GCTCCGGTTC
5521  CCAACGATCA AGGCGAGTTA CATGATCCCC CATGTTGTGC AAAAAAGCGG TTAGCTCCTT
5581  CGGTCCTCCG ATCGTTGTCA GAAGTAAGTT GGCCGCAGTG TTATCACTCA TGGTTATGGC
5641  AGCACTGCAT AATTCTCTTA CTGTCATGCC ATCCGTAAGA TGCTTTTCTG TGACTGGTGA
5701  GTACTCAACC AAGTCATTCT GAGAATAGTG TATGCGGCGA CCGAGTTGCT CTTGCCCGGC
5761  GTCAACACGG GATAATACCG CGCCACATAG CAGAACTTTA AAAGTGCTCA TCATTGGAAA
5821  ACGTTCTTCG GGGCGAAAAC TCTCAAGGAT CTTACCGCTG TTGAGATCCA GTTCGATGTA
5881  ACCCACTCGT GCACCCAACT GATCTTCAGC ATCTTTTACT TTCACCAGCG TTTCTGGGTG
5941  AGCAAAAACA GGAAGGCAAA ATGCCGCAAA AAAGGGAATA AGGGCGACAC GGAAATGTTG
6001  AATACTCATA CTCTTCCTTT TTCAATATTA TTGAAGCATT TATCAGGGTT ATTGTCTCAT
6061  GAGCGGATAC ATATTTGAAT GTATTTAGAA AAATAAACAA ATAGGGGTTC CGCGCACATT
6121  TCCCCGAAAA GTGCCACCTG ACGTCTAAGA AACCATTATT ATCATGACAT TAACCTATAA
6181  AAATAGGCGT ATCACGAGGC CCTTTCGTCT TCAAGAA
```

Fig. 16c

SEQUENCE LISTING

```
<160> NUMBER OF SEQ ID NOS: 98

<210> SEQ ID NO 1
<211> LENGTH: 110
<212> TYPE: DNA
<213> ORGANISM: artificial
<220> FEATURE:
<223> OTHER INFORMATION: miR-199b nucleotide sequence
```

<400> SEQUENCE: 1

```
ccagaggaca cctccactcc gtctacccag tgtttagact atctgttcag gactcccaaa    60
ttgtacagta gtctgcacat tggttaggct gggctgggtt agaccctcgg               110
```

<210> SEQ ID NO 2
<211> LENGTH: 6217
<212> TYPE: DNA
<213> ORGANISM: artificial
<220> FEATURE:
<223> OTHER INFORMATION: sequence of vector AdV5-CMV-KpnI-NotIpA 6217bp

<400> SEQUENCE: 2

```
aattaattaa gctagcatca tcaataatat accttatttt ggattgaagc caatatgata    60
atgaggggt ggagtttgtg acgtggcgcg gggcgtggga acgggcggg tgacgtagta    120
gtgtggcgga agtgtgatgt tgcaagtgtg gcggaacaca tgtaagcgac ggatgtggca   180
aaagtgacgt ttttggtgtg cgccggtgta cacaggaagt gacaattttc gcgcggtttt   240
aggcggatgt tgtagtaaat ttgggcgtaa ccgagtaaga tttggccatt ttcgcgggaa   300
aactgaataa gaggaagtga aatctgaata attttgtgtt actcatagcg cgtaatattt   360
gtctaggag atcagcctgc aggtcgttac ataacttacg gtaaatggcc cgcctggctg   420
accgcccaac gacccccgcc cattgacgtc aataatgacg tatgttccca tagtaacgcc   480
aatagggact ttccattgac gtcaatgggt ggagtattta cggtaaactg cccacttggc   540
agtacatcaa gtgtatcata tgccaagtac gccccctatt gacgtcaatg acggtaaatg   600
gcccgcctgg cattatgccc agtacatgac cttatgggac tttcctactt ggcagtacat   660
ctacgtatta gtcatcgcta ttaccatggt gatgcggttt tggcagtaca tcaatgggcg   720
tggatagcgg tttgactcac ggggatttcc aagtctccac cccattgacg tcaatgggag   780
tttgttttgg caccaaaatc aacgggactt tccaaaatgt cgtaacaact ccgccccatt   840
gacgcaaatg ggcggtaggc gtgtacggtg ggaggtctat ataagcagag ctcgtttagt   900
gaaccgtcag atggtaccgt ttaaactcga ggtcgacggt atcgataagc ttgatatcga   960
attcctgcag cccggggat ccactagttc tagagcggcc gccaccgcgg ggagatccag   1020
acatgataag atacattgat gagtttggac aaaccacaac tagaatgcag tgaaaaaaat   1080
gctttatttg tgaaatttgt gatgctattg ctttatttgt aaccattata agctgcaata   1140
aacaagttaa caacaacaat tgcattcatt ttatgtttca ggttcagggg gaggtgtggg   1200
aggtttttta aagcaagtaa aacctctaca aatgtggtat ggctgattat gatcccggct   1260
gcctcgcgcg tttcggtgat gacggtgaaa acctcttgac acatgcagct cccggagacg   1320
gtcacagctt gtctgtaagc ggatgccggg agcagacaag cccgtcaggg gcgtcagcg   1380
ggtgttggcg ggtgtcgggg cgcagccatg aggtcgactc tagtccccgc ggtggcagat   1440
ctggaaggtg ctgaggtacg atgagacccg caccaggtgc agaccctgcg agtgtggcgg   1500
taaacatatt aggaaccagc ctgtgatgct ggatgtgacc gaggagctga ggcccgatca   1560
cttggtgctg gcctgcaccc gcgctgagtt tggctctagc gatgaagata cagattgagg   1620
tactgaaatg tgtgggcgtg gcttaaggt gggaaagaat atataaggtg ggggtcttat   1680
gtagttttgt atctgttttg cagcagccgc cgccgccatg agcaccaact cgtttgatgg   1740
aagcattgtg agctcatatt tgacaacgcg catgccccca tgggccgggg tgcgtcagaa   1800
tgtgatgggc tccagcattg atggtcgccc cgtcctgccc gcaaactcta ctaccttgac   1860
ctacgagacc gtgtctggaa cgccgttgga gactgcagcc tccgccgccg cttcagccgc   1920
```

```
tgcagccacc gcccgcggga ttgtgactga ctttgctttc ctgagcccgc ttgcaagcag   1980
tgcagcttcc cgttcatccg cccgcgatga caagttgacg gctcttttgg cacaattgga   2040
ttctttgacc cgggaactta atgtcgtttc tcagcagctg ttggatctgc gccagcaggt   2100
ttctgccctg aaggcttcct cccctcccaa tgcggtttaa aacataaata aaaaaccaga   2160
ctctgtttgg atttggatca agcaagtgtc ttgctgtctt tatttagggg ttttgcgcgc   2220
gcggtaggcc cgggaccagc ggtctcggtc gttgagggtc ctgtgtattt tttccaggac   2280
gtggtaaagg tgactctgga tgttcagata catgggcata agcccgtctc tggggtggag   2340
gtagcaccac tgcagagctt catgctgcgg ggtggtgttg tagatgatcc agtcgtagca   2400
ggagcgctgg gcgtggtgcc taaaaatgtc tttcagtagc aagctgattg ccaggggcag   2460
gcccttggtg taagtgttta caaagcggtt aagctgggat gggtgcatac gtgggatat    2520 gagatgcatc ttggactgta tttttaggtt ggctatgttc ccagccatat ccctccgggg   2580
attcatgttg tgcagaacca ccagcacagt gtatccggtg cacttgggaa atttgtcatg   2640
tagcttagaa ggaaatgcgt ggaagaactt ggagacgccc ttgtgacctc caagattttc   2700
catgcattcg tccataatga tggcaatggg cccacgggcg gcggcctggg cgaagatatt   2760
tctgggatca ctaacgtcat agttgtgttc caggatgaga tcgtcatagg ccattttac    2820 aaagcgcggg cggagggtgc cagactgcgg tataatggtt ccatccggcc caggggcgta   2880
gttaccctca cagatttgca tttcccacgc tttgagttca gatgggggga tcatgtctac   2940
ctgcggggcg atgaagaaaa cggtttccgg ggtaggggag atcagctggg aagaaagcag   3000
gttcctgagc agctgcgact taccgcagcc ggtgggcccg taaatcacac ctattaccgg   3060
gtgcaactgg tagttaagag agctgcagct gccgtcatcc ctgagcaggg gggccacttc   3120
gttaagcatg tccctgactc gcatgttttc cctgaccaaa tccgccagaa ggcgctcgcc   3180
gcccagcgat agcagttctt gcaaggaagc aaagttttc aacggtttga ccgtccgc     3240 cgtaggcatg cttttgagcg tttgaccaag cagttccagg cggtcccaca gctcggtcac   3300
ctgctctacg gcatctcgat ccagcatatc tcctcgtttc gcgggttggg gcggctttcg   3360
ctgtacggca gtagtcggtg ctcgtccaga cgggccaggg tcatgtcttt ccacgggcgc   3420
agggtcctcg tcagcgtagt ctgggtcacg gtgaaggggt gcgctccggg ctgcgcgctg   3480
gccagggtgc gcttgaggct ggtcctgctg gtgctgaagc gctgccggtc ttcgccctgc   3540
gcgtcggcca ggtagcattt gaccatggtg tcatagtcca gcccctccgc ggcgtggccc   3600
ttggcgcgca gcttgccctt ggaggaggcg ccgcacgagg ggcagtgcag acttttgagg   3660
gcgtagagct tgggcgcgag aaataccgat tccggggagt aggcatccgc gccgcaggcc   3720
ccgcagacgg tctcgcattc cacgagccag gtgagctctg gccgttcggg gtcaaaaacc   3780
aggtttcccc catgcttttt gatgcgtttc ttacctctgg tttccatgag ccggtgtcca   3840
cgctcggtga cgaaaaggct gtccgtgtcc ccgtatacag acttgagagg cctgtcctcg   3900
accgatgccc ttgagagcct tcaacccagt cagctccttc cggtgggcgc ggggcatgac   3960
tatcgtcgcc gcacttatga ctgtcttctt tatcatgcaa ctcgtaggac aggtgccggc   4020
agcgctctgg gtcattttcg gcgaggaccg ctttcgctgg agcgcgacga tgatcggcct   4080
gtcgcttgcg gtattcggaa tcttgcacgc cctcgctcaa gccttcgtca ctggtccgc   4140 caccaaacgt ttcggcgaga agcaggccat tatcgccggc atggcggccg acgcgctggg   4200
ctacgtcttg ctggcgttcg cgacgcgagg ctggatggcc ttccccatta tgattcttct   4260
cgcttccggc ggcatcggga tgcccgcgtt gcaggccatg ctgtccaggc aggtagatga   4320
```

```
cgaccatcag ggacagcttc aaggccagca aaaggccagg aaccgtaaaa aggccgcgtt      4380
gctggcgttt ttccataggc tccgcccccc tgacgagcat cacaaaaatc gacgctcaag      4440
tcagaggtgg cgaaacccga caggactata agataccag gcgtttcccc ctggaagctc       4500
cctcgtgcgc tctcctgttc cgaccctgcc gcttaccgga tacctgtccg cctttctccc      4560
ttcgggaagc gtggcgcttt ctcatagctc acgctgtagg tatctcagtt cggtgtaggt      4620
cgttcgctcc aagctgggct gtgtgcacga accccccgtt cagcccgacc gctgcgcctt      4680
atccggtaac tatcgtcttg agtccaaccc ggtaagacac gacttatcgc cactggcagc      4740
agccactggt aacaggatta gcagagcgag gtatgtaggc ggtgctacag agttcttgaa      4800
gtggtggcct aactacggct acactagaag gacagtattt ggtatctgcg ctctgctgaa      4860
gccagttacc ttcggaaaaa gagttggtag ctcttgatcc ggcaaacaaa ccaccgctgg      4920
tagcggtggt ttttttgttt gcaagcagca gattacgcgc agaaaaaaag gatctcaaga      4980
agatcctttg atcttttcta cggggtctga cgctcagtgg aacgaaaact cacgttaagg      5040
gattttggtc atgagattat caaaaaggat cttcacctag atccttttaa attaaaaatg      5100
aagttttaaa tcaatctaaa gtatatatga gtaaacttgg tctgacagtt accaatgctt      5160
aatcagtgag gcacctatct cagcgatctg tctatttcgt tcatccatag ttgcctgact      5220
ccccgtcgtg tagataacta cgatacggga gggcttacca tctggcccca gtgctgcaat      5280
gataccgcga gacccacgct caccggctcc agatttatca gcaataaacc agccagccgg      5340
aagggccgag cgcagaagtg gtcctgcaac tttatccgcc tccatccagt ctattaattg      5400
ttgccgggaa gctagagtaa gtagttcgcc agttaatagt ttgcgcaacg ttgttgccat      5460
tgctgcaggc atcgtggtgt cacgctcgtc gtttggtatg gcttcattca gctccggttc      5520
ccaacgatca aggcgagtta catgatcccc catgttgtgc aaaaaagcgg ttagctcctt      5580
cggtcctccg atcgttgtca gaagtaagtt ggccgcagtg ttatcactca tggttatggc      5640
agcactgcat aattctctta ctgtcatgcc atccgtaaga tgcttttctg tgactggtga      5700
gtactcaacc aagtcattct gagaatagtg tatgcggcga ccgagttgct cttgcccggc      5760
gtcaacacgg gataataccg cgccacatag cagaacttta aaagtgctca tcattggaaa      5820
acgttcttcg gggcgaaaac tctcaaggat cttaccgctg ttgagatcca gttcgatgta      5880
acccactcgt gcacccaact gatcttcagc atcttttact ttcaccagcg tttctgggtg      5940
agcaaaaaca ggaaggcaaa atgccgcaaa aaagggaata agggcgacac ggaaatgttg      6000
aatactcata ctcttccttt ttcaatatta ttgaagcatt tatcagggtt attgtctcat      6060
gagcggatac atatttgaat gtatttagaa aaataaacaa ataggggttc cgcgcacatt      6120
tccccgaaaa gtgccacctg acgtctaaga aaccattatt atcatgacat taacctataa      6180
aaataggcgt atcacgaggc cctttcgtct tcaagaa                               6217
```

<210> SEQ ID NO 3
<211> LENGTH: 26
<212> TYPE: DNA
<213> ORGANISM: artificial
<220> FEATURE:
<223> OTHER INFORMATION: miRNA199b forward primer

<400> SEQUENCE: 3
cgggaattcc cagaggacac ctccac                                           26

```
<210> SEQ ID NO 4
<211> LENGTH: 26
<212> TYPE: DNA
<213> ORGANISM: artificial
<220> FEATURE:
<223> OTHER INFORMATION: miRNA199b reverse primer

<400> SEQUENCE: 4
cggctcgagc cgagggtcta acccag                                        26

<210> SEQ ID NO 5
<211> LENGTH: 22
<212> TYPE: DNA
<213> ORGANISM: artificial
<220> FEATURE:
<223> OTHER INFORMATION: U6miRNA forward primer

<400> SEQUENCE: 5
gaaaagcctt gtttgtgctt gc                                            22

<210> SEQ ID NO 6
<211> LENGTH: 22
<212> TYPE: DNA
<213> ORGANISM: artificial
<220> FEATURE:
<223> OTHER INFORMATION: U6 miRNA reverse primer

<400> SEQUENCE: 6
gggccatgct aatcttctct gt                                            22

<210> SEQ ID NO 7
<211> LENGTH: 22
<212> TYPE: DNA
<213> ORGANISM: artificial
<220> FEATURE:
<223> OTHER INFORMATION: miRNA199b forward primer

<400> SEQUENCE: 7
aggacacctc cactccgtct ac                                            22

<210> SEQ ID NO 8
<211> LENGTH: 24
<212> TYPE: DNA
<213> ORGANISM: artificial
<220> FEATURE:
<223> OTHER INFORMATION: miRNA199b reverse primer

<400> SEQUENCE: 8
gcctaaccaa tgtgcagact actg                                          24

<210> SEQ ID NO 9
<211> LENGTH: 36
<212> TYPE: DNA
<213> ORGANISM: artificial
<220> FEATURE:
<223> OTHER INFORMATION: miRNA199b probe

<400> SEQUENCE: 9
cagtgtttag actatctgtt caggactccc aaattg                             36

<210> SEQ ID NO 10
<211> LENGTH: 110
<212> TYPE: RNA
<213> ORGANISM: artificial
<220> FEATURE:
<223> OTHER INFORMATION: miR-199b sequence
```

```
<400> SEQUENCE: 10
ccagaggaca ccuccacucc gucuacccag uguuuagacu aucuguucag gacucccaaa      60
uuguacagua gucugcacau ugguuaggcu gggcuggguu agacccucgg               110

<210> SEQ ID NO 11
<211> LENGTH: 23
<212> TYPE: RNA
<213> ORGANISM: artificial
<220> FEATURE:
<223> OTHER INFORMATION: miR199b-5p sequence

<400> SEQUENCE: 11
cccaguguuu agacuaucug uuc                                             23

<210> SEQ ID NO 12
<211> LENGTH: 23
<212> TYPE: RNA
<213> ORGANISM: artificial
<220> FEATURE:
<223> OTHER INFORMATION: scramble CTR

<400> SEQUENCE: 12
gguuguaugc auucccuauc uac                                             23

<210> SEQ ID NO 13
<211> LENGTH: 81
<212> TYPE: DNA
<213> ORGANISM: artificial
<220> FEATURE:
<223> OTHER INFORMATION: CD133 amplified sequence

<400> SEQUENCE: 13
ctatgtggta cagccgcgtg atttcccaga agatactttg agaaaattct tacagaaggc      60
atatgaatcc aaaattgatt a                                               81

<210> SEQ ID NO 14
<211> LENGTH: 35
<212> TYPE: DNA
<213> ORGANISM: artificial
<220> FEATURE:
<223> OTHER INFORMATION: c-myc amplified sequence

<400> SEQUENCE: 14
aggaggaaca agaagatgag gaagaaatcg atgtt                                35

<210> SEQ ID NO 15
<211> LENGTH: 82
<212> TYPE: DNA
<213> ORGANISM: artificial
<220> FEATURE:
<223> OTHER INFORMATION: nanog amplified sequence

<400> SEQUENCE: 15
gcaaatgtct tctgctgaga tgcctcacac ggagactgtc tctcctcttc cttcctccat      60
ggatctgctt attcaggaca gc                                              82

<210> SEQ ID NO 16
<211> LENGTH: 81
<212> TYPE: DNA
<213> ORGANISM: artificial
<220> FEATURE:
<223> OTHER INFORMATION: Oct4 amplified sequence
```

-continued

<400> SEQUENCE: 16
actgcagcag atcagccaca tcgcccagca gcttgggctc gagaaggatg tggtccgagt    60
gtggttctgt aaccggcgcc a    81

<210> SEQ ID NO 17
<211> LENGTH: 51
<212> TYPE: DNA
<213> ORGANISM: artificial
<220> FEATURE:
<223> OTHER INFORMATION: TCFL1 amplified sequence

<400> SEQUENCE: 17
ccgcgggact atttcgccga agtgagaagg cctcaggaca gcgcgttctt t    51

<210> SEQ ID NO 18
<211> LENGTH: 51
<212> TYPE: DNA
<213> ORGANISM: artificial
<220> FEATURE:
<223> OTHER INFORMATION: ZIC1 amplified sequence

<400> SEQUENCE: 18
cagttcgctg cgcaaacaca tgaaggtcca cgaatcctcc tcgcagggct c    51

<210> SEQ ID NO 19
<211> LENGTH: 55
<212> TYPE: DNA
<213> ORGANISM: artificial
<220> FEATURE:
<223> OTHER INFORMATION: KLF5 amplified sequence

<400> SEQUENCE: 19
gcatccacta ctgcgattac cctggttgca caaaagttta taccaagtct tctca    55

<210> SEQ ID NO 20
<211> LENGTH: 51
<212> TYPE: DNA
<213> ORGANISM: artificial
<220> FEATURE:
<223> OTHER INFORMATION: HMGA1 amplified sequence

<400> SEQUENCE: 20
aaaaacaagg gtgctgccaa gacccggaaa accaccacaa ctccaggaag g    51

<210> SEQ ID NO 21
<211> LENGTH: 51
<212> TYPE: DNA
<213> ORGANISM: artificial
<220> FEATURE:
<223> OTHER INFORMATION: HMGB3 amplified sequence

<400> SEQUENCE: 21
ttttccaaga agtgctctga gaggtggaag acgatgtccg ggaaagagaa a    51

<210> SEQ ID NO 22
<211> LENGTH: 20
<212> TYPE: DNA
<213> ORGANISM: artificial
<220> FEATURE:
<223> OTHER INFORMATION: CD133 forward primer

<400> SEQUENCE: 22
ctatgtggta cagccgcgtg    20

```
<210> SEQ ID NO 23
<211> LENGTH: 27
<212> TYPE: DNA
<213> ORGANISM: artificial
<220> FEATURE:
<223> OTHER INFORMATION: CD133 reverse primer

<400> SEQUENCE: 23
taatcaattt tggattcata tgccttc                                              27

<210> SEQ ID NO 24
<211> LENGTH: 19
<212> TYPE: DNA
<213> ORGANISM: artificial
<220> FEATURE:
<223> OTHER INFORMATION: c-myc forward primer

<400> SEQUENCE: 24
atgaggagac accgcccac                                                       19

<210> SEQ ID NO 25
<211> LENGTH: 26
<212> TYPE: DNA
<213> ORGANISM: artificial
<220> FEATURE:
<223> OTHER INFORMATION: c-myc reverse primer

<400> SEQUENCE: 25
aacatcgatt tcttcctcat cttctt                                               26

<210> SEQ ID NO 26
<211> LENGTH: 23
<212> TYPE: DNA
<213> ORGANISM: artificial
<220> FEATURE:
<223> OTHER INFORMATION: Nanog forward primer

<400> SEQUENCE: 26
gcaaatgtct tctgctgaga tgc                                                  23

<210> SEQ ID NO 27
<211> LENGTH: 24
<212> TYPE: DNA
<213> ORGANISM: artificial
<220> FEATURE:
<223> OTHER INFORMATION: Nanog reverse primer

<400> SEQUENCE: 27
gctgtcctga ataagcagat ccat                                                 24

<210> SEQ ID NO 28
<211> LENGTH: 20
<212> TYPE: DNA
<213> ORGANISM: artificial
<220> FEATURE:
<223> OTHER INFORMATION: Oct4 forward primer

<400> SEQUENCE: 28
actgcagcag atcagccaca                                                      20

<210> SEQ ID NO 29
<211> LENGTH: 18
<212> TYPE: DNA
<213> ORGANISM: artificial
<220> FEATURE:
<223> OTHER INFORMATION: Oct4 reverse primer
```

<400> SEQUENCE: 29
tggcgccggt tacagaac                                              18

<210> SEQ ID NO 30
<211> LENGTH: 17
<212> TYPE: DNA
<213> ORGANISM: artificial
<220> FEATURE:
<223> OTHER INFORMATION: TCFL1 forward primer

<400> SEQUENCE: 30
ccgcgggact atttcgc                                               17

<210> SEQ ID NO 31
<211> LENGTH: 20
<212> TYPE: DNA
<213> ORGANISM: artificial
<220> FEATURE:
<223> OTHER INFORMATION: TCFL1 reverse primer

<400> SEQUENCE: 31
aaagaacgcg ctgtcctgag                                            20

<210> SEQ ID NO 32
<211> LENGTH: 18
<212> TYPE: DNA
<213> ORGANISM: artificial
<220> FEATURE:
<223> OTHER INFORMATION: ZIC1 forward primer

<400> SEQUENCE: 32
cagttcgctg cgcaaaca                                              18

<210> SEQ ID NO 33
<211> LENGTH: 18
<212> TYPE: DNA
<213> ORGANISM: artificial
<220> FEATURE:
<223> OTHER INFORMATION: ZIC1 reverse primer

<400> SEQUENCE: 33
gagccctgcg aggaggat                                              18

<210> SEQ ID NO 34
<211> LENGTH: 22
<212> TYPE: DNA
<213> ORGANISM: artificial
<220> FEATURE:
<223> OTHER INFORMATION: KLF5 forward primer

<400> SEQUENCE: 34
gcatccacta ctgcgattac cc                                         22

<210> SEQ ID NO 35
<211> LENGTH: 28
<212> TYPE: DNA
<213> ORGANISM: artificial
<220> FEATURE:
<223> OTHER INFORMATION: KLF5 reverse primer

<400> SEQUENCE: 35
tgagaagact tggtataaac ttttgtgc                                   28

```
<210> SEQ ID NO 36
<211> LENGTH: 20
<212> TYPE: DNA
<213> ORGANISM: artificial
<220> FEATURE:
<223> OTHER INFORMATION: HMGA1 forward primer

<400> SEQUENCE: 36
aaaaacaagg gtgctgccaa                                                20

<210> SEQ ID NO 37
<211> LENGTH: 21
<212> TYPE: DNA
<213> ORGANISM: artificial
<220> FEATURE:
<223> OTHER INFORMATION: HMGA1 reverse primer

<400> SEQUENCE: 37
ccttcctgga gttgtggtgg t                                              21

<210> SEQ ID NO 38
<211> LENGTH: 24
<212> TYPE: DNA
<213> ORGANISM: artificial
<220> FEATURE:
<223> OTHER INFORMATION: HMGB3 forward primer

<400> SEQUENCE: 38
ttttccaaga agtgctctga gagg                                           24

<210> SEQ ID NO 39
<211> LENGTH: 20
<212> TYPE: DNA
<213> ORGANISM: artificial
<220> FEATURE:
<223> OTHER INFORMATION: HMGB3 reverse primer

<400> SEQUENCE: 39
tttctctttc ccggacatcg                                                20

<210> SEQ ID NO 40
<211> LENGTH: 81
<212> TYPE: DNA
<213> ORGANISM: artificial
<220> FEATURE:
<223> OTHER INFORMATION: cd133 amplified sequence

<400> SEQUENCE: 40
tccacagaaa tttacctaca ttggaagagt atgattcata ctggtggctg ggtggcctgg    60
tcatctgctc tctgctgacc c                                              81

<210> SEQ ID NO 41
<211> LENGTH: 81
<212> TYPE: DNA
<213> ORGANISM: artificial
<220> FEATURE:
<223> OTHER INFORMATION: c myc amplified sequence

<400> SEQUENCE: 41
gctggatttt tttcgggtag tggaaaacca gcagcctccc gcgacgatgc ccctcaacgt    60
tagcttcacc aacaggaact a                                              81
```

```
<210> SEQ ID NO 42
<211> LENGTH: 80
<212> TYPE: DNA
<213> ORGANISM: artificial
<220> FEATURE:
<223> OTHER INFORMATION: nanog amplified sequence

<400> SEQUENCE: 42
ccgaagaata gcaatggtgt gacgcagaag gcctcagcac ctacctaccc cagcctttac    60
tcttcctacc accagggatg                                                80

<210> SEQ ID NO 43
<211> LENGTH: 81
<212> TYPE: DNA
<213> ORGANISM: artificial
<220> FEATURE:
<223> OTHER INFORMATION: oct4 amplified sequence

<400> SEQUENCE: 43
aacccggagg aggtagtcct ttgttacatg catgagtcag tgaacaggga atgggtgaat    60
gacatttgtg ggtaggttat t                                              81

<210> SEQ ID NO 44
<211> LENGTH: 81
<212> TYPE: DNA
<213> ORGANISM: artificial
<220> FEATURE:
<223> OTHER INFORMATION: tcfl1 amplified sequence

<400> SEQUENCE: 44
ccaaggaaga gaacgttgac atagaaggct ctttgtgttt tccttgtct tttgtcctca     60 gacttgatcc tgctccctcg g                                              81

<210> SEQ ID NO 45
<211> LENGTH: 80
<212> TYPE: DNA
<213> ORGANISM: artificial
<220> FEATURE:
<223> OTHER INFORMATION: zic1 amplified sequence

<400> SEQUENCE: 45
cgcgctccga gaatttaaag atccacaaaa ggacgcacac agggagaagc ccttcaagtg    60
cgagtttgag ggctgtgacc                                                80

<210> SEQ ID NO 46
<211> LENGTH: 81
<212> TYPE: DNA
<213> ORGANISM: artificial
<220> FEATURE:
<223> OTHER INFORMATION: KLF5 amplified sequence

<400> SEQUENCE: 46
tttaacccca cctccatcct atgctgctac aattgcttct aaactggcaa ttcacaatcc    60
aaatttaccc accacctgc c                                               81

<210> SEQ ID NO 47
<211> LENGTH: 77
<212> TYPE: DNA
<213> ORGANISM: artificial
<220> FEATURE:
<223> OTHER INFORMATION: HMGA1 amplified sequence
```

```
<400> SEQUENCE: 47
ccccaggcag accttatatg agacatggga gtcccaccgt attgtccagg ctggtctcga    60
actcctgacc tcaagca                                                  77

<210> SEQ ID NO 48
<211> LENGTH: 81
<212> TYPE: DNA
<213> ORGANISM: artificial
<220> FEATURE:
<223> OTHER INFORMATION: HMGB3 amplified sequence

<400> SEQUENCE: 48
cgctatgatc gggaaatgaa ggattatgga ccagctaagg gaggcaagaa gaagaaggat    60
cctaatgctc ccaaaaggcc a                                             81

<210> SEQ ID NO 49
<211> LENGTH: 26
<212> TYPE: DNA
<213> ORGANISM: artificial
<220> FEATURE:
<223> OTHER INFORMATION: cd133 forward primer

<400> SEQUENCE: 49
tccacagaaa tttacctaca ttggaa                                        26

<210> SEQ ID NO 50
<211> LENGTH: 21
<212> TYPE: DNA
<213> ORGANISM: artificial
<220> FEATURE:
<223> OTHER INFORMATION: cd133 reverse primer

<400> SEQUENCE: 50
gggtcagcag agagcagatg a                                             21

<210> SEQ ID NO 51
<211> LENGTH: 29
<212> TYPE: DNA
<213> ORGANISM: artificial
<220> FEATURE:
<223> OTHER INFORMATION: cd133 probe

<400> SEQUENCE: 51
agtatgattc atactggtgg ctgggtggc                                     29

<210> SEQ ID NO 52
<211> LENGTH: 22
<212> TYPE: DNA
<213> ORGANISM: artificial
<220> FEATURE:
<223> OTHER INFORMATION: c myc forward primer

<400> SEQUENCE: 52
gctggatttt tttcgggtag tg                                            22

<210> SEQ ID NO 53
<211> LENGTH: 24
<212> TYPE: DNA
<213> ORGANISM: artificial
<220> FEATURE:
<223> OTHER INFORMATION: c myc reverse primer

<400> SEQUENCE: 53
tagttcctgt tggtgaagct aacg                                          24
```

```
<210> SEQ ID NO 54
<211> LENGTH: 18
<212> TYPE: DNA
<213> ORGANISM: artificial
<220> FEATURE:
<223> OTHER INFORMATION: c myc probe

<400> SEQUENCE: 54
cagcagcctc ccgcgacg                                               18

<210> SEQ ID NO 55
<211> LENGTH: 22
<212> TYPE: DNA
<213> ORGANISM: artificial
<220> FEATURE:
<223> OTHER INFORMATION: nanog forward primer

<400> SEQUENCE: 55
ccgaagaata gcaatggtgt ga                                          22

<210> SEQ ID NO 56
<211> LENGTH: 21
<212> TYPE: DNA
<213> ORGANISM: artificial
<220> FEATURE:
<223> OTHER INFORMATION: nanog reverse primer

<400> SEQUENCE: 56
gcatccctgg tggtaggaag a                                           21

<210> SEQ ID NO 57
<211> LENGTH: 25
<212> TYPE: DNA
<213> ORGANISM: artificial
<220> FEATURE:
<223> OTHER INFORMATION: nanog probe

<400> SEQUENCE: 57
cagcacctac ctaccccagc cttta                                       25

<210> SEQ ID NO 58
<211> LENGTH: 21
<212> TYPE: DNA
<213> ORGANISM: artificial
<220> FEATURE:
<223> OTHER INFORMATION: oct4 forward primer

<400> SEQUENCE: 58
aacccggagg aggtagtcct t                                           21

<210> SEQ ID NO 59
<211> LENGTH: 26
<212> TYPE: DNA
<213> ORGANISM: artificial
<220> FEATURE:
<223> OTHER INFORMATION: oct4 reverse primer

<400> SEQUENCE: 59
aataacctac ccacaaatgt cattca                                      26

<210> SEQ ID NO 60
<211> LENGTH: 25
<212> TYPE: DNA
<213> ORGANISM: artificial
<220> FEATURE:
<223> OTHER INFORMATION: oct4 probe
```

```
<400> SEQUENCE: 60
catgcatgag tcagtgaaca gggaa                                           25

<210> SEQ ID NO 61
<211> LENGTH: 24
<212> TYPE: DNA
<213> ORGANISM: artificial
<220> FEATURE:
<223> OTHER INFORMATION: tcfl1 forward primer

<400> SEQUENCE: 61
ccaaggaaga gaacgttgac atag                                            24

<210> SEQ ID NO 62
<211> LENGTH: 19
<212> TYPE: DNA
<213> ORGANISM: artificial
<220> FEATURE:
<223> OTHER INFORMATION: tcfl1 reverse primer

<400> SEQUENCE: 62
ccgagggagc aggatcaag                                                  19

<210> SEQ ID NO 63
<211> LENGTH: 32
<212> TYPE: DNA
<213> ORGANISM: artificial
<220> FEATURE:
<223> OTHER INFORMATION: tcfl1 probe

<400> SEQUENCE: 63
aggctctttg tgtttttcct tgtcttttgt cc                                   32

<210> SEQ ID NO 64
<211> LENGTH: 20
<212> TYPE: DNA
<213> ORGANISM: artificial
<220> FEATURE:
<223> OTHER INFORMATION: zic1 forward primer

<400> SEQUENCE: 64
cgcgctccga gaatttaaag                                                 20

<210> SEQ ID NO 65
<211> LENGTH: 20
<212> TYPE: DNA
<213> ORGANISM: artificial
<220> FEATURE:
<223> OTHER INFORMATION: zic1 reverse primer

<400> SEQUENCE: 65
cggtcacagc cctcaaactc                                                 20

<210> SEQ ID NO 66
<211> LENGTH: 23
<212> TYPE: DNA
<213> ORGANISM: artificial
<220> FEATURE:
<223> OTHER INFORMATION: zic1 probe

<400> SEQUENCE: 66
tccacaaaag gacgcacaca ggg                                             23
```

```
<210> SEQ ID NO 67
<211> LENGTH: 23
<212> TYPE: DNA
<213> ORGANISM: artificial
<220> FEATURE:
<223> OTHER INFORMATION: KLF5 forward primer

<400> SEQUENCE: 67
tttaacccca cctccatcct atg                                            23

<210> SEQ ID NO 68
<211> LENGTH: 20
<212> TYPE: DNA
<213> ORGANISM: artificial
<220> FEATURE:
<223> OTHER INFORMATION: KLF5 reverse primer

<400> SEQUENCE: 68
ggcagggtgg tgggtaaatt                                                20

<210> SEQ ID NO 69
<211> LENGTH: 26
<212> TYPE: DNA
<213> ORGANISM: artificial
<220> FEATURE:
<223> OTHER INFORMATION: KLF5 probe

<400> SEQUENCE: 69
tgcttctaaa ctggcaattc acaatc                                         26

<210> SEQ ID NO 70
<211> LENGTH: 22
<212> TYPE: DNA
<213> ORGANISM: artificial
<220> FEATURE:
<223> OTHER INFORMATION: HMGA1 forward primer

<400> SEQUENCE: 70
ccccaggcag accttatatg ag                                             22

<210> SEQ ID NO 71
<211> LENGTH: 21
<212> TYPE: DNA
<213> ORGANISM: artificial
<220> FEATURE:
<223> OTHER INFORMATION: HMGA1 reverse primer

<400> SEQUENCE: 71
tgcttgaggt caggagttcg a                                              21

<210> SEQ ID NO 72
<211> LENGTH: 25
<212> TYPE: DNA
<213> ORGANISM: artificial
<220> FEATURE:
<223> OTHER INFORMATION: HMGA1 probe

<400> SEQUENCE: 72
catgggagtc ccaccgtatt gtcca                                          25

<210> SEQ ID NO 73
<211> LENGTH: 21
<212> TYPE: DNA
<213> ORGANISM: artificial
<220> FEATURE:
<223> OTHER INFORMATION: HMGB3 forward primer
```

<400> SEQUENCE: 73
cgctatgatc gggaaatgaa g                                              21

<210> SEQ ID NO 74
<211> LENGTH: 20
<212> TYPE: DNA
<213> ORGANISM: artificial
<220> FEATURE:
<223> OTHER INFORMATION: HMGB3 reverse primer

<400> SEQUENCE: 74
tggccttttg ggagcattag                                                20

<210> SEQ ID NO 75
<211> LENGTH: 26
<212> TYPE: DNA
<213> ORGANISM: artificial
<220> FEATURE:
<223> OTHER INFORMATION: HMGB3 probe

<400> SEQUENCE: 75
attatggacc agctaaggga ggcaag                                         26

<210> SEQ ID NO 76
<211> LENGTH: 31
<212> TYPE: DNA
<213> ORGANISM: artificial
<220> FEATURE:
<223> OTHER INFORMATION: HES1 3'UTR sense primer

<400> SEQUENCE: 76
aaaatctaga cagttcgaag acataaaagc c                                   31

<210> SEQ ID NO 77
<211> LENGTH: 28
<212> TYPE: DNA
<213> ORGANISM: artificial
<220> FEATURE:
<223> OTHER INFORMATION: HES1 3'UTR antisense primer

<400> SEQUENCE: 77
aaaatctaga aacgcagtgt caccttcc                                       28

<210> SEQ ID NO 78
<211> LENGTH: 36
<212> TYPE: DNA
<213> ORGANISM: artificial
<220> FEATURE:
<223> OTHER INFORMATION: sense primer for the specific mutagenesis of
    miR-199b-5p linking site in HES1 3'UTR

<400> SEQUENCE: 78
aacaggaact tgaatatttg tagagaagag gacttt                              36

<210> SEQ ID NO 79
<211> LENGTH: 17
<212> TYPE: DNA
<213> ORGANISM: artificial
<220> FEATURE:
<223> OTHER INFORMATION: actin beta forward primer

<400> SEQUENCE: 79
cgtgctgctg accgagg                                                   17

```
<210> SEQ ID NO 80
<211> LENGTH: 24
<212> TYPE: DNA
<213> ORGANISM: artificial
<220> FEATURE:
<223> OTHER INFORMATION: actin beta reverse primer

<400> SEQUENCE: 80
gaaggtctca aacatgatct gggt                                              24

<210> SEQ ID NO 81
<211> LENGTH: 18
<212> TYPE: DNA
<213> ORGANISM: artificial
<220> FEATURE:
<223> OTHER INFORMATION: actin beta forward primer

<400> SEQUENCE: 81
gccaaccgcg agaagatg                                                     18

<210> SEQ ID NO 82
<211> LENGTH: 22
<212> TYPE: DNA
<213> ORGANISM: artificial
<220> FEATURE:
<223> OTHER INFORMATION: actin beta reverse primer

<400> SEQUENCE: 82
acagcctgga tagcaacgta ca                                                22

<210> SEQ ID NO 83
<211> LENGTH: 25
<212> TYPE: DNA
<213> ORGANISM: artificial
<220> FEATURE:
<223> OTHER INFORMATION: actin beta probe

<400> SEQUENCE: 83
cccaatcatg tttgagacct caac                                              25

<210> SEQ ID NO 84
<211> LENGTH: 18
<212> TYPE: DNA
<213> ORGANISM: artificial
<220> FEATURE:
<223> OTHER INFORMATION: PDGFR-B sense primer

<400> SEQUENCE: 84
aggttgctga cgagggcc                                                     18

<210> SEQ ID NO 85
<211> LENGTH: 22
<212> TYPE: DNA
<213> ORGANISM: artificial
<220> FEATURE:
<223> OTHER INFORMATION: PDGFR-B antisense primer

<400> SEQUENCE: 85
ggtgttgact tcattcaggg tg                                                22

<210> SEQ ID NO 86
<211> LENGTH: 21
<212> TYPE: DNA
<213> ORGANISM: artificial
<220> FEATURE:
<223> OTHER INFORMATION: PDGFR-A sense primer
```

```
<400> SEQUENCE: 86
tcaaggcaga ataggcagc a                                              21

<210> SEQ ID NO 87
<211> LENGTH: 19
<212> TYPE: DNA
<213> ORGANISM: artificial
<220> FEATURE:
<223> OTHER INFORMATION: PDGFR-A antisense primer

<400> SEQUENCE: 87
tggacgtcga tcaggtcca                                                19

<210> SEQ ID NO 88
<211> LENGTH: 20
<212> TYPE: DNA
<213> ORGANISM: artificial
<220> FEATURE:
<223> OTHER INFORMATION: SPARC sense primer

<400> SEQUENCE: 88
ttgcctggac tctgagctga                                               20

<210> SEQ ID NO 89
<211> LENGTH: 20
<212> TYPE: DNA
<213> ORGANISM: artificial
<220> FEATURE:
<223> OTHER INFORMATION: SPARC antisense primer

<400> SEQUENCE: 89
gggtgaccag gacgttcttg                                               20

<210> SEQ ID NO 90
<211> LENGTH: 18
<212> TYPE: DNA
<213> ORGANISM: artificial
<220> FEATURE:
<223> OTHER INFORMATION: ILF3 sense primer

<400> SEQUENCE: 90
ccgacacgcc aagtggtt                                                 18

<210> SEQ ID NO 91
<211> LENGTH: 21
<212> TYPE: DNA
<213> ORGANISM: artificial
<220> FEATURE:
<223> OTHER INFORMATION: ILF3 antisense primer

<400> SEQUENCE: 91
acacaagact tcagcccgtt g                                             21

<210> SEQ ID NO 92
<211> LENGTH: 21
<212> TYPE: DNA
<213> ORGANISM: artificial
<220> FEATURE:
<223> OTHER INFORMATION: MYBL2 sense primer

<400> SEQUENCE: 92
agcaagtgca aggtcaaatg g                                             21
```

```
<210> SEQ ID NO 93
<211> LENGTH: 17
<212> TYPE: DNA
<213> ORGANISM: artificial
<220> FEATURE:
<223> OTHER INFORMATION: MYBL2 antisense primer

<400> SEQUENCE: 93
ggccctcagc tgctcgt                                                  17

<210> SEQ ID NO 94
<211> LENGTH: 21
<212> TYPE: DNA
<213> ORGANISM: artificial
<220> FEATURE:
<223> OTHER INFORMATION: TEAD4 sense primer

<400> SEQUENCE: 94
tcggacgagg agggcaagat g                                             21

<210> SEQ ID NO 95
<211> LENGTH: 20
<212> TYPE: DNA
<213> ORGANISM: artificial
<220> FEATURE:
<223> OTHER INFORMATION: TEAD4 antisense primer

<400> SEQUENCE: 95
gatgtagcgg gcaatcagct                                               20

<210> SEQ ID NO 96
<211> LENGTH: 31
<212> TYPE: DNA
<213> ORGANISM: artificial sequence
<220> FEATURE:
<223> OTHER INFORMATION: synthetic polynucleotide

<400> SEQUENCE: 96
aaaatctaga cagttcgaag acataaaagc c                                  31

<210> SEQ ID NO 97
<211> LENGTH: 28
<212> TYPE: DNA
<213> ORGANISM: artificial sequence
<220> FEATURE:
<223> OTHER INFORMATION: synthetic polynucleotide

<400> SEQUENCE: 97
aaaatctaga aacgcagtgt caccttcc                                      28

<210> SEQ ID NO 98
<211> LENGTH: 36
<212> TYPE: DNA
<213> ORGANISM: artificial sequence
<220> FEATURE:
<223> OTHER INFORMATION: synthetic polynucleotide

<400> SEQUENCE: 98
aacaggaact tgaatatttg tagagaagag gacttt                             36
```

USE OF MICRORNA-199B-5P IN MEDICAL AND DIAGNOSTIC FIELD

CROSS REFERENCE TO RELATED APPLICATIONS

The present application is the US national stage of International Application PCT/IT2010/000125 filed on Mar. 23, 2010, which, in turn, claims priority to Italian Patent Application RM2009A000136 filed on Mar. 24, 2009.

This invention concerns the use of MicroRNA-199b-5p in medical and diagnostic fields. Particularly, this invention concerns the use of the miR199b-5p in the anti-cancer therapy and as a histophatological and metastasis marker.

MicroRNAs (miRNAs) are single-stranded RNAs of ~22 nucleotides in length, and they constitute a novel class of gene regulators [1]. In animals, miRNAs have regulatory effects through their binding to imperfect complementary sites within the 3'-untranslated regions (3'UTRs) of their mRNA targets. Altered expression of many miRNAs is observed in several tumor types: e.g. B-cell lymphomas (clustered miR-17)[2,3], malignant lymphomas (miR-15a, miR-16-1; targeting BCL2) [4], glioblastoma tumors (miR-21up-regulation) [5], colorectal neoplasia (miR-143, miR-145 down-regulated) [6], lung cancer (miR-29) [7], and breast cancer (miR-10b) [8], with several more tumor types under analysis.

Medulloblastomas (MBs) is the most common malignant brain tumors. It appears to originate from stem cells and from granule neuron precursors in the external granule layer of the cerebellum [9], or alternatively, from multipotent precursors in the ventricular zone of the cerebellum [10-12]. From a clinical point of view, current multimodal treatments include radical surgical resection followed by radiation and chemotherapy. While these treatments can improve the survival rate. MB remains incurable in about one third of these patients. The main cause of death is recurrence associated with tumor dissemination, at which point current therapeutic options have little efficacy [13]. These treatments are also toxic and can lead to long-term disabilities [14-16]. Consequently, there is a substantial need for novel, effective, low-toxicity therapies for children with medulloblastoma.

MB cells can also contain functionally important subsets of cells with stem-like properties that are uniquely able to propagate tumor growth [17,18]. Recent studies have demonstrated that both progenitors and stem cells can respond to the Sonic-Hedgehog (Shh) pathway and can serve as cells of origin for MBs [19].

Notch activity has been shown to regulate granule-cell progenitors from which MBs arise, with Notch2 gene copy numbers increased in 15% of MBs [12,20]. Persistent expression of bHLH HES1, the principal Notch-responsive gene, prevents both migration of neural progenitor cells out of the ventricular zone and expression of neuronal markers [21]. Mice lacking Hes1 show premature neurogenesis, seen as up-regulation of neural bHLH transcription factors, which results in major neural-tube defects [22]; progenitor cells derived from these mice have impaired self-renewing potential, with a commitment towards a neuronal lineage [23].

Significantly, expression of HES1 in MB has been associated with worse clinical outcome [24]. Of note, an interplay with Sonic-Hedgehog (Shh) in granular cell precursor development has been postulated [25], as has cross-talk with other pathways, e.g. the polycomb group gene BMI-1[26].

It is clear the need of new medical intervention for the cure of medulloblastoma and for the early diagnosis by histopathological markers and the detection of metastasis. The authors of this invention have been demonstrated that the expression of miRNA 199b-5p is lost in metastatic patients and they postulate a mechanism of regulation following epigenetic silencing through methylation processes occurring during carcinogenesis, identifying a new molecular marker for a poor-risk class in patients with MB. MiR-199b-5p overexpression blocks expression of several cancer stem-cell genes, impairs the engrafting potential of MB cells in the cerebellum of athymic/nude mice, and of particular interest, decreases the MB tumor stem-cell-like (CD133+) subpopulation of cells. For this reason miR-199b-5p can be used as anti-cancer therapy as well as a marker for determining the histophatological status of the tumors and for the knowledge of presence or absence of metastases. The authors within this invention have identified that the expression of miR-199-5p is lost in metastatic patients and postulated that this loss is due to mechanism of silencing during carcinogenesis. The authors have identified a new molecular marker for a specific class of medulloblastoma patients at low risk of recurrence and aggressive disease. Indeed miR-199-5p influence negatively the CD133+ cancer stem cells which in an xenograft orthotopic cerebellum cancer animal model show the impairment of growth and tumorigenesis in vivo, into cerebellum. For these above reasons miR-199b-5p can be used in an anti-cancer therapy as well as for diagnosis purposes as marker of the histopathological status of the tumors and for the correlation to presence or absence of metastases as predictive marker.

The authors in a screening of MB cell lines, found miR-199b-5p as regulator of the Notch signalling pathway through its targeting of the transcription factor HES1. Down regulation of HES1 expression by miR-199b-5p negatively regulates the proliferation rate and anchorage-independent growth of MB cells. MiR-199b-5p over-expression blocks expression of several cancer stem-cell genes, impairs the engrafting potential of MB cells in the cerebellum of athymic/nude mice, and of particular interest, decreases the MB stem-cell-like (CD133+) subpopulation of cells. In the analysis of 61 patients with MB, the expression of miR199b-5p in the non-metastatic cases was significantly higher than in the metastatic cases (P=0.001). Statistical correlation analyses following survival data for those patients with high expression levels of miR-199b-5p indicate a positive trend bettering order to define overall survival than for those miR-199b-5p low-expressing miR-199b-5p patients. These data showing the down-regulation of miR-199b-5p in metastatic MBs patients suggest a potential silencing mechanism through genetic or epigenetic modifications. Upon induction of de-methylation agents (example 5-aza-deoxycytidine), enhanced miR-199b-5p expression was observed in a panel of MB cell lines, supporting an epigenetic mechanism of regulation of miR-199b-5p. Furthermore, two medulloblastoma cell lines (Med8 and UV238) show a significative up-regulation phenomena of miR-199b-5p upon 5-aza-deoxycytidine treatment. The authors have created an induced xenograft orthotopic model into the mouse cerebellum cerebellum where previous infection of an adenovirus carrying miR-199b-5p on MB cells (Daoy cell line) and their injection into cerebellum of atimic/nude mice show a clinical benefit through miR199b-5p negative influence on tumor growth and especially on the subset of MB cancer-stem-cells-, providing further proofs of concept.

It is therefore specific object of the present invention an oligonucleotide sequence comprising or consisting of the following sequence:

(SEQ ID No: 1)
CCAGAGGACACCTCCACTCCGTCTACCCAGTGTTTAGACTATCTGTT

CAGGACTCCCAAATTGTACAGTAGTCTGCACATTGGTTAGGCTGGGC

TGGGTTAGACCCTCGG or comprising or consisting of the corresponding ribonucleotide sequence:

(SEQ ID No: 10)
CCAGAGGACACCUCCACUCCGUCUACCCAGUGUUUAGACUAUCUG

UUCAGGACUCCCAAAUUGUACAGUAGUCUGCACAUUGGUUAGGCU

GGGCUGGGUUAGACCCUCGG or comprising or consisting of a part of the SEQ ID No: 10:

(SEQ ID NO: 11)
CCCAGUGUUUAGACUAUCUGUUC for use in the treatment and/or prevention of tumours characterized by the expression of the gene CD133, chosen in the group consisting of medulloblastoma, lymphoma, glyoblastoma, colon carcinoma and mammary carcinoma.

Particularly, the bold sequence corresponds to mature miR-199b-5p sequence.

The above sequences can be carried in human by a viral vector (for the deoxy-ribonucleotide sequence), for example, adenoviral vector. SNALP technology (for the ribonucleotide sequence), LNA technology, or by modification of O-2-Methyl group through the link of a binding molecule of cholesterol, or using a linker $C_{1-7}$. Particularly, the adenoviral vector can be an AdV5 vector with map showed in FIGS. 15 e 16, of 6217 bp, CMV promoter and with XhoI/HindIII restriction sites cloned the comprised or composed sequence SEQ ID NO:1.

It is further object of this invention a diagnostic method in vitro for the evaluations of the histopathological status (stage) of the tumor or the definition of presence of absence of metastases through the investigation in a biological sample of the expression of the sequence comprised of consistent of the SEQ ID NO:1 together with one or more genes expressed in the cancer stem cell choose among CD133, c-myc, Nanog, Oct4, TCFL1, ZIC1, KLF5, HMGA1, HMGB3.

In particular, the tumors can be selected within the group consisting of colon carcinoma, medulloblastoma, glioblastoma, mammary carcinoma, lymphomas, and lung carcinoma; preferably colon carcinoma, medulloblastoma, glyoblastoma, mammary carcinoma and lymphoma; and most preferably colon carcinoma, medulloblastoma, glioblastoma, lymphoma.

According to an embodiment of the invention, the diagnostic method of the invention comprises the expression analyses of miR199b-5p and of CD-133 applied to the colon carcinoma, medulloblastoma and glioblastoma. According to a second embodiment, the diagnostic method comprises the expression analyses of miR199b-5p and of HMGA1 applied to the colon carcinoma, mammary carcinoma and lymphoma.

Preferably the detection of the expression of the sequence comprising or consisting of SEQ ID NO:1 can be evaluated by PCR Real-time with the following primers for amplification:

primer Forward:
(SEQ ID NO: 3)
CGGGAATTCCCAGAGGACACCTCCAC primer Reverse:
(SEQ ID NO: 4)
CGGCTCGAGCCGAGGGTCTAACCCAG and a couple of control primers to normalize the expression value of the sequence, for example, the following primers:

primer Forward:
(SEQ ID NO: 5)
GAA AAG CCT TGT TTG TGC TTG C primer Reverse:
(SEQ ID NO: 6)
GGG CCA TGC TAA TCT TCT CTG T.

As in an alternative mode, the detection of the expression of the sequence comprising or consisting of SEQ ID NO:1 comprises or consists of the following steps:
a) retrotranscription of the RNA; and b) expression of said sequence by TaqMan assay with the following primers and probe:

primer Forward:
(SEQ ID NO: 7)
AGGACACCTCCACTCCGTCTAC primer reverse:
(SEQ ID NO: 8)
GCCTAACCAATGTGCAGACTACTG probe:
(SEQ ID NO: 9)
CAGTGTTTAGACTATCTGTTCAGGACTCCCAAATTG According to a particular embodiment of the present invention, said one or more genes are detected by PCR Real Time by the amplification of at least one of the following sequences:

CD133:
(SEQ ID NO: 13)
CTATGTGGTACAGCCGCGTGATTTCCCAGAAGATACTTTGAGAAAATT
CTTACAGAAGGCATATGAATCCAA AATTGATTA c-myc:
(SEQ ID NO: 14)
AGGAGGAACAAGAAGATGAGGAAGAAATCGATGTT Nanog:
(SEQ ID NO: 15)
GCAAATGTCTTCTGCTGAGATGCCTCACACGGAGACTGTCTCTCCTC
TTCCTTCCTCCATGGATCTGCTTATTCAGGACAGC Oct4:
(SEQ ID NO: 16)
ACTGCAGCAGATCAGCCACATCGCCCAGCAGCTTGGGCTCGAGAAGG
ATGTGGTCCGAGTGTGGTTCTGTAACCGGCGCCA

TCFL1:
(SEQ ID NO: 17)
CCGCGGGACTATTTCGCCGAAGTGAGAAGGCCTCAGGACAGCGCG
TTCTTT

ZIC1:
(SEQ ID NO: 18)
CAGTTCGCTGCGCAAACACATGAAGGTCCACGAATCCTCCTCGCAGG
GCTC

KLF5:
(SEQ ID NO: 19)
GCATCCACTACTGCGATTACCCTGGTTGCACAAAAGTTTATACCAAGT
CTTCTCA

HMGA1:
(SEQ ID NO: 20)
AAAAACAAGGGTGCTGCCAAGACCCGGAAAACCACCACAACTCCAG
GAAGG

HMGB3:
(SEQ ID NO: 21)
TTTTCCAAGAAGTGCTCTGAGAGGTGGAAGACGATGTCCGGGAAAGA
GAAA;

using the following couples of amplification primers:

CD133:
Primer Forward:
(SEQ ID NO: 22)
CTATGTGGTACAGCCGCGTG

Primer Reverse:
(SEQ ID NO: 23)
TAATCAATTTTGGATTCATATGCCTTC c-myc
primer Forward:
(SEQ ID NO: 24)
ATGAGGAGACACCGCCCAC primer Reverse:
(SEQ ID NO: 25)
AACATCGATTTCTTCCTCATCTTCTT Nanog:
primer Forward:
(SEQ ID NO: 26)
GCAAATGTCTTCTGCTGAGATGC primer Reverse:
(SEQ ID NO: 27)
GCTGTCCTGAATAAGCAGATCCAT Oct4:
primer Forward:
(SEQ ID NO: 28)
ACTGCAGCAGATCAGCCACA primer Reverse:
(SEQ ID NO: 29)
TGGCGCCGGTTACAGAAC TCFL1:
primer Forward:
(SEQ ID NO: 30)
CCGCGGGACTATTTCGC primer Reverse:
(SEQ ID NO: 31)
AAAGAACGCGCTGTCCTGAG ZIC1:
primer Forward:
(SEQ ID NO: 32)
CAGTTCGCTGCGCAAACA primer Reverse:
(SEQ ID NO: 33)
GAGCCCTGCGAGGAGGAT KLF5:
primer Forward:
(SEQ ID NO: 34)
GCATCCACTACTGCGATTACCC primer Reverse:
(SEQ ID NO: 35)
TGAGAAGACTTGGTATAAACTTTTGTGC HMGA1:
primer Forward:
(SEQ ID NO: 36)
AAAAACAAGGGTGCTGCCAA primer Reverse:
(SEQ ID NO: 37)
CCTTCCTGGAGTTGTGGTGGT HMGB3:
primer Forward:
(SEQ ID NO: 38)
TTTTCCAAGAAGTGCTCTGAGAGG primer Reverse:
(SEQ ID NO: 39)
TTTCTCTTTCCCGGACATCG and using the following couples of primers for normalization of the expression of the following gene sequences:

primer forward:
(SEQ ID NO: 79)
CGT GCT GCT GAC CGA GG primer reverse:
(SEQ ID NO: 80)
GAA GGT CTC AAA CAT GAT CTG GGT Alternatively, said one or more genes can be detected by real time TaqMan for the amplification of at least one of the following sequences:

cd133
(SEQ ID NO: 40)
TCCACAGAAATTTACCTACATT
GGAAGAGTATGATTCATACTGGTGGCTGGGTGGCCTGGTCATCTGCT
CTCTGCTGACCC c myc
(SEQ ID NO: 41)
GCTGGATTTTTTTCGGGTAGTGGAAAACCAGCAGCCT
CCCGCGACGATGCCCCTCAACGTTAGCTTCACCAACAGGAACTA nanog:
(SEQ ID NO: 42)
CCGAAGAATAGCAATGGTGTGACGCAG
AAGGCCTCAGCACCTACCTACCCCAGCCTTTACTCTTCCTACCACCA
GGGATG oct 4:
(SEQ ID NO: 43)
AACCCGGAGGAGGTAGTCCTTTGTTACATGCATGAGTCAGTGAACAG
GGAATGGGTGAATGACATTTGTGGGTAGGTTATT tcfl1:
(SEQ ID NO: 44)
CCAAGGAAGAGAACGTTGACATAGAAGGCTCTTTGTGTTTTTCCTTGT
CTTTTGTCCTCAGACTTGATCCTGCTCCCTCGG zic 1:
(SEQ ID NO: 45)
CGCGCTCCGAGAATTTAAAGATCCACAAAAGGACGCACACAGGGAGA
AGCCCTTCAAGTGCGAGTTTGAGGGCTGTGACC KLF5:
(SEQ ID NO: 46)
TTTAACCCCACCTCCATCCTATGCTGCTACAATTGCTTCTAAACTGGC
AATTCACAATCCAAATTTACCCACCACCCTGCC HMGA1:
(SEQ ID NO: 47)
CCCCAGGCAGACCTTATATGAGACATGGGAGTCCCACCGTATTGTCC
AGGCTGGTCTCGAACTCCTGACCTCAAGCA HMGB3:
(SEQ ID NO: 48)
CGCTATGATCGGGAAATGAAGGATTATGGACCAGCTAAGGGAGGCAA
GAAGAAGAAGGATCCTAATGCTCCCAAAAGGCCA;

using the following primers and probes for amplification:

```
cd133
primer Forward:
                                      (SEQ ID NO: 49)
TCCACAGAAATTTACCTACATTGGAA primer Reverse:
                                      (SEQ ID NO: 50)
GGGTCAGCAGAGAGCAGATGA probe:
                                      (SEQ ID NO: 51)
AGTATGATTCATACTGGTGGCTGGGTGGC c myc:
primer forward:
                                      (SEQ ID NO: 52)
GCTGGATTTTTTTCGGGTAGTG primer reverse:
                                      (SEQ ID NO: 53)
TAGTTCCTGTTGGTGAAGCTAACG probe
                                      (SEQ ID NO: 54)
CAGCAGCCTCCCGCGACG nanog:
primer forward:
                                      (SEQ ID NO: 55)
CCGAAGAATAGCAATGGTGTGA primer reverse:
                                      (SEQ ID NO: 56)
GCATCCCTGGTGGTAGGAAGA probe:
                                      (SEQ ID NO: 57)
CAGCACCTACCTACCCCAGCCTTTA oct 4:
primer forward:
                                      (SEQ ID NO: 58)
AACCCGGAGGAGGTAGTCCTT primer reverse:
                                      (SEQ ID NO: 59)
AATAACCTACCCACAAATGTCATTCA probe:
                                      (SEQ ID NO: 60)
CATGCATGAGTCAGTGAACAGGGAA tcf11:
primer forward:
                                      (SEQ ID NO: 61)
CCAAGGAAGAGAACGTTGACATAG primer reverse:
                                      (SEQ ID NO: 62)
CCGAGGGAGCAGGATCAAG probe:
                                      (SEQ ID NO: 63)
AGGCTCTTTGTGTTTTTCCTTGTCTTTTGTCC zic 1:
primer forward:
                                      (SEQ ID NO: 64)
CGCGCTCCGAGAATTTAAAG primer reverse:
                                      (SEQ ID NO: 65)
CGGTCACAGCCCTCAAACTC probe:
                                      (SEQ ID NO: 66)
TCCACAAAAGGACGCACACAGGG KLF5:
Primer forward:
                                      (SEQ ID NO: 67)
TTTAACCCCACCTCCATCCTATG Primer reverse:
                                      (SEQ ID NO: 68)
GGCAGGGTGGTGGGTAAATT probe:
                                      (SEQ ID NO: 69)
TGCTTCTAAACTGGCAATTCACAATC HMGA1:
Primer forward:
                                      (SEQ ID NO: 70)
CCCCAGGCAGACCTTATATGAG Primer reverse:
                                      (SEQ ID NO: 71)
TGCTTGAGGTCAGGAGTTCGA probe:
                                      (SEQ ID NO: 72)
CATGGGAGTCCCACCGTATTGTCCA HMGB3:
primer forward:
                                      (SEQ ID NO: 73)
CGCTATGATCGGGAAATGAAG primer reverse:
                                      (SEQ ID NO: 74)
TGGCCTTTTGGGAGCATTAG probe:
                                      (SEQ ID NO: 75)
ATTATGGACCAGCTAAGGGAGGCAAG
``` and using the following couples of primers and probe to normalize the expression of the gene sequences:

```
primer Forward:
                                      (SEQ ID NO: 81)
GCCAACCGCGAGAAGATG primer Reverse:
                                      (SEQ ID NO: 82)
ACAGCCTGGATAGCAACGTACA probe:
                                      (SEQ ID NO: 83)
CCCAATCATGTTTGAGACCTTCAAC
```

It is further object of the present invention, a diagnostic kit in vitro to assess the histophatological stage of the tumour and the presence of the metastases by the detection, in a biological sample, through PCR real-time, of the expression of the sequence comprising or consisting of SEQ ID NO:1 and of one or more genes expressed in the cancer stem cells chosen among CD133, c-myc, Nanog, Oct4, TCFL1, ZIC1, KLF5, HMGA1, HMGB3 through real time TaqMan, said kit comprising or consist of:

a) the following primers of amplification of said sequence comprising or is consisting of SEQ ID NO:1:

```
primer Forward:
                                    (SEQ ID NO: 3)
CGGGAATTCCCAGAGGACACCTCCAC primer Reverse:
                                    (SEQ ID NO: 4)
CGGCTCGAGCCGAGGGTCTAACCCAG
``` b) a couple of control primers for the normalization of the expression value of said sequence;

c) one or more following couples of primers and corresponding probes to reveal the sequence of said one or more genes:

```
cd133
primer Forward:
                                    (SEQ ID NO: 49)
TCCACAGAAATTTACCTACATTGGAA primer Reverse:
                                    (SEQ ID NO: 50)
GGGTCAGCAGAGAGCAGATGA probeprobe:
                                    (SEQ ID NO: 51)
AGTATGATTCATACTGGTGGCTGGGTGGC c myc:
primer forward:
                                    (SEQ ID NO: 52)
GCTGGATTTTTTTCGGGTAGTG primer reverse:
                                    (SEQ ID NO: 53)
TAGTTCCTGTTGGTGAAGCTAACG probeprobeprobe
                                    (SEQ ID NO: 54)
CAGCAGCCTCCCGCGACG nanog:
primer forward:
                                    (SEQ ID NO: 55)
CCGAAGAATAGCAATGGTGTGA primer reverse:
                                    (SEQ ID NO: 56)
GCATCCCTGGTGGTAGGAAGA probeprobe:
                                    (SEQ ID NO: 57)
CAGCACCTACCTACCCCAGCCTTTA oct 4:
primer forward:
                                    (SEQ ID NO: 58)
AACCCGGAGGAGGTAGTCCTT primer reverse:
                                    (SEQ ID NO: 59)
AATAACCTACCCACAAATGTCATTCA probeprobe:
                                    (SEQ ID NO: 60)
CATGCATGAGTCAGTGAACAGGGAA tcfl1:
primer forward:
                                    (SEQ ID NO: 61)
CCAAGGAAGAGAACGTTGACATAG primer reverse:
                                    (SEQ ID NO: 62)
CCGAGGGAGCAGGATCAAG probeprobe:
                                    (SEQ ID NO: 63)
AGGCTCTTTGTGTTTTTCCTTGTCTTTTGTCC zic 1:
primer forward:
                                    (SEQ ID NO: 64)
CGCGCTCCGAGAATTTAAAG primer reverse:
                                    (SEQ ID NO: 65)
CGGTCACAGCCCTCAAACTC probeprobe:
                                    (SEQ ID NO: 66)
TCCACAAAAGGACGCACACAGGG KLF5:
Primer forward:
                                    (SEQ ID NO: 67)
TTTAACCCCACCTCCATCCTATG Primer reverse:
                                    (SEQ ID NO: 68)
GGCAGGGTGGTGGGTAAATT Probeprobe:
                                    (SEQ ID NO: 69)
TGCTTCTAAACTGGCAATTCACAATC HMGA1:
Primer forward:
                                    (SEQ ID NO: 70)
CCCCAGGCAGACCTTATATGAG Primer reverse:
                                    (SEQ ID NO: 71)
TGCTTGAGGTCAGGAGTTCGA Probeprobe:
                                    (SEQ ID NO: 72)
CATGGGAGTCCCACCGTATTGTCCA HMGB3:
primer forward:
                                    (SEQ ID NO: 73)
CGCTATGATCGGGAAATGAAG primer reverse:
                                    (SEQ ID NO: 74)
TGGCCTTTTGGGAGCATTAG probeprobe:
                                    (SEQ ID NO: 75)
ATTATGGACCAGCTAAGGGAGGCAAG
``` d) the following primers and probe to normalize the expression of the sequence of said genes:

```
primer Forward:
                                    (SEQ ID NO: 81)
GCCAACCGCGAGAAGATG primer Reverse:
                                    (SEQ ID NO: 82)
ACAGCCTGGATAGCAACGTACA probe:
                                    (SEQ ID NO: 83)
CCCAATCATGTTTGAGACCTTCAAC
```

In particular, the control primers presented in b) to normalize the expression of the sentience can be the following:

```
primer Forward:
                                    (SEQ ID NO: 5)
GAA AAG CCT TGT TTG TGC TTG C primer Reverse:
                                    (SEQ ID NO: 6)
GGG CCA TGC TAA TCT TCT CTG T
```

Furthermore, the invention concerns a diagnostic kit in vitro, to evaluate the histopathological stage of tumour and the presence of the metastases by detecting through TaqMan assay, in a biological sample, the expression of the sequence comprising or consisting of SEQ ID NO:1 and of one or more genes expressed in the cancer stem cells selected among CD133, c-myc, Nanog, Oct4, TCFL1, ZIC1, KLF5, HMGA1, HMGB3,
said diagnostic kit comprising and consisting of
a1) the following primers and probe for the detection of the expression of said sequence comprising or consisting of the SEQ ID NO:1

```
primer Forward:
                                    (SEQ ID NO: 7)
AGGACACCTCCACTCCGTCTAC primer reverse:
                                    (SEQ ID NO: 8)
GCCTAACCAATGTGCAGACTACTG probe:
                                    (SEQ ID NO: 9)
CAGTGTTTAGACTATCTGTTCAGGACTCCCAAATTG:
``` b1) one or more couples of the following primers and corresponding probes to the detection of the expression of said one or more genes:

```
cd133
primer Forward:
                                    (SEQ ID NO: 49)
TCCACAGAAATTTACCTACATTGGAA primer Reverse:
                                    (SEQ ID NO: 50)
GGGTCAGCAGAGAGCAGATGA probe:
                                    (SEQ ID NO: 51)
AGTATGATTCATACTGGTGGCTGGGTGGC c myc:
primer forward:
                                    (SEQ ID NO: 52)
GCTGGATTTTTTCGGGTAGTG primer reverse:
                                    (SEQ ID NO: 53)
TAGTTCCTGTTGGTGAAGCTAACG probeprobe
                                    (SEQ ID NO: 54)
CAGCAGCCTCCCGCGACG nanog:
primer forward:
                                    (SEQ ID NO: 55)
CCGAAGAATAGCAATGGTGTGA primer reverse:
                                    (SEQ ID NO: 56)
GCATCCCTGGTGGTAGGAAGA probe:
                                    (SEQ ID NO: 57)
CAGCACCTACCTACCCCAGCCTTTA oct 4:
primer forward:
                                    (SEQ ID NO: 58)
AACCCGGAGGAGGTAGTCCTT primer reverse:
                                    (SEQ ID NO: 59)
AATAACCTACCCACAAATGTCATTCA probe:
                                    (SEQ ID NO: 60)
CATGCATGAGTCAGTGAACAGGGAA tcfl1:
primer forward:
                                    (SEQ ID NO: 61)
CCAAGGAAGAGAACGTTGACATAG primer reverse:
                                    (SEQ ID NO: 62)
CCGAGGGAGCAGGATCAAG probe:
                                    (SEQ ID NO: 63)
AGGCTCTTTGTGTTTTTCCTTGTCTTTTGTCC zic 1:
primer forward:
                                    (SEQ ID NO: 64)
CGCGCTCCGAGAATTTAAAG primer reverse:
                                    (SEQ ID NO: 65)
CGGTCACAGCCCTCAAACTC probe:
                                    (SEQ ID NO: 66)
TCCACAAAAGGACGCACACAGGG KLF5:
Primer forward:
                                    (SEQ ID NO: 67)
TTTAACCCCACCTCCATCCTATG Primer reverse:
                                    (SEQ ID NO: 68)
GGCAGGGTGGTGGGTAAATT Probe:
                                    (SEQ ID NO: 69)
TGCTTCTAAACTGGCAATTCACAATC HMGA1:
Primer forward:
                                    (SEQ ID NO: 70)
CCCCAGGCAGACCTTATATGAG Primer reverse:
                                    (SEQ ID NO: 71)
TGCTTGAGGTCAGGAGTTCGA Probe:
                                    (SEQ ID NO: 72)
CATGGGAGTCCCACCGTATTGTCCA HMGB3:
primer forward:
                                    (SEQ ID NO: 73)
CGCTATGATCGGGAAATGAAG primer reverse:
                                    (SEQ ID NO: 74)
TGGCCTTTTGGGAGCATTAG probe:
                                    (SEQ ID NO: 75)
ATTATGGACCAGCTAAGGGAGGCAAG
``` c1) the following couple primers and probes for the normalization of the expression of the sequence of the above reported genes:

```
primer Forward:
                                    (SEQ ID NO: 81)
GCCAACCGCGAGAAGATG primer Reverse:
                                    (SEQ ID NO: 82)
ACAGCCTGGATAGCAACGTACA probe:
                                    (SEQ ID NO: 83)
CCCAATCATGTTTGAGACCTTCAAC
```

This invention will be described by way of illustration, but not in limitative way, by its favorite form of realization, with connection to the attached figures in which:

FIG. 1 shows the in-vitro function of miR199b-5b on proliferation and differentiation of Daoy MB cells.
A) Representative FACS analysis with propidium iodine showing a decrease in the percentages of cells in S phase and an increase in G0-G1 for the stable 199bSC1 clone. The absence of shoulder signals with the G0-G1 red peak in the 199bSC1 and 199bMC1 clones excludes apoptotic processes. B) Proliferation assays by 3-4,5-dimethylthiazol-2-yl-5-3-carboxymethoxyphenyl-2-4-sulfophenyl-2H-tetrazolium salt (MTS), showing decreased proliferation rates of the stable 199bSC1 clone (red triangles) and the 199bMC1 clone (green crosses), compared to the stable clone with empty vector alone (blue diamond). This effect of miR-199b-5p over-expression was reduced by 2-OM transfection (pink squares). The data shown are means±SD from two independent experiments, each carried out in triplicate. C) Representative mRNA expression of differentiation (e.g. MASH1, MATH3 and NEUROGENIN 2) and proliferation (e.g. c-MYC, CYCLIN D1) markers upon miR-199b-5p over-expression, as revealed by real-time PCR, comparing the stable 199bSC1 and 199bMC1 clones with wild-type cells. D) The stable 199bSC1 clone for miR-199b-5p shows impaired colony formation in soft agar assays. The plot shows colonies counted as means±SD from three independent experiments, each carried out in triplicate. E) Representative Western blot using anti-c-Myc and anti-cyclin D1 antibodies show these two proteins to be down-regulated in the stable 199bSC1 clone; see also the densitometric analysis in the right panel. F) As for E, showing GABRA6 and MATH3 proteins up-regulated after miR-199b expression, suggesting induction of differentiation. Anti-Laminin-β antibodies were used to normalized nuclear c-Myc and cyclin D1 protein expression. Anti-β-Actin antibodies were used to normalized cytoplasmic GABRA6 and MATH3 proteins expression.

FIG. 2 shows that the over-expression of miR-199b-5p decreases the CD133+ compartment of Daoy cells
A-F) Representative FACS analyses of the stable 199bSC1 (D) and 199bMC1 (F) clones showed a decrease in the percentage of cells that were positive for the stem cell marker CD133 (B); A, C and E are negative controls (no antibody).

FIG. 3 shows that the effects of miR-199b-5p over-expression are reversed by HES1 transfection.
A) Representative Western blot and densitometric analysis showing that the rescue of HES1 expression by over-expression of HES1 cDNA in the stable 199bSC1 clone restores cyclin D1 expression. B) Proliferation assay by 3-4,5-dimethylthiazol-2-yl-5-3-carboxymethoxyphenyl-2-4-sulfophenyl-2H-tetrazolium salt (MTS) showing increased proliferation rate of the stable 199bSC1 clone with HES1 expression (dark blue squares), compared to the stable 199bSC1 clone alone (light blue diamonds). The data shown are means±SD from two independent experiments, each carried out in triplicate. C) Representative mRNA expression of differentiation (e.g. MASH1, MATH3 and NEUROGENIN 2) and proliferation (e.g. c-MYC, CYCLIN D1) markers upon cell-rescue with HES1 in the stable 199bSC1 clone, comparing with wild-type cells, as revealed by real-time PCR. The expression of GABRA 6 and MAP2 are down-regulated in the rescue experiment. D) Representative FACS analysis of the HES1-expressing stable 199bSC1 clone shows an increase in the fraction of cells in S phase, and a decrease in G1, with respect to the stable 199bSC1 clone alone, E-H) The effect of miR-199b-5p expression on the SP of Daoy cells is reversed by HES1 re-expression. 199bSC1 stable clone was transfected with HES1 cDNA and a GFP-coding plasmid, then treated after 48 hours with Hoechst and verapamil (E-F) or Hoechst alone (G-H) and analyzed by FACS. The GFP-positive cells (P5 gate), panel E and G, were analysed for the presence of dye-excluding-cells (F-H, P6 gate). The untransfected GFP negative cells (P3 gate), were not analised.

FIG. 4 shows the decreased tumorigenicity of Daoy cells over-expressing miR-199b-5p.
A) Xenograft experiment over nine weeks, following s.c. injection of five mice with control Daoy cells (CTR side) and Daoy cells over-expressing miR-199b-5p (199b side). With CTR cells, tumors were detectable macroscopically in 5/5 mice; with over-expressing cells, in 3/5 mice. Total tumor volume difference between the CTR and 199b injected sides after nine weeks of growth was statistically significant, as indicated (means±SD). B) Photon emission of mouse #4 after nine weeks of tumor growth. The 199b side (199bLuc-1) had a consistently lower photon emission than the control side (Ctl-Luc-4). The comparisons of the tumor dimensions are also shown. C) When photon emission (see B) was converted to cell number; one of five mice showed no significant differences (means±SD) (two tailed unpaired t test). D) Photon emission of 3 mice injected in the fourth ventricle with respectively: 199bLuc-1, Ctl-Luc-4 infected with mock AdV5, and Ctl-Luc-4 infected with a miR-199b-5p AdV5. E) Entire brain of animal and site of injection (white arrow). Hematoxylin/eosin staining of cerebellum; black arrow, site of initiation of tumorigenesis. F) BLI of injected mice as for D, after one month of tumor growth. The differences between the groups are statistically significant. G) BLI of two selected mice showing development of tumor burden with Ctl-luc4-AdV5-Mock#7, and reduction with Ctl-luc4-AdV5-199b#3 over time (0-8 weeks). H) Hematoxylin-eosin staining of cerebellum from AdV5-Mock#2 and AdV5-199b#3 animals at 10 weeks post orthotopic injection, showing tumors cells surrounding external granular layer and within the IV ventricle (white star). In blue, DAPY staining, together with GFP detection, Magnification as indicated.

FIG. 5 shows the high-resolution molecular imaging of xenografted MB cells injected into the cerebellum.
PET-CT fusion images of AdV5-Mock#7 (A) and AdV5-199b#5 (B) mice at 12 weeks from surgery and injection, with 3D volume rendering and simultaneous display of areas of FLT uptake (blue-green, white arrows). A wider bone defect in the occipito-parietal portion of the skull is apparent in the AdV5-Mock#7 mouse. Below: table of measurements (cm3) of tumor mass undertaken with PET-CT acquisition (as described in Supplementary Material).

FIG. 6 shows the expression levels of miR199b in human cerebellum and in tumors, and the correlation with prognosis
A) Box-plot of expression levels of miR-199b-5p in healthy human cerebella in the two age ranges indicated. MiR-199b-

5p showed higher expression in explants from younger controls (Mann-Whitney test, P 0.006). B) MiR-199b-5p highly expressing cases are mostly M0 P=0.001 (Pearson Chi-Square test). C) Kaplan-Meier survival estimates comparing patients with low versus high (relative to median) levels of miR-199b-5p expression (45 patients with available follow-up data). D) MiR-199b-5p expression by real-time PCR in a panel of five MB cell lines untreated or treated with 5-Aza-C (DAC−/+); the de-methylation induced miR-199b-5p transcription in two cell lines: med8a and uw228.

E) The interplay between miR-199b-5p and the Notch pathway.

M0 and M+ patients show different expression levels of miR-199b-5p, which could be driven by an epigenetic mechanism. Left side: Under conditions of induced miR-199b-5p expression (1), the levels of HES1 decrease, relieving the inhibition on the neurogenic bHLHs (2). This in turn promotes a neurogenic programme and a decrease in proliferation, SP and CD133+ cells (3). Right side: Under conditions of low miR-199b-5p expression, the levels of HES1 are higher (1), repressing the pro-neural bHLH genes, with a consequent increase in proliferation, SP and an enlargement of the CD133+ compartment (4).

Figure 9:
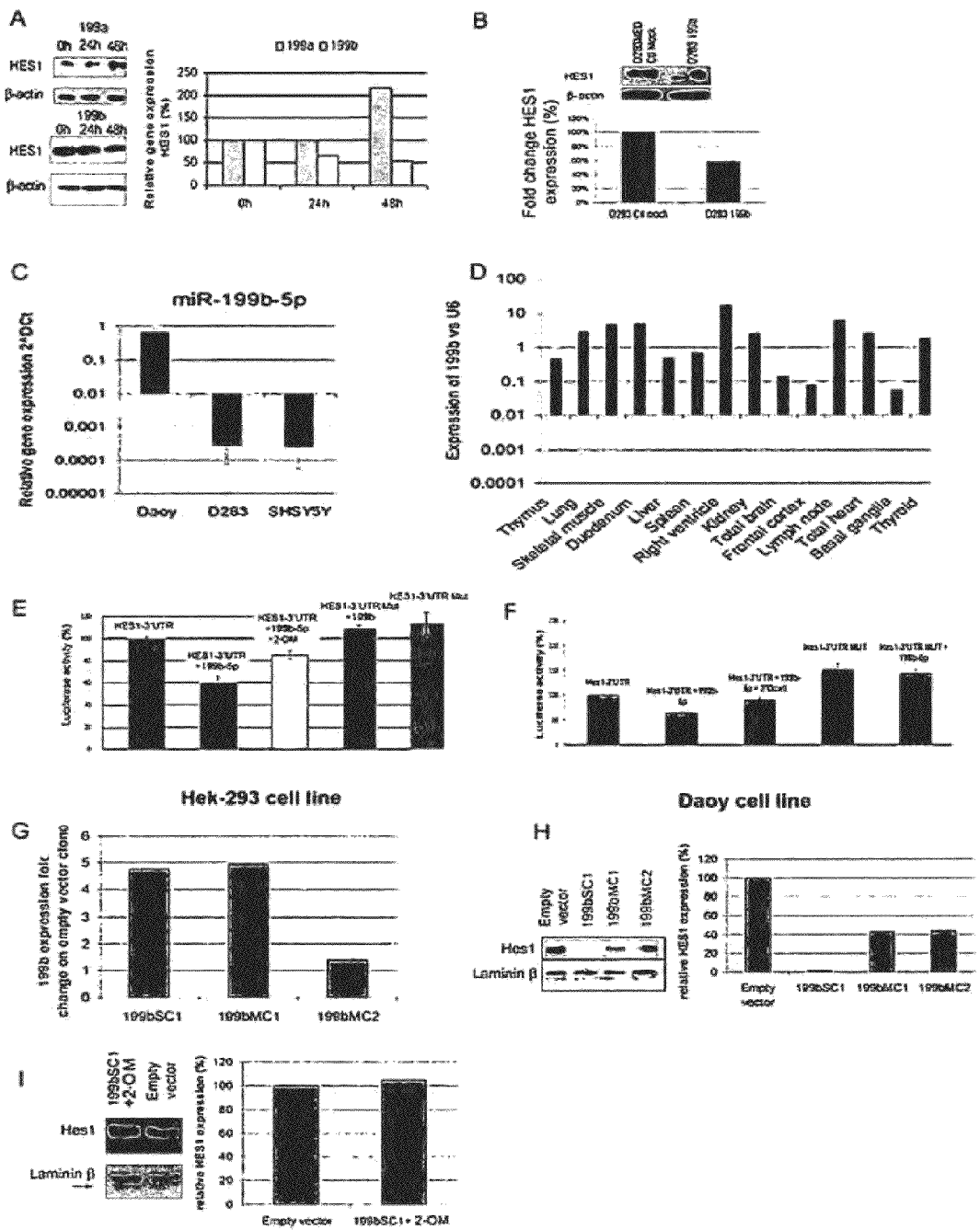

FIG. 9. A) Representative Western blots from transient transfection of HEK293 cells with expression constructs for miR-199b-5p and miR-199a. MiR-199b-5p over-expression lowered the levels of the endogenous HES1 protein; in contrast, miR-199a induced an increase in HES1 levels 48 h after transfection. Right: Quantification through densitometry analyses. B) Representative Western blot from transient transfection of D283 cells with the expression construct for miR-199b-5p and using an empty vector, Again, miR-199b-5p over-expression lowered the levels of the endogenous HES1 protein. Below a quantification through densitometric analyses. C) D283 and SH-SY5Y cells express similar levels of miR-199b-5p and miR-124a, with the latter known to be preferentially expressed in the central nervous system. In contrast, the D283Med cells showed considerably lower levels of miR-199b-5p. The data shown are means±SD from two independent experiments, each carried out in triplicate. D) Representative MiR-199b-5p expression profiles across a panel of human tissues (Ambion); miR-199b-5p was expressed to different degrees, with relatively high expression in the duodenum, lymph nodes, lung, skeletal muscle, right ventricle (highest), kidney, total heart and thyroid.

MiR-199b-5p effects on the 3'UTR of its putative target gene, HES1.

E-F) Luciferase activity from a reporter vector containing wild-type HES1 3'UTR and HES1 3'UTR mutated in the miR-199b binding site, co-transfected or not with an expression vector for miR-199b-5p. The luciferase from the wild-type 3'UTR activity was reduced by 50% with miR-199b-5p expression, while 2'-O-methyl-oligoribonucleotide (2-OM; 400 nM) blocks this effect. There is no effect with the miR-199b-5p together with the HES1 3'UTR mutated in the binding site. A representative experiment is shown where the data are means±SD from three replicates in HEK293 and Daoy cell lines respectively. G-I) Pre-miR-199 was cloned and transfected into Daoy cells, and three stable clones were evaluated for HES1 expression by qRT PCR and Western blotting. There was a significant decrease in HES1 protein levels, as revealed using an anti-HES1 polyclonal antibody; the decrease was also revealed by densitometry analysis (G; right panel) H) A 2'-O-methyl-oligoribonucleotide (2-OM) directed against miR-199b-5p was transfected into the stable 199bSC1 clone, with a representative Western blot and the quantification by densitometric analysis showing restored HES1 expression. The quantification data shown are means±SD from two independent experiments, each carried out in triplicate.

Figure 10:
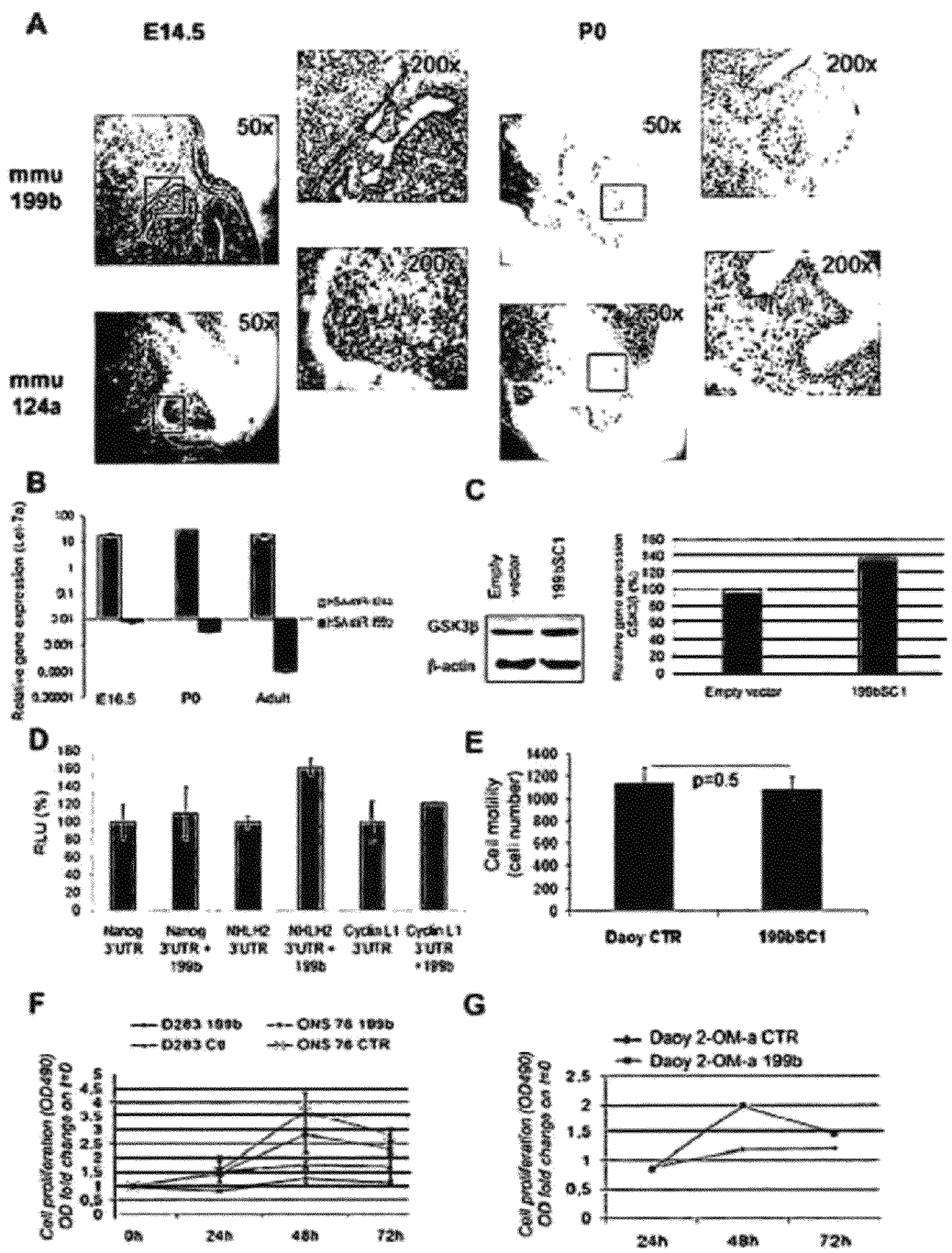

FIG. 10. Mmu-miR-199b expression in mouse embryonic cerebellum and regulation of other potential targets by human miR-199b-5p.

A) Mmu-miR-199b in situ mRNA expression is detectable at E14.5 and in newborn mouse (p0) cerebellum. The staining was diffuse, and in all areas of, the cerebellum; expression decreased from E14.5 to p0. Mmu-miR-124a (a brain specific miRNAs) was used as control. Left: magnification, 50×; Right: magnification, 200×. B) Quantification of decrease in mmu-miR-199b expression during mouse development and differentiation of the cerebellum. The levels of expression of mature miR-199b-5p are given relative to let-7A, with the data shown as means±SD from two independent experiments, each carried out in triplicates C) Representative Western blot showing the protein levels of GSK3-β which is predicted to be a target, in the higher expressing miR-199b-5p stable clone. GSK3-β levels were not down-regulated, and were instead slightly increased, as is clear from the quantification by densitometric analysis shown in the right panel, where the data shown are means±SD from two independent experiments, each carried out in triplicate D) MiR-199b-5p is predicted to bind other UTRs (see Supplementary Table S1). When miR-199b-5p over-expression in Daoy cells was examined for down-regulation of productive translation from a reporter gene carrying the full-length 3'UTRs indicated, none of them were seen to be affected. The data shown are means±SD from two independent experiments, each carried out in triplicate. E) Cell motility assays comparing the 199bSC1 cell line with the Daoy empty vector CTR (control) line using a Boyden chamber system (0.5% FBS as chemoattractant). The higher motility cells were fixed and hematoxylin stained and counted under the microscope. The data shown are means±SD from two independent experiments, each carried out in triplicate, and they indicate no differences between control (CTR) and the 199bSC1 cell line. F) Proliferation assay (MTS) of D283MED and ONS76 cells over-expressing miR-199b-5p after transient transfections, as indicated. The D283MED cells transfected with 199b-5p (blue diamonds) show appreciable reduction in cell proliferation, as compared to the control, empty vector, transfection (green triangles). ONS76 cells show a higher proliferation rate that is nonetheless affected by the 199b-5p transfectant (compare orange crosses of empty vector transfection to purple squares). The data shown are means±SD from two independent experiments, each carried out in triplicate G) Silencing of endogenous expression of miR-199b-5p via transfection of a 2-O-methyl oligoribonucleotide antisense (2-OM-a) leads to an increase in Daoy cells proliferation, probably relieving the control of endogenous miR-199b-5p on HES1 3'UTR. The data shown are means±SD from two independent experiments, each carried out in triplicate.

Figure 11:
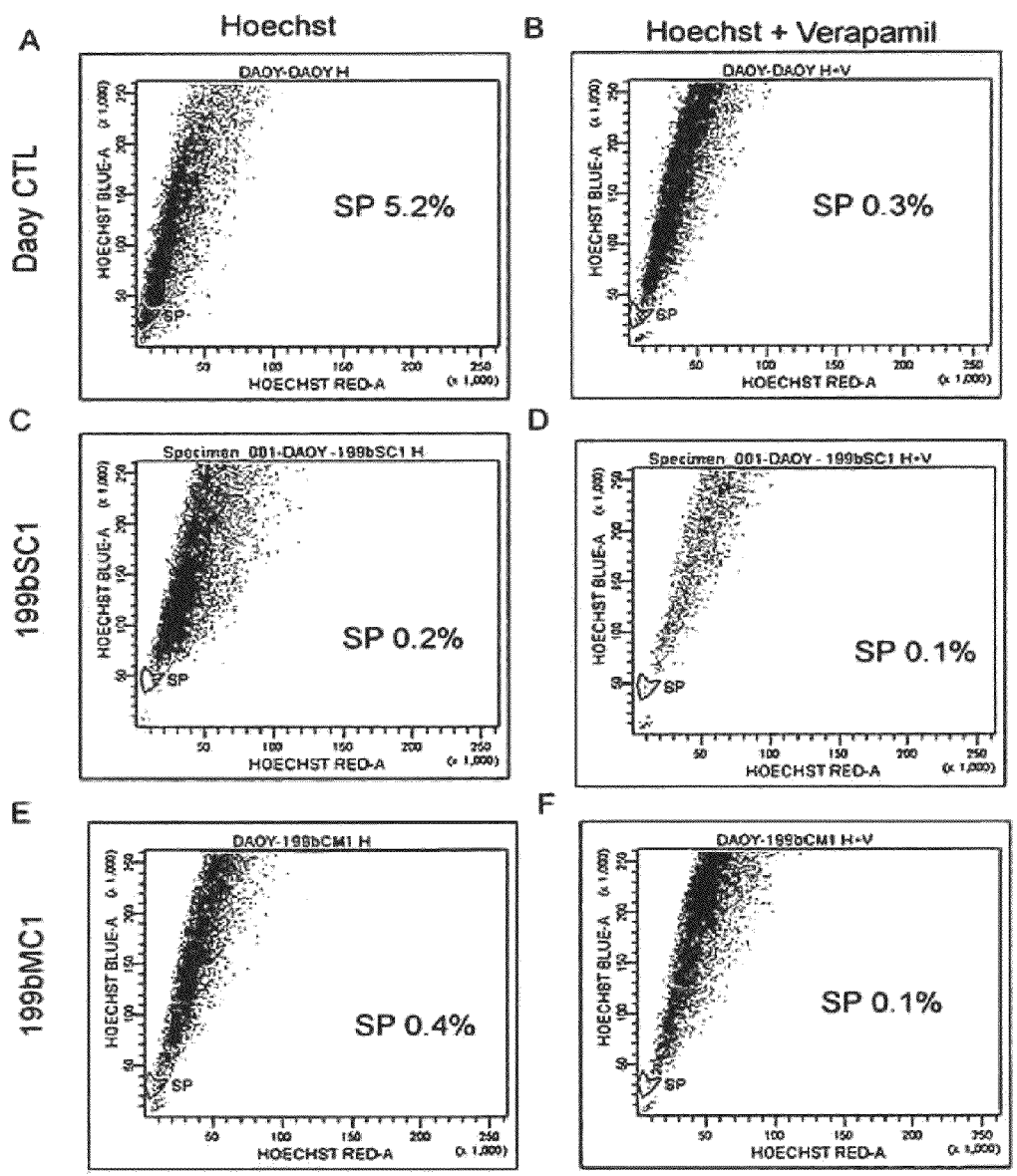

FIG. 11. FACS analysis for the role of miR-199b-5p on the Daoy cell side population.

A, C, E) Decrease in the SP cells of the Daoy 199bSC1 stable clone, as determined by Hoechst 33342 staining. B, D, F) Addition of verapamil to force dye incorporation also in the SP cells. The Daoy cells showed a 5.2% fraction of SP cells, while the stable 199bSC1 and 199bMC1 clones over-expressing miR-199b-5p do not show significant levels of SP cells (0.2%, 0.4%, respectively).

Figure 12:
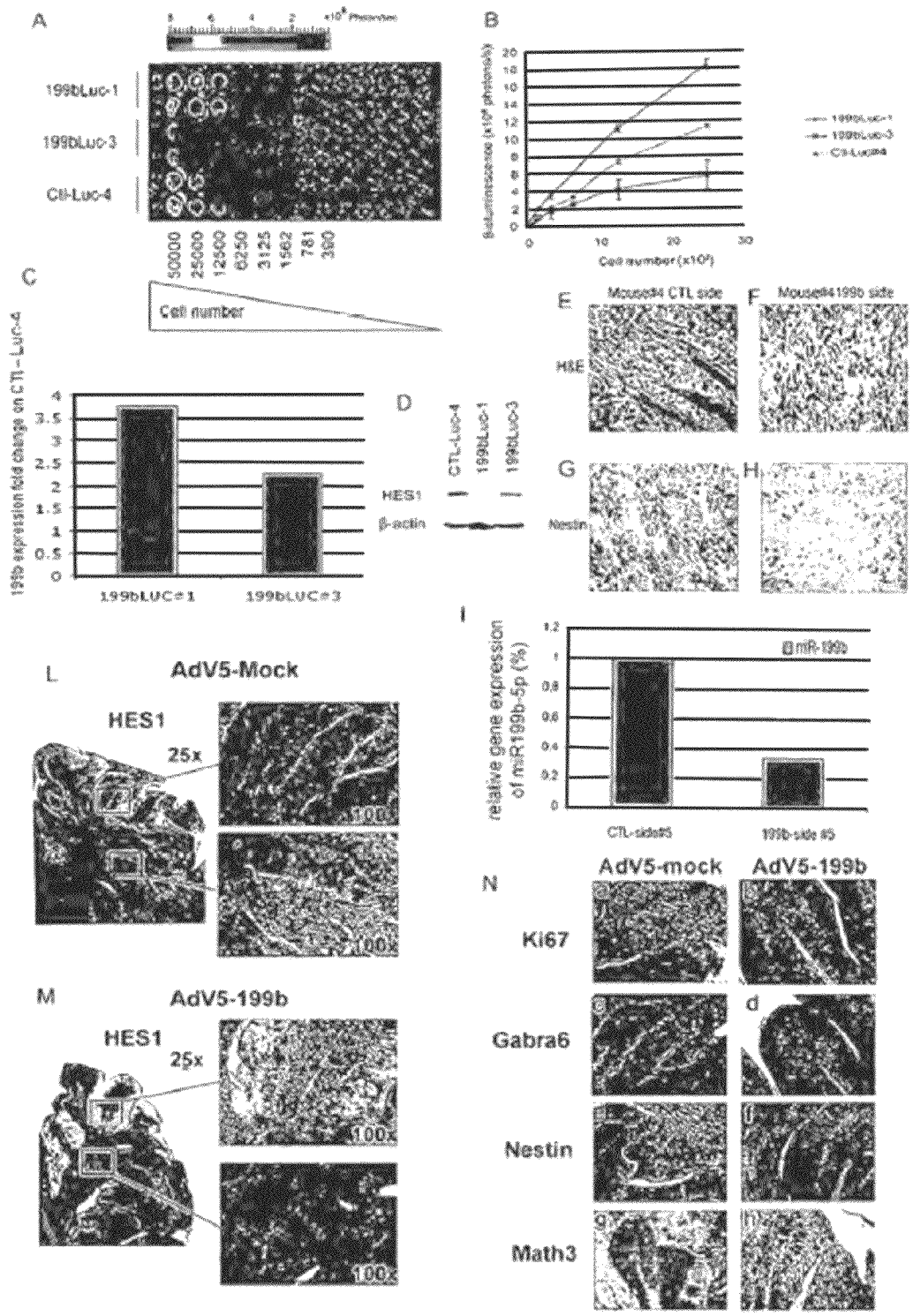

FIG. 12. Creation of bioluminescent Daoy cells over-expressing miR-199b-5p for in-vivo studies.

The Daoy stable clone with the empty vector (Ctl) and the Daoy stable clone over-expressing miR-199b-5p (199b) were transfected with a luciferase expression vector (Luc), generating, respectively, the Ctl-Luc#4 clone, and the 199bLuc-1 and 199b-Luc-3 clones. These were all evaluated for their expression of bioluminescence when incubated with the enzyme substrate, luciferin. A) Light emission of serial dilutions of the cells indicated in a microplate. The bioluminescence signal was acquired by an IVIS 200 Imaging System (Xenogen Corp. Alameda, Calif.). B) Correlation between cell number and photon emission. The 199b-Luc1 and Ctl-Luc#4 clones where used for the in-vivo studies, with the data shown as means±SD from two independent experiments C) Representative data of the expression of miR-199b-5p in the luciferase clones, relative to the luciferase clone carrying the empty vector. D) Representative immunoblot analysis showing lowered expression of HES1 in the 199b-Luc clones, compared to the empty-vector clone. E, F) Hematoxylin and eosin staining of xenografts derived from mouse #4: the control-injected side shows the xenograft infiltrating the muscle tissue, while the 199b-injected side does not. G, H) Nestin is a marker of neuroblasts, and its expression correlates with a lesser differentiated state: the xenograft from the mouse #4 199b-injected side shows a decrease in Nestin positivity. Nestin staining was performed by immunohistochemistry with a polyclonal antibody (Abcam). Magnification, 100×. I) Representative gene expression levels of the transgene miR-199b-5p in the tumor explant from mouse #5. The overexpression of miR-199b-5p was lost. L, M, N) Immunohistochemistry with anti-HES1, anti-KI67, anti-Gabra6, anti-Nestin, anti-Math3 antibodies and hematoxylin staining of the xenografts from the cerebellum of AdV5-Mock and AdV5-199b mice. Significant expression of Hes1, Ki67, Nestin and Math3 proteins is seen in the AdV5-Mock cerebellum tumoral tissue, while very low Hes1, Ki67 Nestin and Math3 expression is seen in the AdV5-199b tumor cells in the cerebellum. Differences of expression of Gabra6 are barely observed between in the AdV5-Mock cerebellum tumoral tissue and AdV5-199b mice. Left: magnification, 25×; Right: magnification, 100×.

Figure 13:
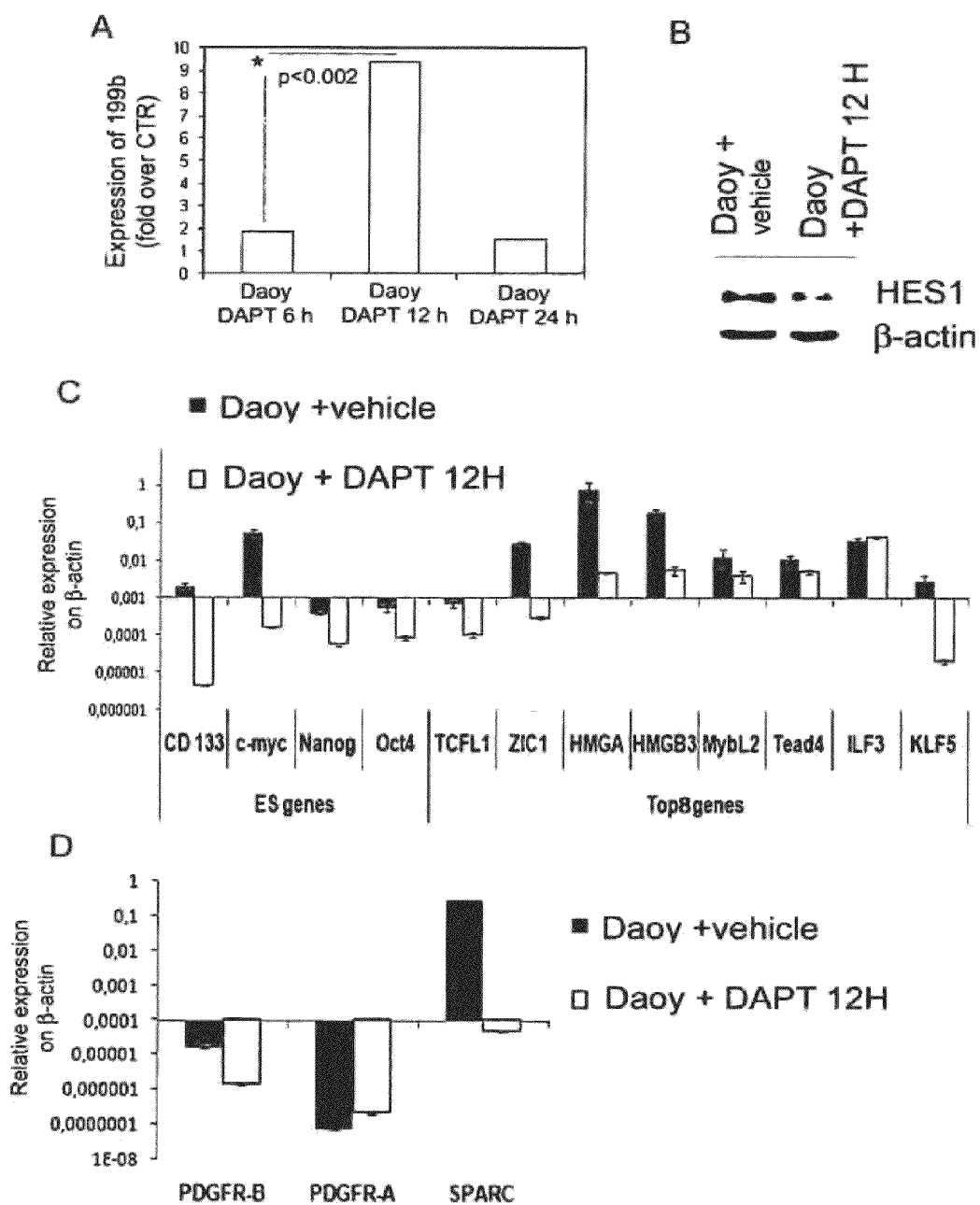

FIG. 13. Over-expression of endogenous miR199b upon DAPT treatment induces down-regulation of genes involved to embryonic stem cells and cancer stem cells in the Daoy cell line.

A) Representative data of a time course experiment of DAPT treatment of Daoy cell lines (6 h, 12 h, 24 h) with media supplemented and replaced every 4 h, and fold of expression of miR199b determined using quantitive real time detection, relative to time 0. B) Representative Western blot showing HES1 down-regulation after 12 h of induction of DAPT in the Daoy cell line. C) Relative gene expression levels of CD133, c-Myc Oct4, KFL5, Nanog, TCF7L1, HMGA1, HMGB3, ZIC1, MYBL2, TEAD4, ILF3 in the Daoy cell line without and with treatment with DAPT for 12 h. D) Relative gene expression of PDGFR-A, PDGFR-B and SPARC in the Daoy cell line without and with treatment with DAPT for 12 h. The primers used and their DDct values of relative expression using real-time cDNA quantitative detection, are listed in Supplementary Table S3.

Figure 14:
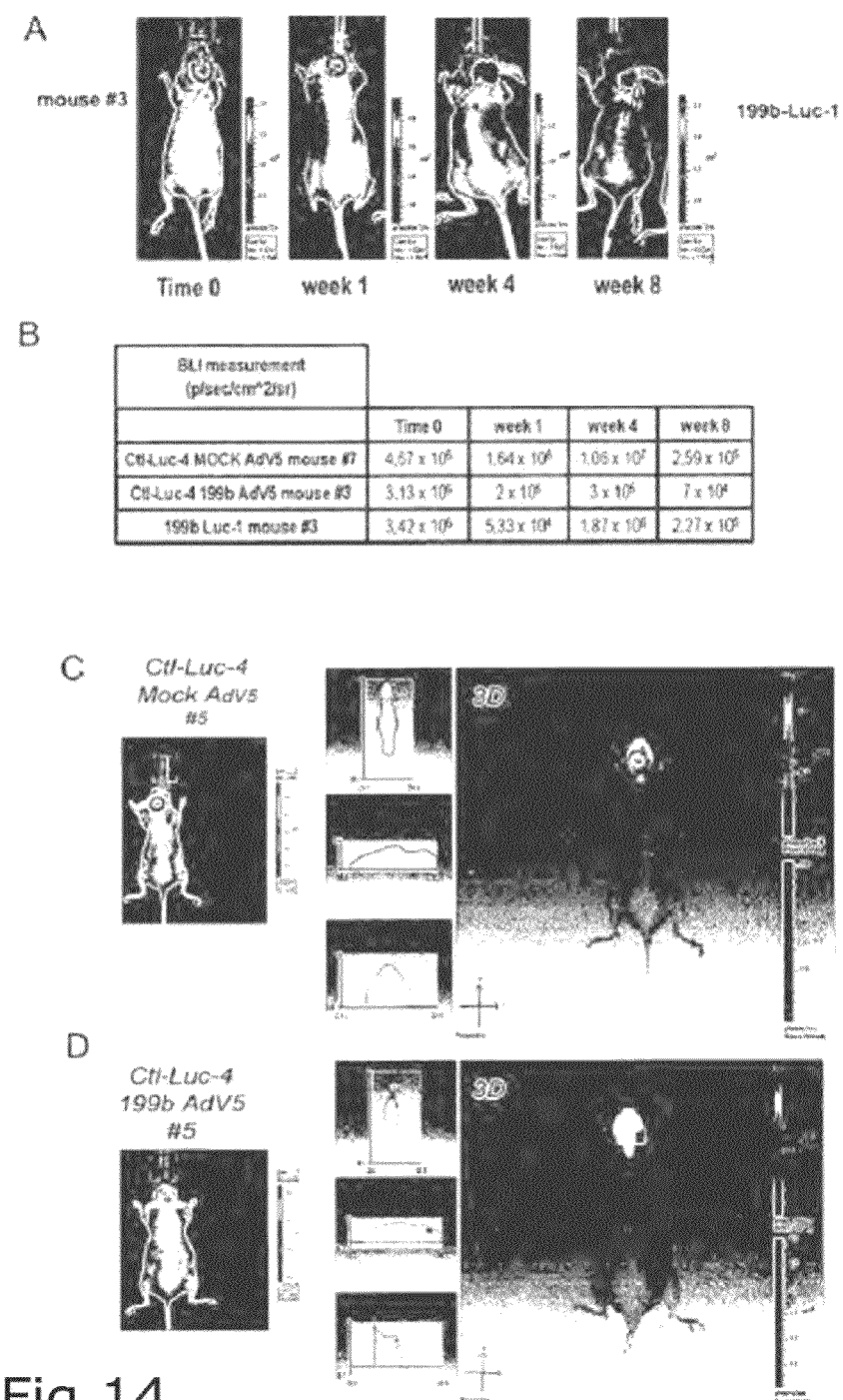

FIG. 14. Mir-199-b-5p interferes with the engraftment potential of Daoy cells injected into mouse cerebellum.

A) In-vivo bioluminescence analyses using IVIS 3D of 199b-Luc1 mouse xenografted with Daoy Luc1 cell line overexpressing miR-199b by stable clone analyses. (see mouse #3; see additional data in FIG. 4F, main text). The mouse was scanned once a week for a total of 8 weeks. B) BLI measurements (photon/sec/cm−2) from mice carrying cells infected with ADV5-199b show reductions to week 8. C) Images taken by IVIS Spectrum at 560 nm and 660 nm to generate the topography of the subject. Clt-Luc-4 AdV5-Mock xenografted mice shown on a 3D axis (x,y,z), with the extension of the tumor burden shown in comparison with a digital mouse atlas that enabled the display of the 3D skeleton and organs on the 3D reconstruction, using Living Images software. D) As described above, analyses are taken on Ctl-luc AdV5 199b xenografted mice. The video of 3D images are attached as separated files.

Figure 15:
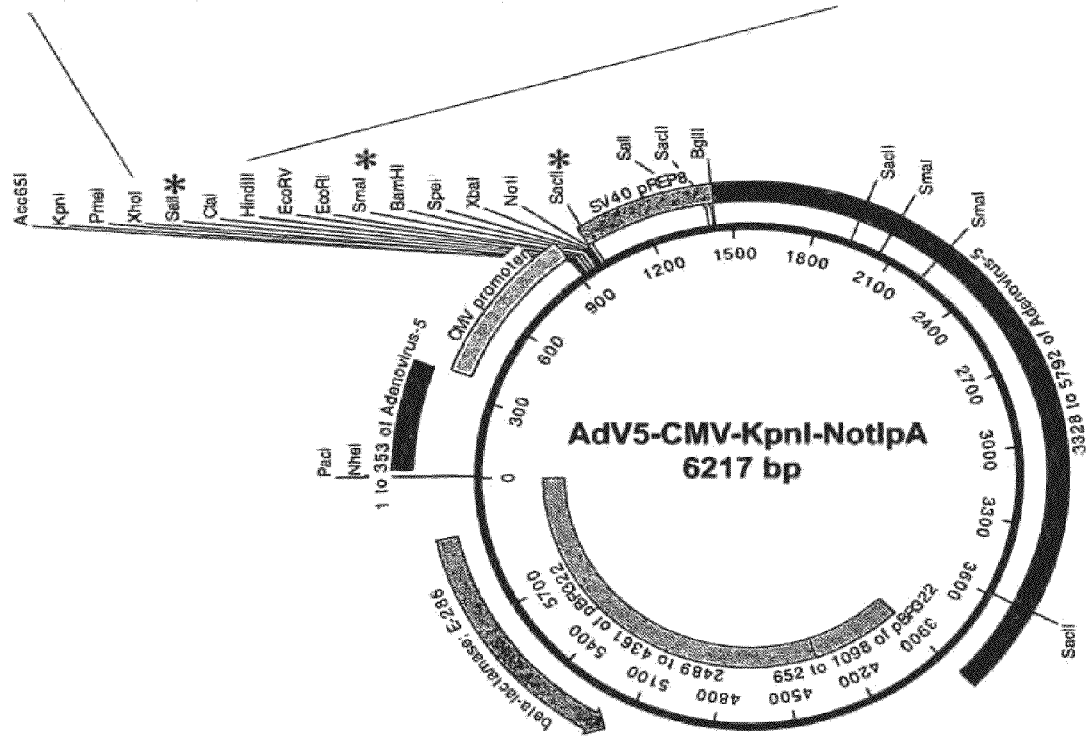

FIG. 15 Map of adenoviral vector AdV5-CMV-KpnI-NotIpA 6217 bp with the sequence SEQ ID NO:1.

FIG. 16 sequence of the vector AdV5-CMV-KpnI-NotIpA 6217 bp (SEQ ID NO:2).

Figure 17:
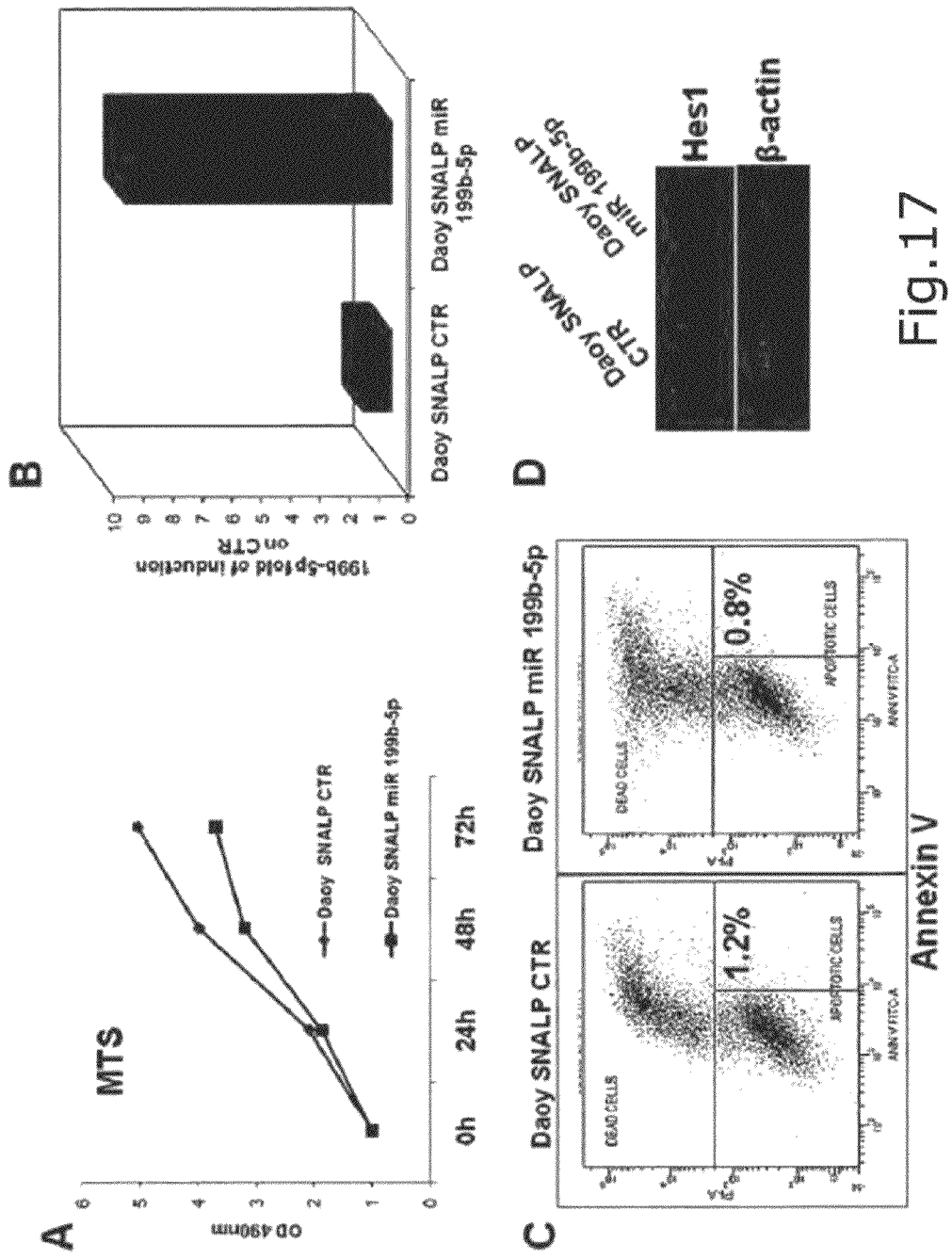

FIG. 17: A) Proliferation assay (MTS) of the human MB cell line Daoy at 0, 24, 48 e 72 h after the treatment with control SNALP (Daoy SNALP CTR) and with the SNALP miR199b-5p (Daoy SNALP 199b); B) Expression of miR199b-5p by real time PCR in the human MB cell line Daoy after 72 h of the treatment with the control SNALP (Daoy SNALP CTR) and with the SNALP miR199b-5p (Daoy SNALP 199b); C) Apoptosis assay with Annexin V in the human MB cell line Daoy after 72 h of the treatment with the control SNALP (Daoy SNALP CTR) and with the SNALP miR199b-5p (Daoy SNALP 199b); D) Expression of Hes1 by western blotting in the human MB cell line Daoy after 72 h of the treatment with the control SNALP (Daoy SNALP CTR) and with the SNALP miR 199b-5p (Daoy SNALP 199b).

Figure 18:
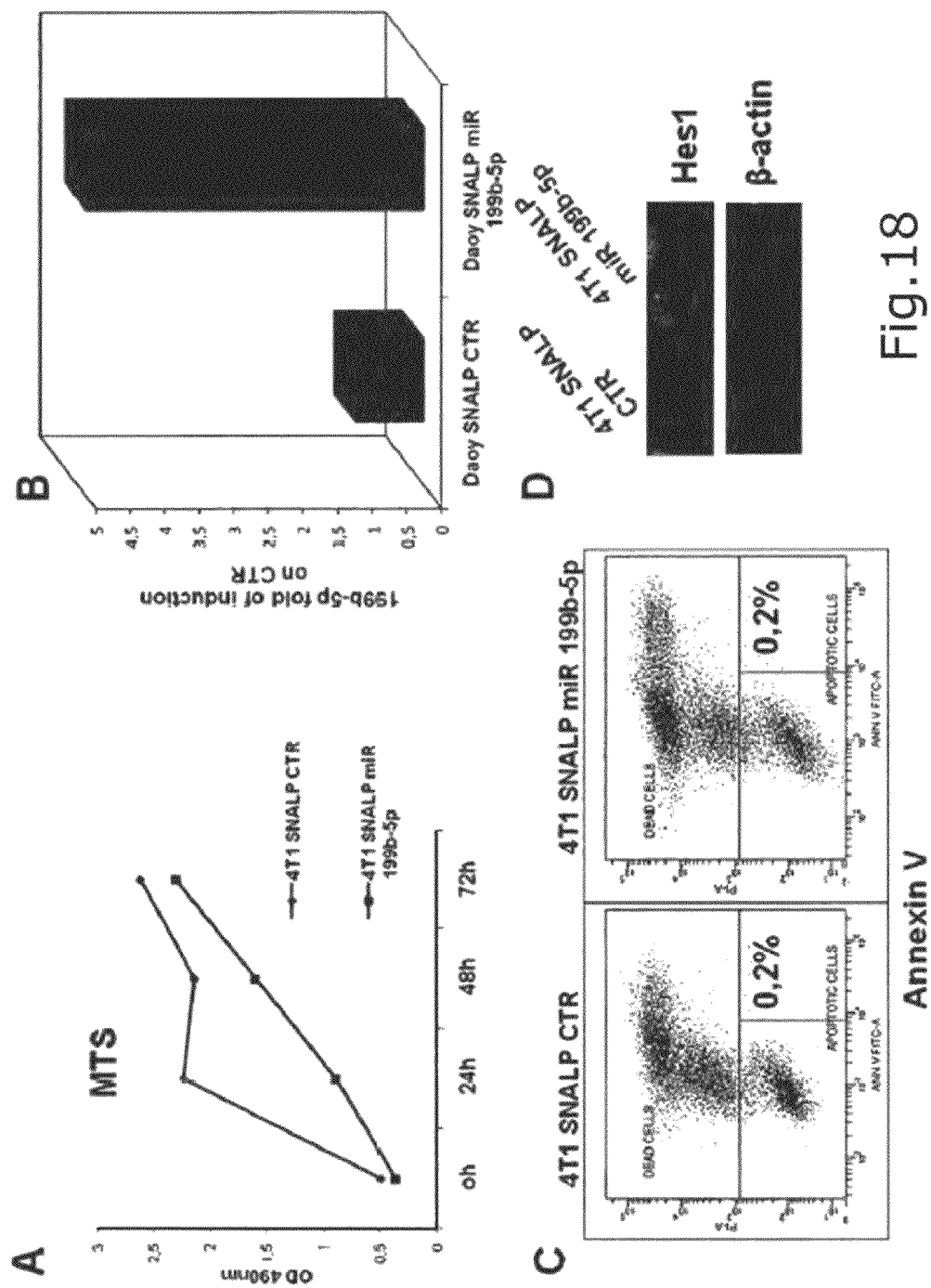

FIG. 18: A) Proliferation assay (MTS) in the human colon carcinoma cell line at 0, 24, 48 e 72 h after the treatment with the control SNALP (4T1 SNALP CTR) and with the SNALP miR199b-5p (4T1 SNALP 199b); B) Expression of the miR199b-5p by Real time PCR in the murine breast carcinoma cell line 4T1 after the treatment with the control SNALP (4T1 SNALP CTR) and with the SNALP miR199b-5p (4T1 SNALP 199b); C) Apoptosis assay with Annexin V in the murine breast carcinoma cell line 4T1 after 72 h of the treatment with the control SNALP (4T1 SNALP CTR) and with the SNALP miR199b-5p (4T1 SNALP 199b); D) Western blotting analysis of Hes1 after the treatment with the control SNALP and with the SNALP miR199b-5p.

Figure 19:
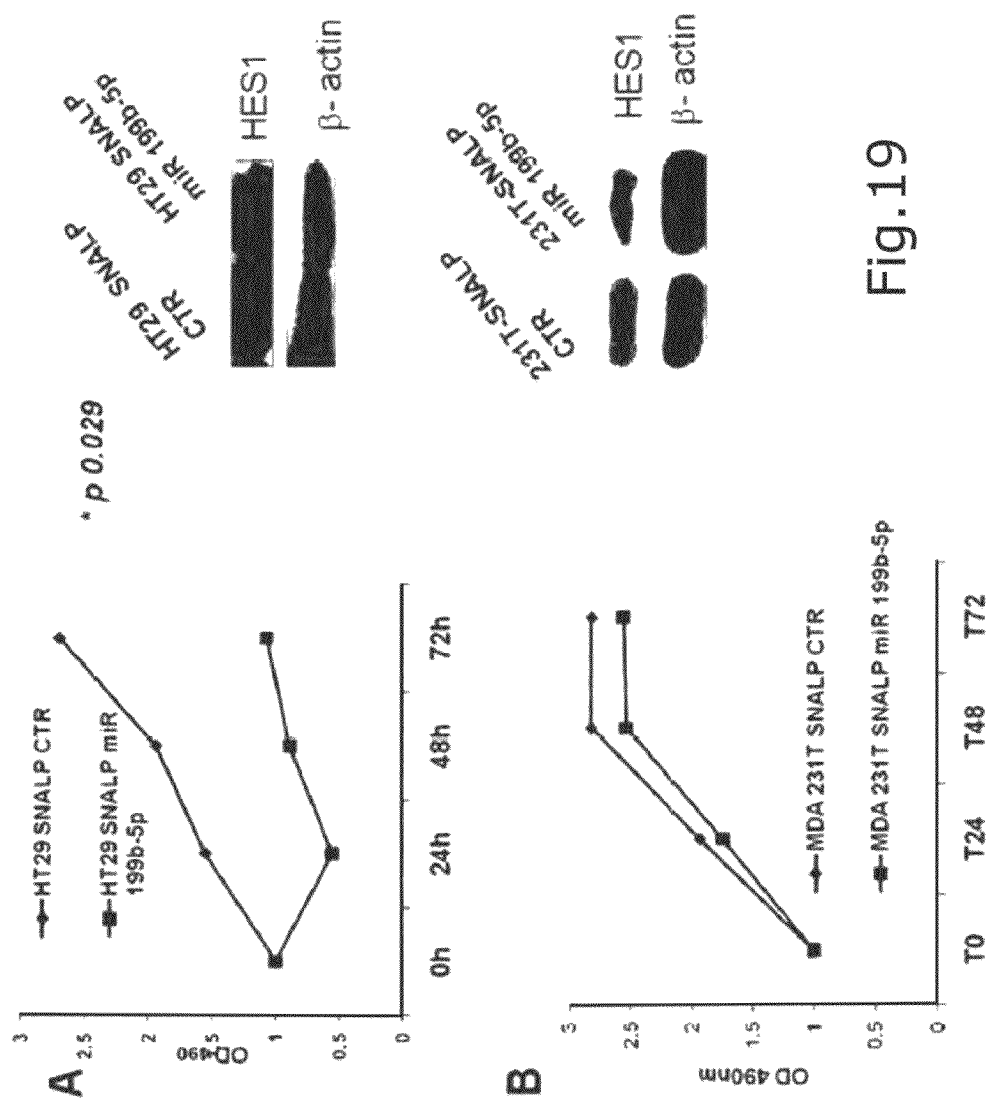

FIG. 19: A) Proliferation assay (MTS) in the human colon carcinoma cell line at 0, 24, 48 e 72 h after the treatment with the control SNALP (HT29 SNALP CTR) and with the SNALP miR 199b-5p (HT29 SNALP 199b); in the side the western blotting analysis of Hes1 after the treatment with the control SNALP (HT29 SNALP CTR) and with the SNALP miR 199b-5p (HT29 SNALP 199b); B) Proliferation assay (MTS) in the human breast carcinoma MDA-231T at 0, 24, 48 e 72 h after the treatment with control SNALP (MDA-231T SNALP CTR) and with the SNALP miR 199b-5p (MDA-231T SNALP 199b). In the side the western blotting analysis of Hes1 after the treatment with the control SNALP and with the SNALP miR 199b-5p.

Figure 20:
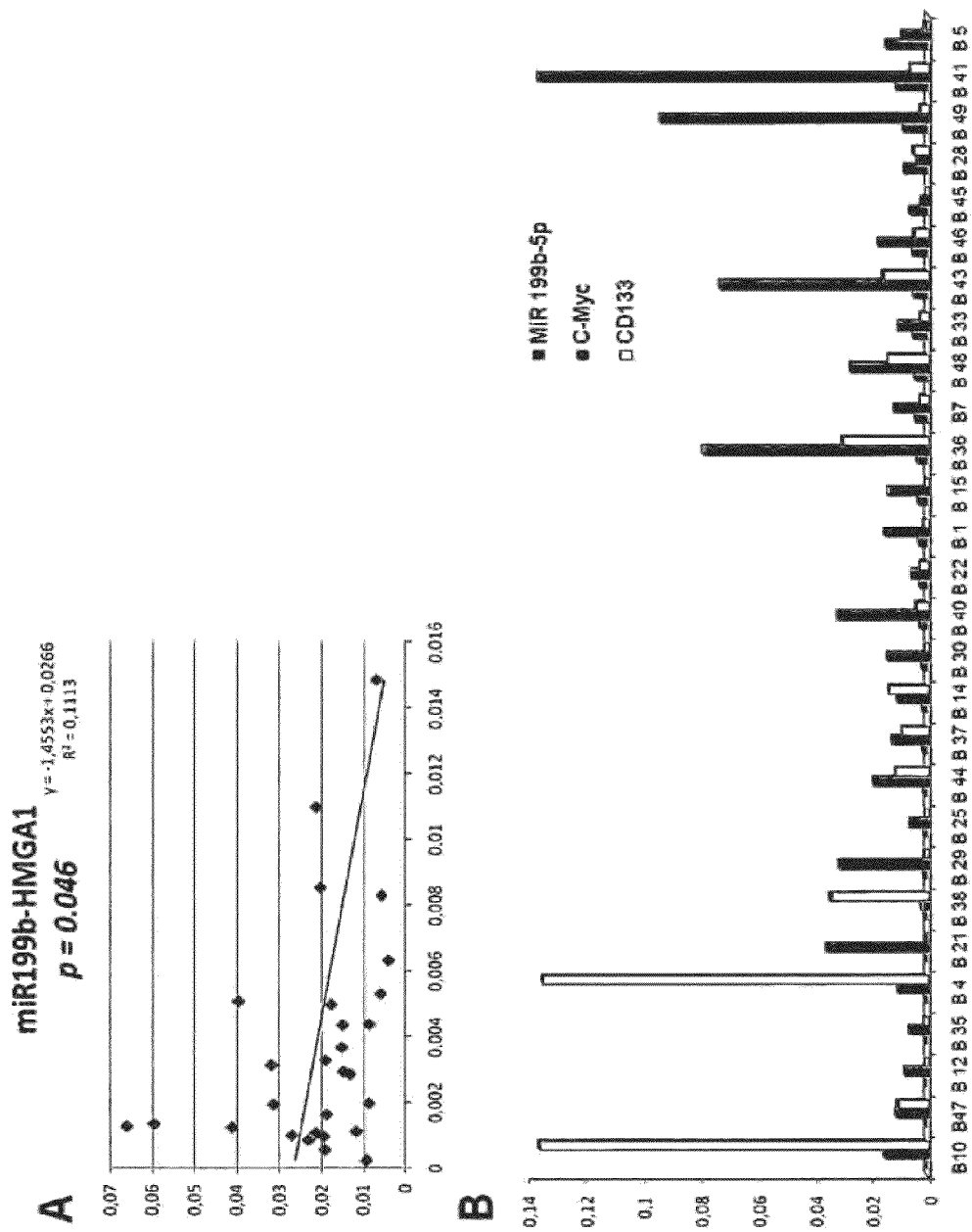

FIG. 20: A) Inversion correlation of the miR199b-5p expression and the gene HMGA1 (p=0.046) by real time PCR in 28 breast carcinoma tissues by Pearson test. B) Expression of miR199b-5p and of the genes c-myc and CD133 in 28 breast carcinoma tissues by real time PCR.

Figure 21:
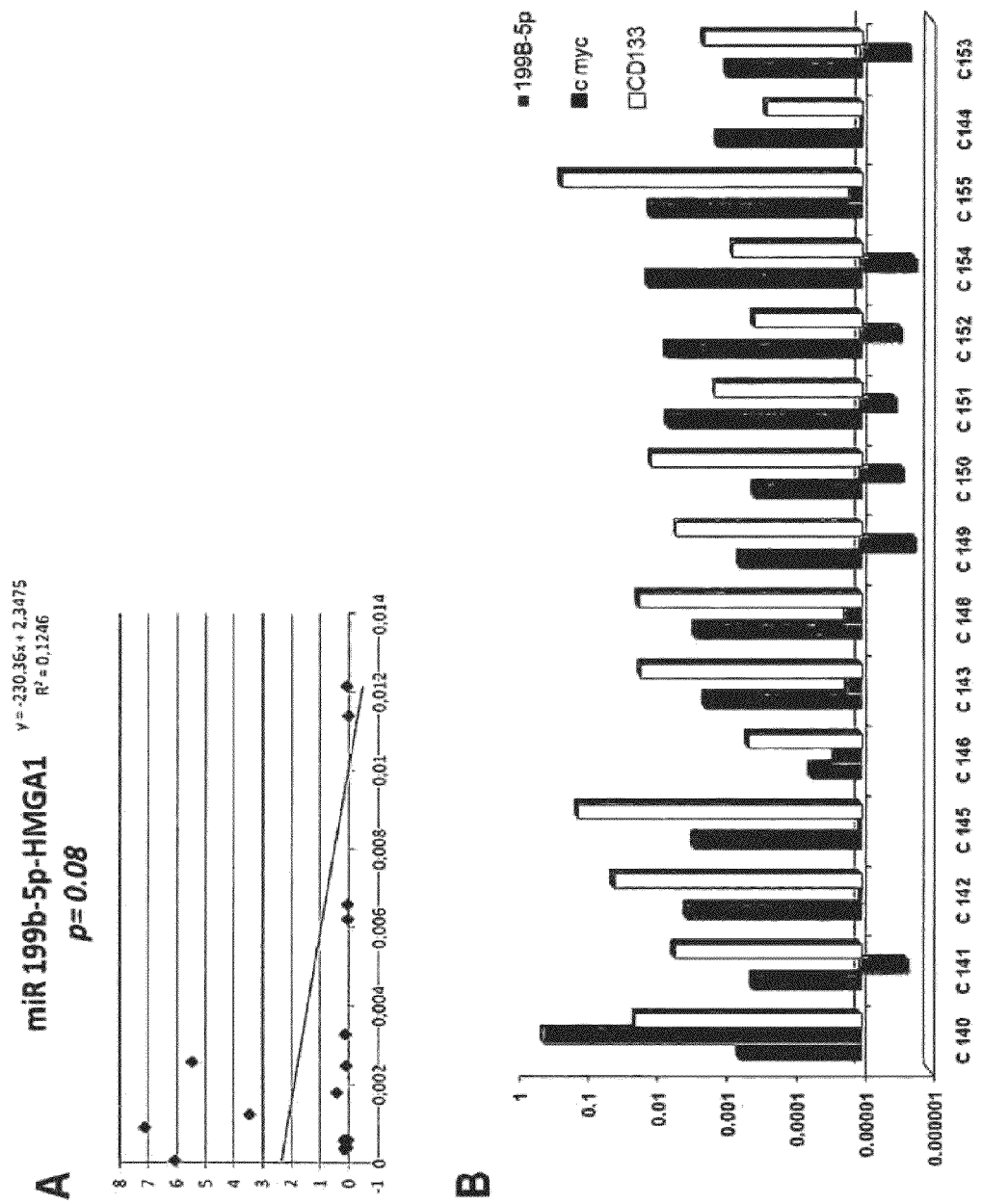

FIG. 21: A) Inversion correlation of the miR199b-5p expression and the gene HMGA1 (p=0.08) by real time PCR in 15 colon carcinoma tissue by Pearson test. B) Expression of miR199b-5p and of the genes c-myc and CD133 in 15 colon carcinoma tissues by real time PCR.

EXAMPLE 1

Study of mRNA 199b-5p Function in Cancer

Material and Methods
Ethical Disclose

All the animals were treated conformed to the national and international guides. The ethical approval was obtained from "Istituzioni per la Cure degli Animali e comitato etico CEINGE"—Universitá degli Studd di Napoli Federico II, Protocol #13—Aug. 1, 2007, and by Ministero della Salute Italiano, Dipartimento Sanitá Pubblica Veterinaria DL 116/92, confirming that all the experiments are according to low.
Flow Cytometry Analysis.

The flow cytometry analysis of S-phase fractions and cell-cycle kinetics were carried out using a FACSCalibur (Becton Dickinson, San Jose, Calif.) using CELL Quest version 3.3 software. The CD133 studies were carried out using the same instrument, with antibodies from Miltenyi Biotec (Auburn, Calif.), according to the manufacturer instructions. In brief, the cells were blocked in Fc receptor blocking reagent and incubated with an anti-CD133/1 (AC133)-phycoerythrin antibody (Miltenyi Biotec), for 10 min in the dark at 4° C. The cells were then washed and resuspended in PBS. Cells expressing higher levels of CD133 than the immunoglobulin G (IgG) controls were considered positive. For analyses of the side populations, cells (106/mL) were incubated with Hoechst 33342 (5 µmol/L; Sigma) for 90 min at 37° C. in EMEM containing 2% FBS. To ensure the correct identification of the side population cells, the cells were incubated as above with the addition of 50 µM verapamil (Sigma).
In-Vivo Imaging Via Stable Daoy Luciferase Clones Stable Daoy cell clones were generated by transfecting a luciferase-expressing vector (the firefly luciferase gene cloned in the plentiV5 vector; Invitrogen) into the stable 199bSC1 clone or into the control empty-vector clone. Then 100,000 viable 199b-Luc1 and Ctl-Luc-4 cells were mixed with a 1:1 PBS:matrigel solution (BD Biosciences, San Jose, Calif.). Six-week-old female athymic mice were anesthetised using avertin (Sigma) as a 3% solution in tert-amyl alcohol (Fisher), at a dose of 3 mg per 10 g body weight. The mice were injected s.c. with a total volume of 0.1 mL of matrigel PBS cell suspension, into each flank. The mice were imaged after the implantation of the cells, with tumor growth monitored by weekly bioluminescence acquisitions (BLI) using an MS 3D Illumina Imaging System (Xenogen Corp. Alameda, Calif.). For the acquisitions, the mice were isofluorane-anaesthetised i.p., injected with 100 µL D-luciferin (15 mg/mL stock) per 10 g body weight, and imaged for 30 s, 10 min after luciferin injection; four acquisitions per mouse were made (ventral, dorsal and each flank). To quantify the bioluminescence, the integrated fluxes of photons (photons per s) within each area of interest were determined using the Living Images Software Package 3.0 (Xenogen-Caliper). The emission data from the start of tumor growth were collected for at least 6 weeks, and then were normalized to the bioluminescence on the injection day. Calliper measurements of tumor sizes were made weekly, along the long and short axes, and estimations of their volumes were made using the formula: width2× length×0.52.
Animal Preparation and PET/CT Imaging The mice were kept in a ventilated cage (26° C.) for 1 h prior to imaging studies. Anesthesia was performed with intraperitoneal administration of a mixture of ketamine (100 mg/kg) and xylazine (10 mg/kg) (injection volume, 100 µl/10 g). PET was performed 1 h after administration of 3'-deoxy-3'-[18F]fluorothymidine ([18F]FLT), a marker of tumor proliferation (50 µL; 7.4 MBq; scan time, 18 min), in a lateral caudal vein, using an animal PET scanner (GE Healthcare eXplore Vista, FWHM 1.6 mm). High resolution CT studies (GE Healtcare eXplore Locus; spatial resolution, 45 µm) were performed within 24 h from the PET.
Data Analysis Maximum (SUVmax) and mean (SUVmean) standardized uptake values (SUVs) were calculated from the PET studies (SUV=tissue activity (MBq/cc)/[injected dose (MBq)/body weight (g)]). The PET/CT images were post-processed to obtain multiplanar reconstructions (MPRs), maximum intensity projections (MIPs), 3D volume rendering, and fusion images, using Osirix 3.3 (MAC OS 10.5 operating system). Additional 3D reconstructions were obtained using Micro-View (GE eXplore Locus).

Lesion volumes were calculated from PET data using in-house-developed software (based on IDL, ITT Vis Inc), by summarizing all spatially connected voxels with SUV>50% SUVmax. Lesion profiles defined with these procedures were used for ROI-based comparison between AdV5-Mock and AdV5-199b.

Figure 5:
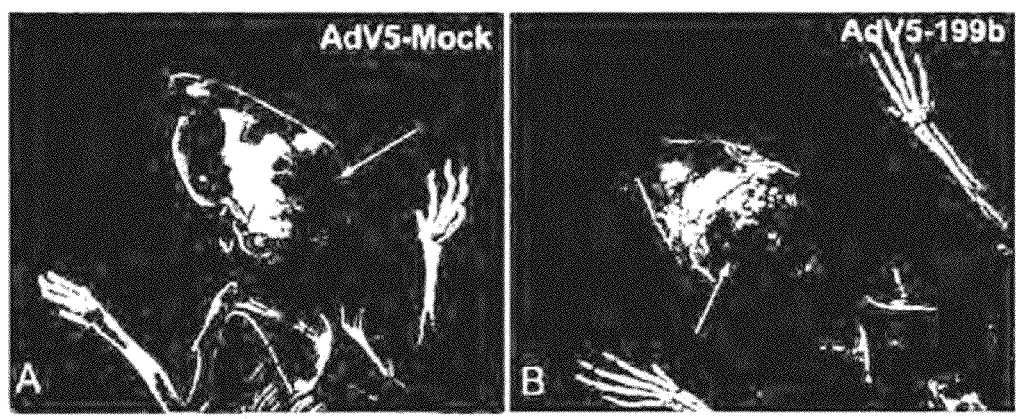

The results presented in FIG. 5 (main text) showed a tumor mass at the level of a wide skull defect at implant site potentially due to a high level of tumorigenesis occurring within the skull and high level of cartilaginous-bone degeneration with corresponding FLT uptake at PET. In this PET-CT analyses, we confirmed the presence of the development an enlarged tumor in the cerebellum of the control mice (AdV5-Mock#7), compared to the mice xenografted with over-expressing cells miR-199b-5p (AdV5-199p#5).
Standard Cell Culture.

The human Daoy and D283-MED MB cell lines were obtained from American Type Culture Collection (ATCC, Manassas, Va.) and were maintained in Eagle's minimum essential medium (EMEM; Sigma) supplemented with 10% fetal bovine serum (FBS), 10 U/ml penicillin and 0.1 mg/ml streptomycin (Celbio Pero, Milan, Italy). HEK-293 and SH-5YSY cells were maintained in Dulbecco's modified Eagle's medium (DMEM; Sigma) supplemented with 10% FBS, 10 U/ml penicillin and 0.1 mg/ml streptomycin.
Transfection of Daoy Cells and Luciferase Assays To determine the activity of miR-199b-5p on repression of the luciferase-3'UTR fused constructs, the pREYZO-miR-199b-5p construct and the pRL-CMV-3'UTR target construct were co-transfected into HEK293 cells at a ratio of 10:1, using the Polyfect reagent (Qiagen) together with the pGL3 basic vector, in the absence and presence of 2-OM (400 nM). Luciferase activities were analysed using a Dual Luciferase Reporter Assay system (Promega, Madison, Wis.).
AZA Treatment Five MB cell lines (d283, Daoy, med8a, ons76, uw228) were grown in DMEM supplemented with 10% FBS and antibiotics. Upon reaching 85% confluence, the media was spiked with 5-aza-deoxycytidine (AZA) (Sigma) to a final concentration of 5 µM. Over 72 h the media was replaced daily with fresh AZA-enhanced medium. RNA was extracted using a standard phenol (TRIzol)-chloroform protocol.

Vector Cloning

Pre-miR-199b was cloned in a pcDNA3 modified vector (pREYZO) (D'angelo et al., 2004) using EcoRI-XhoI restriction sites. HES1 and GSK-3~target-binding sites (3'UTRs) were cloned in tandem in the 3'UTR of 20 the pRL-cytomegalovirus (CMV) vector (Promega, Madison, Wis.) downstream of the coding region of Renilla luciferase (RL) in the XbaI site The HES1 3'UTR (including the 199b binding site) was amplified from genomic DNA with the following primers: HES1_3'UTR as AAAATCTAGACAGTTCGAAGACATAAAAGCC (SEQ ID NO: 96) and HES1_3'UTR as AAAATCTAGAAACGCAGTGTCACCTTCC (SEQ ID NO: 97), and was cloned in the TK vector (Promega, Madison, Wis.) upstream of the firefly luciferase gene, in the XbaI sites. HES1 full-length cDNA was obtained with a standard RTPCR approach from a Daoy cDNA.

Site-Directed Mutagenesis

The site-directed mutagenesis of the miR-199b-5p binding site in HES1 3'UTR was generated according to the manufacturer protocol of the QuikChange site-directed mutagenesis kit (Stratagene, La Jolla, Calif.). The following primer was used for mutagenesis (only sense sequence is given and the mutated nucleotides within the consensus sequence are underlined): HES1 3'UTR sense AACAGGAACTTGAATATTTGTAGAG AAGAGGACTTT (SEQ ID NO: 98).

TaqMan miRNAs Assay

Reverse Transcriptase Reactions

The reverse transcriptase (RT) reactions contained 40 ng RNA sample, 50 nM stem-loop RT primer, 1×RT buffer (P/N: 4319981, Applied Biosystems), 0.25 mM each of dNTPs, 3.33 U/ml MultiScribe RT (P/N: 4319983, Applied Biosystems) and 0.25 U/ml RNase inhibitor (P/N: N8080119; Applied Biosystems). The 15 µl reactions were incubated in an Applied Biosystems 9700 Thermocycler for 30 min at 16° C., 30 min at 42° C., 5 min at 85° C., and then held at 4° C.

Real-Time PCR

Real-time PCR was performed using a standard TaqMan PCR kit protocol on an Applied Biosystems 7900HT Sequence Detection System. The 20 µl PCR mix included 2 µl RT product, 10 µl TaqMan Universal PCR Master Mix (Applied Biosystems), 0.2 mM TaqMan probe. The reactions were incubated in a 96-well plate at 95° C. for 10 min, followed by 60 cycles of 95° C. for 15 s and 60° C. for 1 min.

RNA Isolation, cDNA Preparation and Real-Time Quantitative PCR

Total RNA was extracted from the cell lines using the Trizol reagent (Invitrogen). Synthesis of cDNA from total RNA (4 µg) was performed using a Super Script II First Strand Kit (Invitrogen). Real-time quantitative PCR was performed using standard protocols with an Applied Biosystems ABI PRISM 7900HT Sequence Detection system. To calculate the relative gene expression of the miR-199b-5p precursor, the relative amounts of each pre-miRNA were normalized to U6 miRNA; the other genes were normalized using the β-actin gene. Real-time PCR primers for each gene were designed using Primer Express software version 2.0 (Applied Biosystems). The primer sequences are available upon request.

The Unigene ID and the sequenze of the primers for the analysis of the gene involved in the cancer stem cell biology with 2^-DCt values are showed in the table 1.

TABLE 1

| Gene name | ID Unigene | Sense Primer | Antisense Primer | Daoy + DMSO | Daoy + DAPT 12 h |
|---|---|---|---|---|---|
| c-Myc | Hs.202453 | ATGAGGAGACACCG CCCAC (SEQ ID NO: 24) | AACATCGATTTCTT CCTCATCTTCTT (SEQ ID NO: 25) | 0.0987097 | 0.0542671 |
| Nanog | Hs.661360 | GCAAATGTCTTCTG CTGAGATGC (SEO ID NO: 26) | GCTGTCCTGAATAA GCAGATCCAT (SEQ ID NO: 27) | 0.0001832 | 0.0004488 |
| CD 133 | Hs.614734 | CTATGTGGTACAGC CGCGTG (SEQ ID NO: 22) | TAATCAATTTTGGA TTCATATGCCTTC (SEQ ID NO: 23) | 0.0020653 | 0.0012368 |
| Oct4 | Hs.249184 | ACTGCAGCAGATCA GCCACA (SEQ ID NO: 28) | TGGCGCCGGTTAC AGAAC (SEQ ID NO: 29) | 0.0001200 | 0.0007941 |
| PDGFR-B | Hs.509067 | AGGTTGCTGACGAG GGCC (SEQ ID NO: 84) | GGTGTTGACTTCAT TCAGGGTG (SEQ ID NO: 85) | 0.0006059 | 0.0000606 |
| PDGFR-A | Hs.74615 | TCAAGGCAGAAATA GGCAGCA (SEQ ID NO: 86) | TGGACGTCGATCA GGTCCA (SEQ ID NO: 87) | 0.0000003 | 0.0000015 |
| SPARC | Hs.708558 | TTGCCTGGACTCTG AGCTGA (SEQ ID NO: 88) | GGGTGACCAGGAC GTTCTTG (SEQ ID NO: 89) | 0.3431687 | 0.0797725 |
| ILF3 | Hs.465885 | CCGACACGCCAAGT GGTT (SEQ ID NO: 90) | ACACAAGACTTCA GCCCGTTG (SEQ ID NO: 91) | 0.0352218 | 0.0425171 |
| MYBL2 | Hs.179718 | AGCAAGTGCAAGGT CAAATGG (SEQ ID NO: 92) | GGCCCTCAGCTGC TCGT (SEQ ID NO: 93) | 0.0130289 | 0.0039321 |

TABLE 1-continued

| Gene name | ID Unigene | Sense Primer | Antisense Primer | Daoy + DMSO | Daoy + DAPT 12 h |
|---|---|---|---|---|---|
| TEAD4 | Hs.94865 | TCGGACGAGGAGG GCAAGATG (SEQ ID NO: 94) | GATGTAGCGGGCA ATCAGCT (SEQ ID NO: 95) | 0.0117936 | 0.0051764 |
| TCF7L1 | Hs.516297 | CCGCGGGACTATTT CGC (SEQ ID NO: 30) | AAAGAACGCGCTG TCCTGAG (SEQ ID NO: 31) | 0.0006742 | 0.0001026 |
| HMGA1 | Hs.518805 | AAAAACAAGGGTGC TGCCAA (SEQ ID NO: 36) | CCTTCCTGGAGTT GTGGTGGT (SEQ ID NO: 37) | 0.7977002 | 0.0048793 |
| ZIC1 | Hs.598590 | CAGTTCGCTGCGCA AACA (SEQ ID NO: 32) | GAGCCCTGCGAGG AGGAT (SEQ ID NO: 33) | 0.0283592 | 0.0002784 |
| HMGB3 | Hs.19114 | TTTTCCAAGAAGTG CTCTGAGAGG (SEQ ID NO: 38) | TTTCTCTTTCCCGG ACATCG (SEQ ID NO: 39) | 0.1946868 | 0.0055773 |
| KLF5 | Hs.508234 | GCATCCACTACTGC GATTACCC (SEQ ID NO: 34) | TGAGAAGACTTGG TATAAACTTTTGTG C (SEQ ID NO: 35) | 0.0027895 | 0.0236774 |

Western Blotting

Thirty μg cytosolic or nuclear lysates were loaded onto 12% polyacrilamide gels, and blotted onto polyvinylidene difluoride membranes (PVDF; BioRad, Milan, Italy). The membranes were then incubated with anti-HES1 (kind gift of Dr. Tetsuo Sudo TORAY Industries, Tebiro Kamakura, Japan), a polyclonal rabbit antibody (1:500), an anti-GSK3-β (B&D Bioscience) monoclonal antibody (1:2500), an anti-c-Myc polyclonal rabbit antibody (1:200) (Santa Cruz Biotechnology, Santa Cruz, Calif., USA), an anti-GABRA6 antibody (Santa Cruz Biotechnology, Santa Cruz, USA) (1:200), an anti-MATH3 antibody (Santa Cruz Biotechnology, Santa Cruz, USA) (1:200) and an anti-cyclin D1 (1:200) polyclonal rabbit antibody (Cell Signaling). An anti-β-actin antibody (1:1.000) (Sigma) was used as the control for equal loading of cytosolic lysates and a polyclonal anti-β-laminin antibody (1:50) (Santa Cruz Biotechnology, Santa Cruz, Calif., USA) for equal loading of nuclear lysates.

Soft-Agar Assays

Daoy cells and the stable 199b clone were seeded in 1 ml EMEM supplemented with 2% FBS, containing 0.3% agarose. Cultures were maintained for two weeks and refreshed with EMEM supplemented with 2% FBS twice per week. Colonies of more than 100 μm in diameter were counted under a Leica (Nussloch, Germany) DC500 compound microscope.

Proliferation Assay MTS

Cell proliferation was determined using the CellTiter96 AQueous Non-Radioactive Cell Proliferation Assay Kit (Promega Madison, Wis.). The cells were seeded into 96-well plates at a density of $1 \times 10^3$ cells/well in EMEM without or with FBS. After 0, 24, 48 and 72 h, MTS ([3-(4,5-dimethylthiazol-2-yl)-5-(3-carboxymethoxyphenyl)-2-(4-sulfophenyl)-2H-tetrazolium]) and PMS (phenazine methosulfate) were added to each well and after 4 h the absorbance of each well was measured at 490 nm ($OD_{490}$) using Multilabel counter Victor³ (Perkin Elmer). Each condition was performed with five wells and each experiment was repeated twice.

Immunohistochemistry

Unmasking was performed in 10 mM citrate buffer, pH 6, at 97° C. for 45 min. Blocking was performed with Antibody Diluent with Background Reducing Components (Dako Cytomation) for 30 min at room temperature; the polyclonal anti-HES1 (1:1000), anti-Nestin (1:1000), anti-GABRA6 (1:100), anti-MATH3 (1:100) antibodies were used at overnight at 4° C. The signals were revealed using Kit LSAB DAM), for 15 min (Biotin), and Kit LSAB DAKO, for 15 min (Streptavidina), at room temperature.

DAB was from DakoCytomation, and the slides were mounted and examined under a Leica (Nussloch, Germany) DC500 compound microscope.

Locked Nucleic Acid In-Situ Hybridization

Dried slides from murine embryonal brain or human multiple tissue arrays were fixed in 4% paraformaldehyde for 10 min at room temperature, and washed twice for 3 min in 1×PBS at room temperature. During the washing steps, the acetylation solution was freshly prepared, containing: 0.01% triethanolamine and 0.0025 mM acetic anhydride in diethylenepyrocarbonate (DEPC) water. The slides were then placed in a beaker of acetylation solution and stirred gently for 10 min. The slides were then subjected to proteinase K treatment at 5 μg/ml in DEPC-treated water, followed by three washes for 3 min in 1×PBS at room temperature, and pre-hybridized for 6 h at room temperature with hybridization solution. Hybridization was with 150 μl denaturizing hybridization, with 1 pM of the locked nucleic acid DIG-labelled probe (Exiqon, miRCURY). Hybridization was performed at 60° C. overnight. Slides were soaked in pre-warmed 60° C. 5×SSC and the coverslips were carefully removed; the slides were then incubated in 0.2×SSC at 60° C. for 1 h, then incubated in a 0.1 M Tris, pH 7.5, 0.15 M NaCl at room temperature for 10 min. The surplus solution was removed and the slides placed in a humidified chamber; 500 μl of blocking solution (1% FCS in 0.1 M Tris, pH 7.5, 0.15 M NaCl) was placed on the slides for an incubation of 1 h at room temperature. The anti-DIG-alkaline phosphatase antibody was diluted 1:2,000 in blocking solution and incubated at 4° C. overnight. The slides were washed three times in 0.1 M Tris, pH 7.5, 0.15 M NaCl, and then equilibrated in 0.1 M Tris, pH 9.5, 0.1 M NaCl, 50 mM MgCl. The slides were stained with BCIP/NTB (Sigma), dehydrated, and mounted; images are acquired under a Leica (Nussloch, Germany) DC500 compound microscope.

DAPT Treatment of Daoy Cell Line

The human Daoy cell line was obtained from American Type Culture Collection (ATCC, Manassas, Va.) and maintained in EMEM (Sigma Aldrich, Milan, Italy) supplemented with 10% fetal bovine serum (FBS) (Celbio Pero, Milan, Italy), 10 U/ml penicillin and 0.1 mg/ml streptomycin (Celbio Pero, Milan, Italy). HEK-293 and SH-5YSY cell were maintained in DMEM (Sigma) supplemented with 10% FBS (Celbio), 10 U/ml penicillin and 0.1 mg/ml streptomycin (Celbio).

N—[N-(3,5-difluorophenacetyl)-l-alanyl]-S-phenylglycine t-butylester (DAPT (Sigma-Aldrich) treatment of the Daoy cells was performed as follows: the cells were plated and allowed to grow overnight in medium containing 10% FBS. The next morning, the medium was replaced with medium containing 10 µM DAPT and replaced each 4 h with this medium. The expression assays was performed after 0, 6, 12, 24 h of treatment of miR199b, using control experiments including the corresponding volume of DMSO as vehicle.

In-Vitro Cell-Motility Assay

The control DAOY cell line and the stable DAOY-199bSC1 clone were used in the 'cell-motility' assays. Cell migration assays were performed with 8-µm pore size Transwells (Costar). The cells were suspended by trypsinization, washed, and resuspended in 100 µl serum-free DMEM containing 0.1% BSA ($5 \times 10^4$ cells) and placed in the upper chamber of the Transwells. The lower chamber was filled with 600 µl serum-free DMEM supplemented with 0.5% FBS, as the chemoattractor. The cells were allowed to migrate for 1 h at 37° C. Cells migrating to the lower side of the polycarbonate membrane were fixed with 2.5% glutaraldehyde and stained with Hematoxylin solution (Sigma). The cells were counted, and the analysis performed on three Transwells for each condition, and each experiment was repeated twice.

Patient Samples

A total of 61 cases of MB were collected from three different centres: 12 surgical MB specimens were from the Department of Neurosurgery, Santobono Hospital, Naples, Italy; 18 were from the Institute Curie, Paris, France; and 31 were from. The Hospital for Sick Children, Toronto, Canada. The characteristics of the patients are given in Table 2. Informed consent was obtained before the analysis of the tumor samples. All of the specimens were obtained at the time of diagnosis, prior to radiation or chemotherapy, and 29 were subjected to histopathological review according to the WHO criteria [14], the M status information was available for all of the patients. Control human tissues were obtained from the NICHD Brain and Tissue Bank for Developmental Disorders at the University of Maryland, Baltimore, Md. Total RNA was extracted using Trizol reagent (Invitrogen), as described above for cell lines, and analyzed for miR-199b-5p expression levels by the TaqMan MicroRNAs Assay. The miR-199b-5p expression levels were divided into two groups (low and high), according to the median, and were compared between metastatic and non-metastatic groups using the Pearson Chi-Square test. Survival analyses were obtained through SPSS software, using a Log-rank test to ascertain significance. Statistical significance was established at a P value of 0.05.

TABLE 2

| Patients | Age at diagnosis (mounths) | Follow-up (mounths) | Last state | M stage (Chang) | Istology | Relative expression Mir-199b-5p (U6) $2^{-\Delta Ct}$ |
|---|---|---|---|---|---|---|
| MB102 | 108 | 32.8 | dead | M3 | classic | 0.00099561 |
| MB108 | 96 | 19.5 | CR1 | M0 | desmoplastic | 0.09001227 |
| MB106 | 50 | 4 | dead | M0 | classic | 0.010613742 |
| MB111 | 9 | 72.2 | CR1 | M0 | desmoplastic | 0.120138583 |
| MB114 | 21 | 74.6 | CR1 | M0 | desmoplastic | 0.000383771 |
| MB119 | 93 | 32.8 | CR1 | M1 | classic | 0.003199194 |
| MB120 | 108 | 27.5 | CR1 | M0 | classic | 0.218701701 |
| MB123 | 37 | 13.6 | dead | M3 | classic | 0.006959284 |
| MB126 | 13 | 74.8 | CR2 | M0 | classic | 0.067296233 |
| MB128 | 78 | 31.7 | CR1 | M0 | desmoplastic | 0.076875702 |
| MB133 | 158 | 87 | CR1 | M0 | classic | 0.025786457 |
| MB137 | 93 | 84 | CR1 | M0 | classic | 0.019919437 |
| MB79 | 36 | 14.1 | dead | | medullo-myoblastoma | 0.194622694 |
| MB80 | 96 | 43.1 | CR1 | M2 | desmoplastic | 0.000152879 |
| MB81a | 109 | 14 | dead | M0 | Big cells | 0.019211033 |
| MB95 | 41 | 32.1 | CR1 | M0 | classic | 0.002433079 |
| MB96 | 44 | 42 | dead | M0 | classic | 0.004037267 |
| MB99 | 99 | 21.9 | dead | M0 | classico | 0.015258058 |
| N1 | 69 | 49 | CR1 | M2 | classic | 0.005729706 |
| N2 | 90 | 20 | CR1 | M0 | classic | 0.206256346 |
| N3 | 26 | 34 | CR1 | M0 | desmoplastic | 1.770829272 |
| N4 | 124 | 14 | CR1 | M0 | classic | 0.014508728 |
| N5 | 64 | 36 | PR | M0 | classic | 0.386116248 |
| N6 | 35 | 1 | dead | M3 | Big cells | 0.007290413 |
| N7 | 76 | 22 | CR1 | M0 | classic | 0.009490309 |
| N8 | 169 | 26 | CR1 | M0 | classic | 0.066566636 |
| N9 | 128 | 10 | CR1 | M0 | classic | 0.379446328 |
| N10 | 29 | 20 | PD | M0 | classic | 0.032431549 |
| N11 | 140 | 34 | CR1 | M0 | classic | 0.097916916 |
| N12 | 34 | 19 | PD | M0 | desmplastic | 0.034231549 |
| MDT-MB-1 | 25 | 6 | dead | M + (1-2-3) | | 1.574119241 |
| MDT-MB-2 | | | | M + (1-2-3) | | 0.012369684 |

TABLE 2-continued

| | | | | | | |
|---|---|---|---|---|---|---|
| MDT-MB-3 | | | | M0 | | 0.408535751 |
| MDT-MB-4 | | | | M0 | | 0.014345797 |
| MDT-MB-5 | | | | M + (1-2-3) | | 0.117424185 |
| MDT-MB-6 | 27 | 33 | dead | M0 | desmoplastic | 1.924140125 |
| MDT-MB-7 | 88 | 14 | dead | M0 | anaplastic | 0.369604567 |
| MDT-MB-8 | 124 | 39 | alive | M0 | anaplastic | 0.499210685 |
| MDT-MB-9 | 39 | 95 | alive | M0 | | 0.085790892 |
| MDT-MB-38 | 60 | 78 | alive | M0 | | 0.019155739 |
| MDT-MB-46 | | | | M0 | | 1.875853287 |
| MDT-MB-50 | | | | M + (1-2-3) | | 0.043612817 |
| MDT-MB-71 | | | | M0 | | 0.07458206 |
| MDT-MB-100 | 32 | 34 | alive | M0 | | 0.645850534 |
| MDT-MB-102 | 26 | 33 | alive | M + (1-2-3) | anaplastic | 0.020193158 |
| MDT-MB-103 | 65 | 33 | alive | M0 | | 0.130267521 |
| MDT-MB-118 | 109 | 32 | alive | M + (1-2-3) | anaplastic | 1.776616235 |
| MDT-MB-124 | | | | M0 | | 0.902823686 |
| MDT-MB-131 | | | | M + (1-2-3) | | 0.277894072 |
| MDT-MB-154 | | | | M + (1-2-3) | | 0.03848591 |
| MDT-MB-174 | | | | M + (1-2-3) | | 0.016130305 |
| MDT-MB-175 | | | | M0 | | 0.821566771 |
| MDT-MB-177 | | | | M + (1-2-3) | | 0.004737906 |
| MDT-MB-193 | | | | M + (1-2-3) | | 0.142617576 |
| MDT-MB-194 | | | | M + (1-2-3) | | 0.484220261 |
| MDT-MB-201 | | | | M0 | | 0.053878318 |
| MDT-MB-207 | 61 | 110 | alive | M0 | | 0.025498266 |
| MDT-MB-220 | 69 | 20 | alive | M0 | | 1.119673662 |
| MDT-MB-222 | 72 | 20 | alive | M + (1-2-3) | | 0.050742316 |
| MDT-MB-223 | 131 | 20 | alive | M0 | | 0.374030612 |
| MDT-MB-224 | 167 | 13 | dead | M0 | anaplastic | 1.02682E−10 |
| 2M2 | 10 | 26 | CR1 | M0 | Classic | 0.007714069 |
| 2M16 | 9 | 72 | alive | M0 | Classic | 0.001090312 |
| 4M1 | 1 | 3 | dead | M0 | Classic | 0.022951675 |
| 4M10 | 8 | 8 | alive | M1 | Classic | 0.000362543 |
| 4M11 | 9 | 6 | 0 | M3 | Classic | 0.012582419 |
| 4M12 | 5 | 58 | 0 | M0 | Classic | 0.003358695 |
| 4M13 | 16 | 14 | 0 | M0 | Classic | 0.280568718 |
| 4M15 | 9 | 14 | CR1 | M1 | Classic | 0.066604933 |
| 4M16 | 9 | 18 | vivo | M0 | Classic | 0.004022173 |
| 4M17 | 8 | 24 | vivo | M3 | Classic | 0.182681185 |
| 4M18 | 14 | 22 | vivo | M0 | Big cells | 0.245240791 |
| 4M19 | 10 | 62 | vivo | M3 | Classic | 0.072460116 |
| 4M2 | 6 | 12 | vivo | M0 | Classic | 0.055299918 |
| 4M20 | 5 | 26 | vivo | M1 | Classic | 0.001948092 |
| 4M21 | 2 | 31 | vivo | M3 | Big cells | 0.043166742 |
| 4M22 | 4 | 27 | vivo | M3 | classic | 0.001217318 |
| 4M23 | 11 | 17 | morto per la malattia | M2 | classic | 0.034755336 |
| 4M26 | 10 | 12 | vivo | M0 | classic | 0.066137644 |
| 4M27 | 8 | 36 | vivo | M2 | classic | 0.052555486 |
| 4M28 | 16 | 49 | CR1 | M0 | classic | 0.017134081 |

TABLE 2-continued

| | | | | | | |
|---|---|---|---|---|---|---|
| 4M3 | 9 | 24 | vivo | M3 | classic | 0.173909476 |
| 4M30 | 6 | 14 | vivo | M0 | classic | 0.000593161 |
| 4M31 | 6 | 50 | vivo | M0 | classic | 0.199915108 |
| 4M32 | 3 | 48 | vivo | M0 | classic | 0.203934051 |
| 4M33 | 1 | 36 | vivo | M0 | classic | 0.080160885 |
| 4M35 | 6 | 36 | vivo | M0 | classic | 0.020431867 |
| 4M36 | 2 | 36 | vivo | M3 | classic | 0.102537563 |
| 4M37 | 3 | 48 | vivo | M1 | classic | 0.01621208 |
| 4M38 | 8 | 15 | morto per la malattia | M2 | classic | 0.000346883 |
| 4M39 | 7 | 18 | vivo | M0 | classic | 0.014986991 |
| 4M4 | 7 | 60 | vivo | M0 | classic | 0.161266704 |
| 4M40 | 10 | 36 | vivo | M0 | classic | 0.001348005 |
| 4M41 | 12 | 36 | vivo | M0 | classic | 0.057124436 |
| 4M42 | 6 | 18 | vivo | M0 | classic | 0.032851388 |
| 4M43 | 14 | 16 | vivo | M3 | classic | 0.033246248 |
| 4M44 | 8 | 22 | vivo | M3 | Big cells | 0.228057449 |
| 4M48 | 11 | 12 | vivo | M3 | classic | 0.014309066 |
| 4M49 | 6 | 20 | CR1 | M3 | classic | 0.007560172 |
| 4M5 | 7 | 18 | vivo | M0 | classic | 0.003118728 |
| 4M50 | 6 | 41 | vivo | M0 | classic | 0.131638757 |
| 4M55 | 12 | 36 | vivo | M0 | classic | 0.011346624 |
| 4M58 | 3 | 15 | morto per la malattia | M3 | Big cells | 0.003100982 |
| 4M6 | 10 | 26 | vivo | M0 | classic | 0.017322564 |
| 4M7 | 4 | 20 | vivo | M1 | classic | 0.008736515 |
| 4M8 | 8 | 12 | vivo | M0 | classic | 1.065853534 |
| 4M9 | 8 | 26 | vivo | M0 | classic | 0.007555274 |

| Patients code | Age at dead (mounths) | Mir-199-5p U6 $2^{\hat{}}$-DCt |
|---|---|---|
| Group 1-2 years | | |
| 1210 | 0.2 | 0.028323341 |
| 1157 | 0.02 | 0.091384778 |
| 1102 | 0.39 | 0.010811309 |
| 779 | 0.005 | 0.009558291 |
| 814 | 1.41 | 0.031308608 |
| Group 13-16 years | | |
| 1297 | 15.81 | 0.001938772 |
| 1158 | 16.63 | 0.001053237 |
| 1065 | 15.29 | 0.002201934 |
| 1024 | 14.6 | 0.000768088 |
| 931 | 13.12 | 0.003939267 |
| 142 | 16.73 | 0.000206487 |

Adenovirus Construction

The miR199b sequence was 5'-XhoI, 3'-HindI III directed cloned into the VQ Ad5CMV K-NpA shuttle vector, supplied from ViraQuest Inc., Innovative Adenovirus Technologies and Reagents, which provided its recombination and 199b adenovirus construction (see FIG. 16 that showed the vector sequence SEQ ID NO: 2 and FIG. 15 that showed the vector with the sequence SEQ ID NO: 1). They also supplied the control backbone E3 Luciferase virus, generated from a VQ Ad5CMVeGFP plasmid.

Adenoviral Infection

Infection with recombinant viruses was accomplished by exposing cells to adenovirus in 500 µl complete cell culture medium for 1 h, followed by addition of other medium. We used GFP-expressing by the adenovirus (AdV MOCK and AdV 199b) as a control when determining transfection efficiency.

Heterotransplantion into Right Ventricle of Cerebellum of SCID Mice

To establish intracerebellar xenograft models, 6-to-8-week-old SCID mice were anesthetized with Tribromoethanol (Avertin®) (50 mg/kg); after this, a small skin incision (1 mm) was made and a burr hole (0.7 mm in diameter) created with a microsurgical drill (Fine Science Tools, Foster City, Calif.). Daoy Luc cells infected with adenovirus mock, adenovirus 199b and 199b LUC1 stable clones ($10^5$) were suspended in 5 µL PBS and injected slowly through the burr hole into the right cerebellar hemisphere (stereotactic coordinates from bregma anteroposterior 5.5 mm; right lateral 2.1 mm; dorsoventral 5.0 mm) using a 10-AL, 26-gauge Hamilton Gastight 1701 syringe needle that was inserted perpendicular to the cranial surface. The animals were monitored weekly by bioluminescence to evaluate tumor growth for 8 weeks.

3D Acquisition

IVIS Spectrum: this system acquires a photographic and a structured light image, and two or more bioluminescent images at different wavelengths (560 to 660 nm), and generates the surface topography (mesh) of the subject. Modifying specific user-modifiable DLIT algorithm parameters (for example, analysis wavelengths, source spectrum, and tissue properties), we can reconstruct the position, geometry and strength of the luminescent sources in the subject. The Living Image® software provides digital mouse atlases that allow the display of a 3D skeleton and organs on the 3D reconstruction.

Animal PET and SPECT-CT

The mice were then anesthetized with 2.5% isofluorane and kept under 1% isofluorane anesthesia throughout all of the imaging procedures. The [$^{18}$F]FDG and [$^{18}$F]Fluoride PET imaging was used to examine tumor-cell-induced metabolic and skeletal changes, respectively. The images were acquired with three bed positions (10 min per bed position, for a total of 30 min) and an axial resolution of 1.2 mm, using an Explorer-Vista small animal PET-CT system (GE Healthcare).

Results

Hsa-miR-199b-5p Silences HES1 Expression Via 3'UTR Binding.

Our in-silico analysis of the mirBase targets database [27] was directed towards identification of miRNAs potentially targeting HES1, an effector of the Notch pathway, a fundamental mechanism in the regulation of MB cell proliferation. MiR-199b-5p and miR-199a-5p were the better scoring miRNAs, and were predicted to bind the 3'UTR of human bHLH HES1. We focused on miR-199b-5p due to its ability to decrease HES1 expression under transient over-expression, as compared to miR-199a-5p (FIG. 9A, B). MiR-199b-5p is lost in lung tumors [28] and it has been mapped to a genomic region deleted in bladder cancer [29]. MiR-199a* (also known as miR-199a-5p, and with an identical sequence to miR-199b-5p) is also reduced in hepatocellular carcinoma [30-32]. The analysis of miR-199b-5p expression in two MB cell lines, human adult tissue and mouse cerebellum, is shown in FIGS. 9C, D and 10A, B.

To determine whether HES1 is a target of miR-199b-5p, the HES1 3'UTR was cloned downstream of a luciferase reporter gene vector; pre-miR-199b-5p was also cloned in a mammalian expression vector. HEK-293 cells were then transfected with the relative luciferase activity showing that miR-199b-5p co-transfection decreased reporter gene activity, thus indicating binding with the 3'UTR and destabilisation of productive translation of luciferase mRNA (FIG. 9, 9E). As controls, HES1 3'UTR mutated in the miR-199b-5p binding site was not affected by miR-199b-5p (FIG. 9, 9E), and when a 2-O'-methyl oligoribonucleotide (2-OM) complementary to mature miR-199b-5p was co-transfected, it counteracted the effects of miR-199b-5p transfection, restoring reporter activity (FIG. 9, 9E). Similar results were obtained in Daoy MB cells (FIG. 9 FIG. 9F).

To determine the role of miR-199b-5p in MB cell biology, the miR-199b-5p expression construct was transfected into Daoy cells, and several stable clones over-expressing miR-199b-5p were selected. Over-expression was confirmed by real-time PCR (FIG. 9, 9G). Three clones demonstrated reduced HES1 protein levels, one of which (199bSC1) showed no detectable HES1. The 199bSC1 and 199bMC1 clones were selected for further investigation (FIG. 9, 9H). These effects of miR-199b-5p on HES1 protein expression were not restricted to the stable clones or Daoy cells, as D283MED cells transiently transfected with the expression construct for miR-199b-5p also showed reduced HES1 levels (FIG. 9, 9B).

To strengthen these findings, the 199bSC1 clone was transfected with 2-OM antisense to miR-199b-5p and used as a negative control (FIG. 9, 9I). Here, HES1 levels were restored, suggesting 2-OM block of HES1 repression by miR-199b-5p, providing further confirmation that miR-199b-5p targets HES1 directly. Other potential targets of miR-199b-5p were also investigated in this way (FIG. 9, FIG. 10C, D).

Over-Expression of miR-199b-5p Reduces Cell Proliferation and Impairs the Clonogenic Potential of MB Cell Lines.

Figure 1:
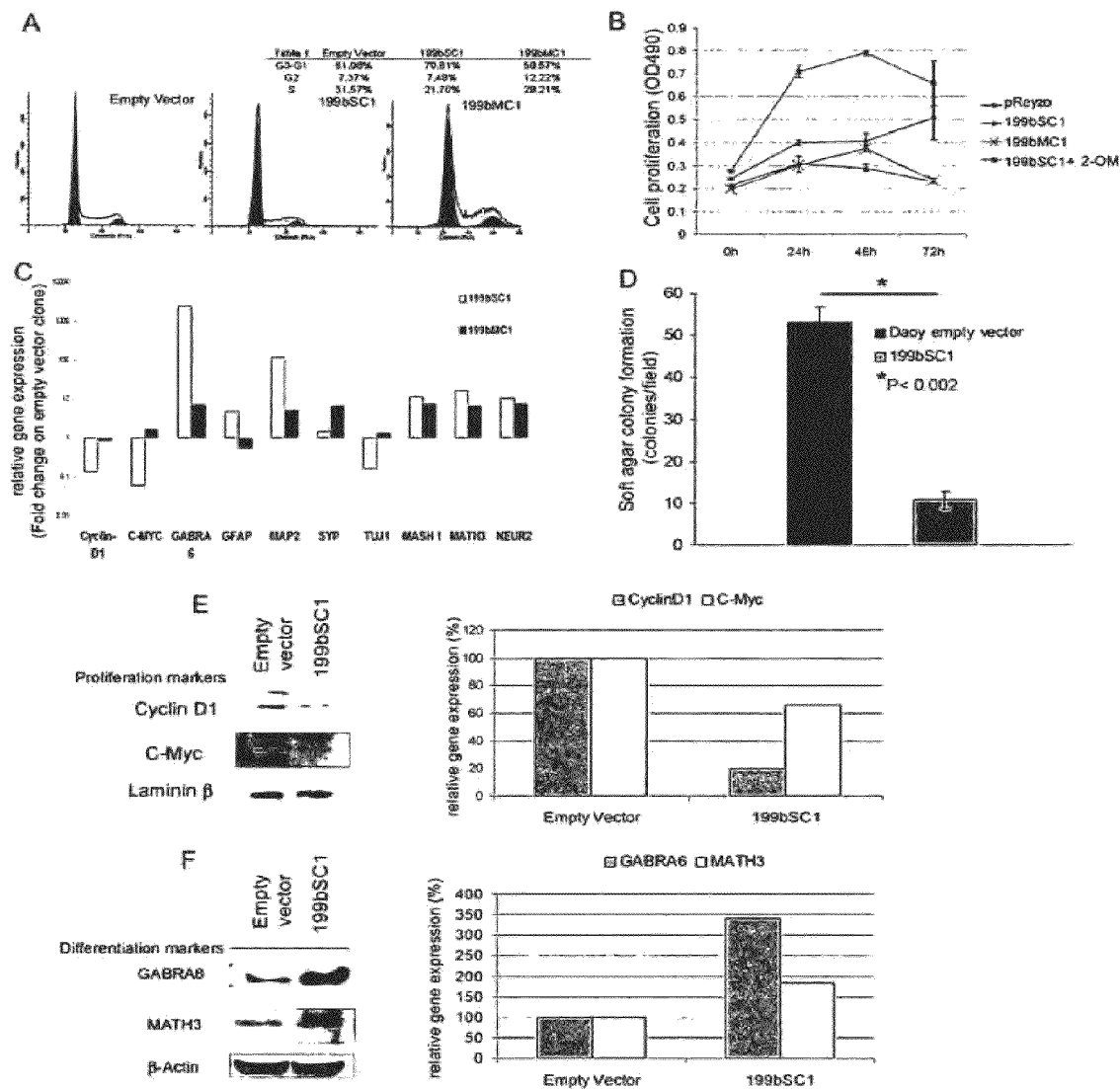

The 199bSC1 and 199bMC1 clones had reduced proliferation rates under standard culture conditions, when compared to the control clone. Thus, we looked for potential cell-cycle alterations in these clones. FACS analysis on the 199bSC1 clone showed a 31% decrease in S-phase fractions, and an increase in cells in G0-G1 of 15%, as compared to the empty vector clone (FIG. 1A). This suggested that exit from the cell cycle has a role in the reduced proliferation rate of the Daoy cell 199bSC1 clone. In contrast, the 199bMC1 clone did not show significant changes in its cell cycle. We believe these findings to be due to an overall lower efficiency of 199bMC1 for reducing HES1 protein levels. These cell-cycle phenotypes translated into decreased proliferation rates in vitro, as evaluated by in-vitro proliferation assays comparing the 199bSC1 and 199bMC1 clones with an empty-vector clone and a transient transfectant for 2-OM designed against miR-199b-5p (FIG. 1B). Both the 199bMC1 and the 1999SC1 clones showed markedly reduced proliferation rates. Transfection of this antisense 2-OM induced a marked increase in proliferation of the stable 199bSC1 clone, in agreement with restored expression levels of HES1, These results on Daoy cell proliferation were confirmed also with D283 and ONS76 cells (FIG. 10F). The effects of miR-199b-specific 2-OM were also confirmed in wild-type Daoy cells, where it potentially acts on the endogenous miR-199b (FIG. 10G).

The effects of the induction of miR-199b-5p were evaluated on molecular markers of proliferation and differentiation by a real-time approach. As illustrated in FIG. 1C, MAP2, which is mostly expressed in mature neurons [33], was up-regulated in the stable 199bSC1 and 199bMC1 clones. Similarly, Daoy cells have been reported to express GFAP after differentiation with phenylbutyrate [34], and in the stable 199bSC1 clone, GFAP levels were increased. Overall, the picture of gene expression in our stable cell line over-expressing miR-199b-5p is in agreement with the phenotype that has been seen in the brain of the Hes1−/− mouse [23]. Among the other genes, GABRA6, a marker of cerebellar granule cell differentiation, was also significantly over-expressed in the stable clones (FIG. 1C).

A fine-tuned cascade of positive and negative bHLH transcription factors is central to neurogenesis, with genes such as MASH1, MATH3 and NGN2 inducing neurogenesis, and HES1-mutant mice showing up-regulation of these activator-type bHLHs [35]. Both miR-199b-5p stable clones showed increases in expression of pro-neural bHLH. In agreement with their reduction in proliferation rate, the proliferation markers c-Myc and cyclin D1 were decreased. Of the two clones analysed, 199bSC showed the more consistent phenotype; we explain these results by the more efficient HES1 silencing in this clone.

Since the miR-199b-5p stable 199bSC1 clone showed a stronger and more consistent phenotype, we next examined it in a standard clonogenic assay, to determine whether anchorage-independent growth was affected by miR-199b-5p. Here, there was an 80% reduction in colony formation potential, compared to the empty-vector clone (FIG. 1D). In agreement with this reduction in proliferation rate, the proliferation markers c-Myc and cyclin D1 were decreased (FIG. 1E). We confirmed also at the protein level that GABRA6 and MATH3 were up-regulated in the 199bSC1 clone (FIG. 1F); the latter is known to be directly repressed by HES1 [35].

MiR-199b-5p Depletes the Side Population Compartment in the Daoy Cell Line, and Negatively Regulates MB Tumor Stem-Cell Populations.

The Notch pathway has been linked to the fraction of MB tumor cells that harbour precursor stem-cell markers [36], and HES1 has a role in self-renewing of multipotent progenitor cells [23]. This side population (SP) of tumor cells has a role in the engrafting of a tumor in animal models [37]. We thus examined the influence of miR-199b-5p on the population of tumor cells that exclude the Hoechst 33342 dye, a strategy to identify these SP cells. This was determined by flow cytometry in the Daoy cell line, the SP of which accounts for up to 4.9% of the cells, as compared with verapamil-treated cells (the negative control) (FIG. 11A, B). This verapamil treatment was based on verapamil inhibition of the ion-pumps responsible for Hoechst 33342 dye exclusion, thus enabling the SP cells to be seen [38]. Staining of 199bSC1 and 199bMC1 cells indicated that the SP was ablated, as there were close to no differences between the Hoechst-treated sample and the Hoechst plus verapamil samples (FIG. 11C-F).

Figure 2:
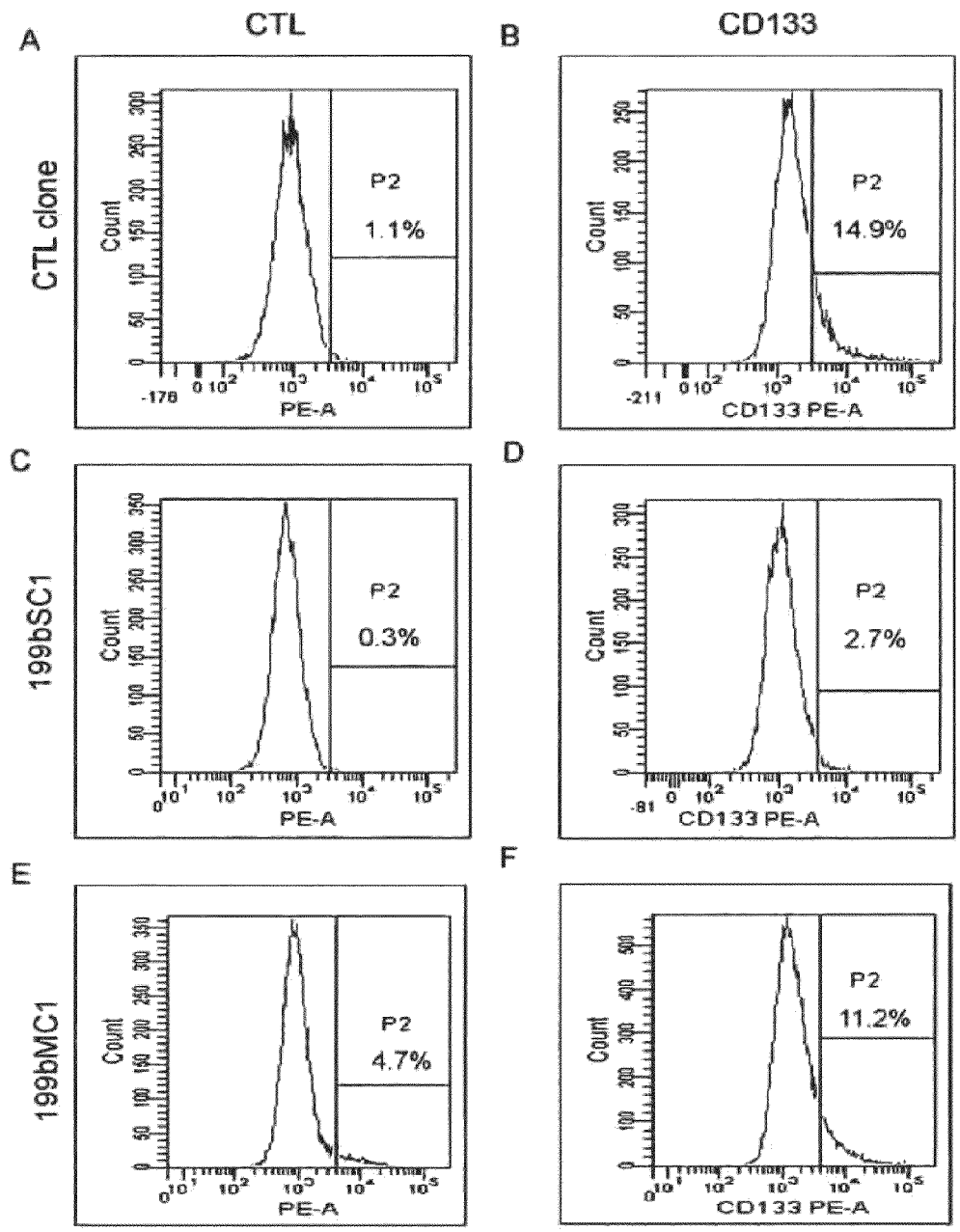

It is also known that central nervous system tumor stem cells express the CD133 antigen, and that these cells are uniquely capable of tumor formation in NOD-SCID mice [18,39]. Additionally, the Notch pathway has a central role in the self-renewing process, with its inhibition leading to depletion of CD133-positive (CD133+) Daoy cells via induction of apoptosis of progenitor-like cells [36]. Recently it was shown that CD133+ Daoy cells promote tumor growth in the flank of nude mice, while CD133− cells do not [40]. For these reasons, we evaluated the CD133 positivity of Daoy cells as compared to the stable 199bSC1 and 199bMC1 clones (FIG. 2). Here, the wild-type cells were 14.8% CD133+, while in the stable 199bSC1 and 199bMC1 clones this was reduced to 2.4% and 6.5% CD133+, respectively (FIG. 2C-F). This thus demonstrated a role for miR-199b-5p in negative regulation of this fraction of tumor-initiating cells.

HES1 Over-Expression Rescues the miR-199b-5p Clone Phenotype.

Figure 3:
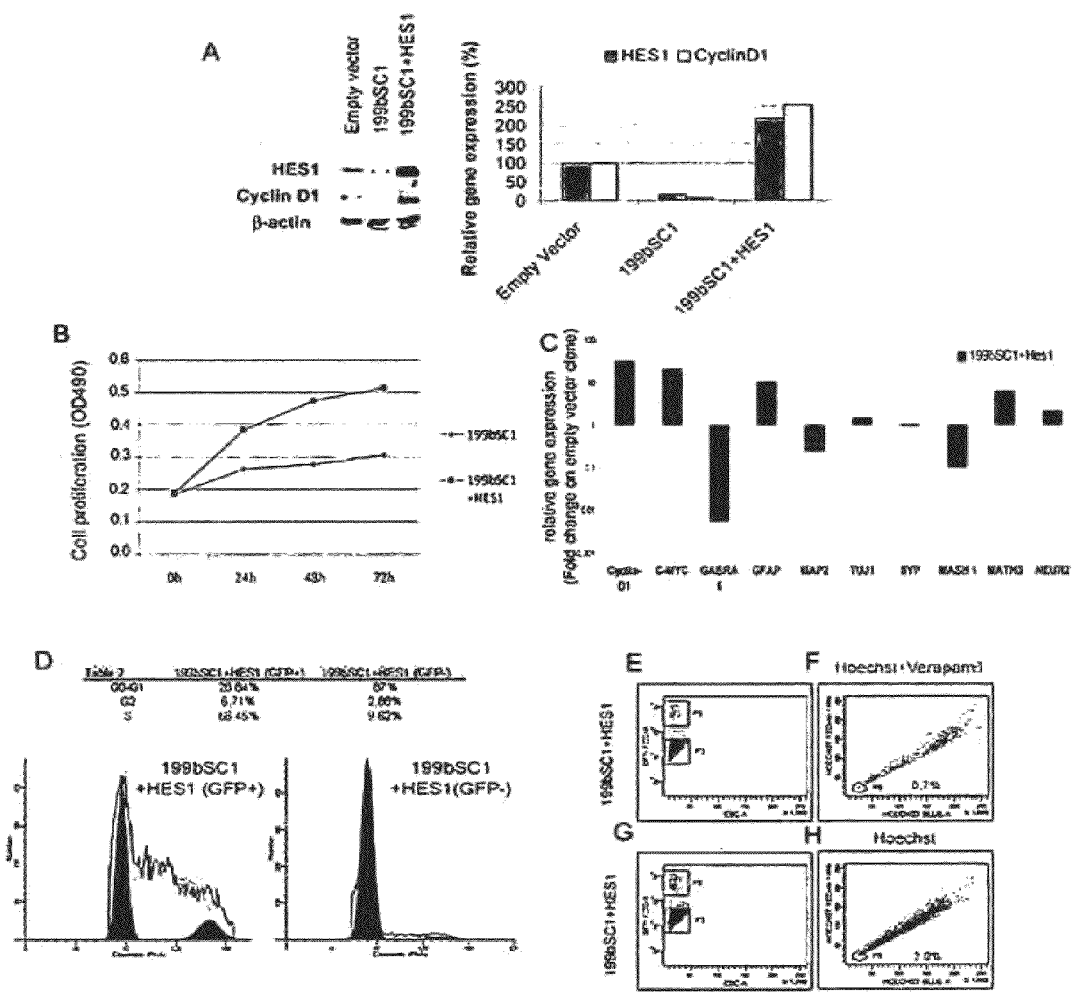

To confirm that the cellular phenotype is directly correlated with down-regulation of HES1, we performed in-vitro cell-rescue experiments. We chose to rescue the more consistent phenotype, shown by the stable 199bSC1 clone. When full-length HES1 cDNA was cloned and transfected into the stable Daoy-cell 199bSC1 clone, HES1 expression was restored, as evaluated by immunoblotting (FIG. 3A). We also noted the re-expression of cyclin D1, which was down-regulated in the stable 199bSC1 clone. Restored HES1 expression also reversed the effects of miR-199b-5p on cell proliferation (FIG. 3B). At the same time, the transfection of HES1 cDNA into the 199bSC1 clone decreased induction of pro-neural bHLHs and differentiation markers, and increased levels of proliferation genes (FIG. 3C). Furthermore, the transient transfection of HES1 cDNA into the stable 199bSC1 clone led to an increase in the percentage of cells in S phase, and a removal of the block on the G0-G1 phase (FIG. 3D). This was opposite to the effects seen in the stable 199bSC1 clone over-expressing miR-199b-5p (see FIG. 1C and FIG. 3C). The effects of restored expression of HES1 on the SP of the stable 199bSC1 clone were also evaluated. When the HES1 transfected cells (GFP positive) were evaluated for their ability to exclude Hoechst dye, they showed a minimum increase in SP, of up to 1.3%. Although higher than that measured for the stable 199b clones (FIG. 3E-H), this was still below the level of SP cells for the wild-type cells (FIG. 11). This is probably due to the short time of re-expression of HES1 after transient transfection, which might not be enough to allow for complete phenotype rescue. We then tried to rescue the effects on the CD133 compartment; however, transient transfection of HES1 in the 199bSC1 clone did not result in a significant increase in CD133+ cells. We believe that this is due to the short transient transfection time, which does not allow a re-organization of Daoy cell hierarchy.

Tumor Growth is Reduced in Xenografts Derived from the Stable 199SC1 Clone.

Figure 4:
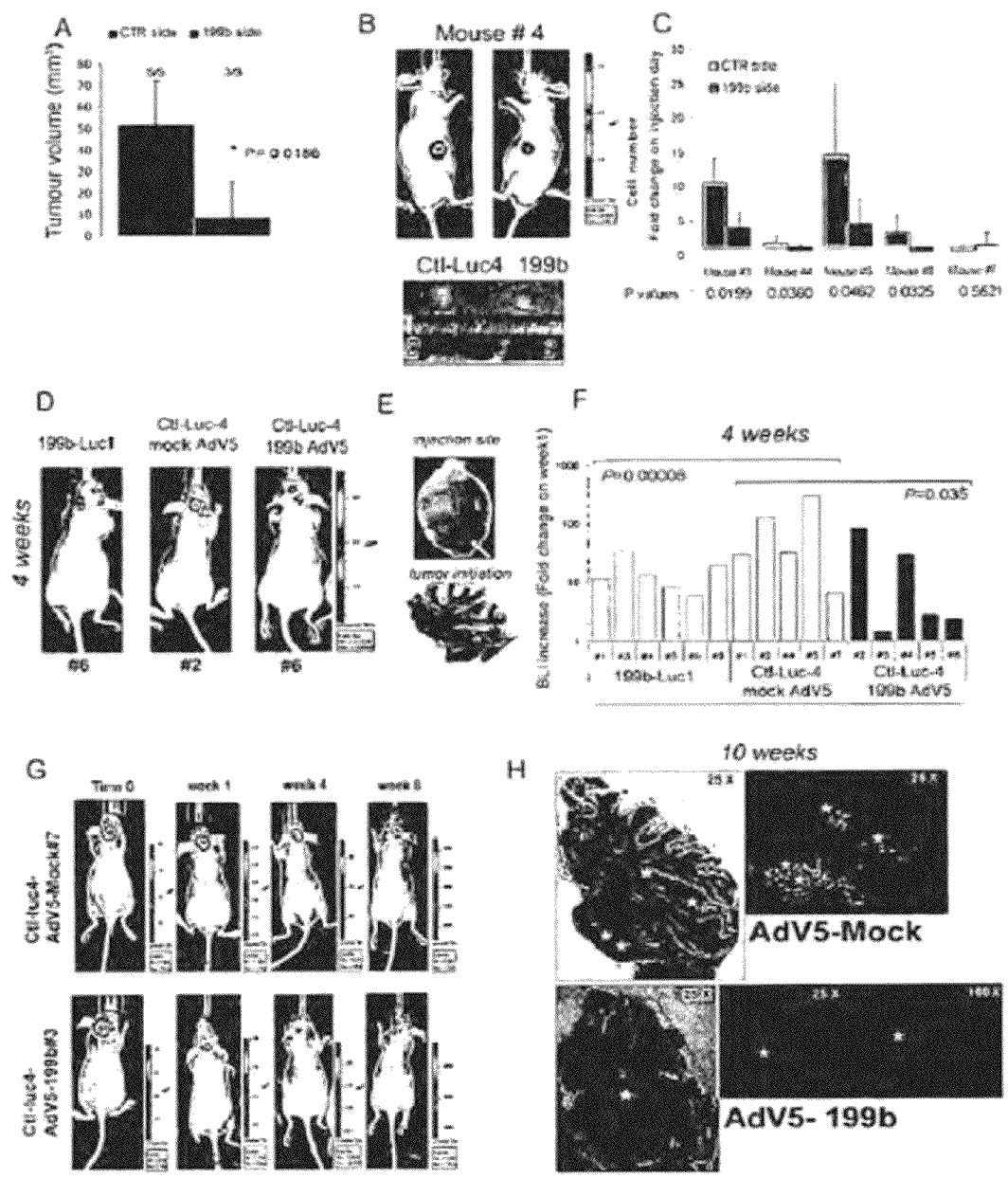

The findings here indicated that miR-199b-5p is a potential inhibitor of tumor formation. Therefore, to investigate the role of miR-199b-5p in an in-vivo tumor model, we stabilized the 199bSC1 and control Daoy clones with an expression vector carrying luciferase cDNA. The clones obtained were tested for luciferase expression levels and also validated for retention of the parental phenotype, in terms of both HES1 and miR-199b-5p expression (see FIG. 12A-D). These stable 199b-Luc1 and Ctl-Luc-4 Daoy clones were then injected into the left and right flanks, respectively, of five athymic nude/nude mice. Tumor growth was evaluated by weekly in-vivo bioluminescence imaging (BLI) of injected mice. At eight weeks, all of the mice showed visible masses in each control flank, while only three flanks injected with 199b-Luc1 showed tumor engrafting. Overall, a significant difference in tumor volumes between control flanks and miR-199b-5p flanks was seen (FIG. 4A). The bioluminescence measurements showed significant reductions in emission for the miR-199b-5p sides during tumor growth, as compared with the control sides (e.g. mouse #4, FIG. 4B). After nine weeks, four out of the five mice showed statistically significant differences in these bioluminescence signals between control sides and miR-199b-5p counter sides (FIG. 4C). Taken together, these data show that miR-199b-5p can impair tumor formation in vivo in athymic nude/nude mice. The xenograft tumors from mouse #5 and mouse #4 were explanted and analyzed for miR-199b-5p and HES1 expression and evaluated histopathologically (FIG. 12 E-H).

To further investigate the ability of miR-199b-5p to regulate MB growth, we injected the 199bSC1 stable clone orthotopically into the fourth ventricle of nude mice of 5 weeks of age (FIG. 4D, E). After four weeks of in vivo non-invasive monitoring tumor growth by bioluminescence imaging (BLI), in mice injected with the 199bSC1 clone the tumor growth was considerably lower than that observed in the control (CTL)-cells-injected side. As further confirmation of these effects, we also injected the CTL cells infected with an adenovirus coding for miR-199b: in agreement with the previous findings, these mice also showed reduced BLI after 4 weeks (FIG. 4F). Further BLI acquisitions after 8 weeks from implantation of the cells are shown in FIG. 4G. At this time, two mice were sacrificed and further analysed for histopathology. Hematoxylin-eosine staining of frozen tissues showed tumor mass in the cerebellum of AdV5-Mock#2 and AdV5-199b#3 injected animals. Serial parallel frozen histological sections were examined by fluorescence microscopy for endogenous green fluorescence protein (GFP) expressed by adenovirus-infected cells. Then, we evaluated HES1 protein expression by immunohistochemistry staining of other paraffin-embedded tissues, using an anti-HES1 antibody. Overall, we assessed the levels of persistence of adenovirus expression in infected cells, as the down-regulation of HES1 expression due to miR199b carrying the adenovirus expression, thus following tumor growth over time by BLI see FIG. 4G-H, and antibodies staining (Hes1, Ki67, Gabra6, Nestin, Math-3) Supplementary FIG. 12 L-M. Then, two additional nude mice (AdV5-Mock#7; AdV5-199b#5) underwent PET-CT studies at 12 weeks post-injection, to assess tumor proliferative activity (FIG. 5A, B). Supplementary acquisition data of bioluminescence with two videos showed the 3D reconstruction of the two mouses injected with AdV5-Mock and with AdV5-199b, respectively (FIG. 14). These analyses showed significant reduction of tumor mass in the AdV5-199b#5 animal, as compared to the AdV5-Mock#7 control mice, with PET-CT analyses also providing tumor volumes (0.024 cm$^3$ versus 0.044 cm$^3$, respectively). Overall, these data indicate a beneficial effect of over-expression of miR199b-5p, as a negative influence on tumor growth of MB cells in this orthotopic xenograft nude-mouse model.

Expression of miR-199b-5p in Human Medulloblastoma Tumors.

To determine whether miR-199b-5p is effectively expressed in healthy human pediatric cerebella, we used 13 control samples obtained from the NICHD Brain and Tissue Bank for Developmental Disorders, at the University of Maryland, USA. We measured miR-199b-5p expression, comparing five cerebellum samples obtained from 0-1-year-old children with six from 13-16-year-old children (FIG. 6A), MiR-199b-5p showed greater expression in the explants from the younger healthy controls (Mann-Whitney test, P=0.006).

To determine whether miR-199b-5p expression has a role in human MB, samples from a cohort of 61 MB patients were analysed (see Experimental Procedures). Indeed, it has already been shown that HES1 protein levels correlate with negative outcome in MB patients [24]. The whole patient population (n=61) was then divided into two groups, as low versus high miR-199b-5p expression, based on the overall median. The distribution of miR-199b-5p expression between non-metastatic (M0) and metastatic (M1, M2 and M3) cases showed that miR-199b-5p expression in the non-metastatic cases was significantly higher than in the metastatic cases (P=0.001, Pearson Chi-Square test; FIG. 6B).

In the subset of patients where follow-up information was available (n=45), the survival curve for the patients who expressed miR-199b at high levels showed a positive trend, with better overall survival than the low-expressing patients. However, the log-rank test of the Kaplan-Meier curves did not show a significant difference (P=0.182; FIG. 6C), probably due to the limited number of patients with long-term follow-up.

These data showing down-regulation of miR-199b-5p in metastatic MBs indicates a mechanism of silencing through epigenetic or genetic alterations. We thus tested expression of miR-199b-5p by real-time PCR in a panel of MB cell lines following induction of de-methylation with 5-aza-deoxycytidine (FIG. 6D). Indeed, two cell lines (Med8 and UV238) showed significant up-regulation of miR-199b-5p, thus supporting the hypothesis of epigenetic control of miR-199b-5p expression. Further studies need to be performed to identify this tuned regulation mechanism of action through epigenetic inactivation of miR199b-5p expression during tumor development.

Supporting Information

Through target prediction analyses, miR-199a-5p and miR-199b-5p were seen to potentially target HES1, with high score values. To determine whether this potential binding translated into efficient HES1 regulation in living cells, we transfected both miRNAs in the HEK-293 cell line (FIG. 9A, B). We cloned the pre-miRNAs into two constructs where expression was driven by the CMV promoter. After 48 h of transient transfection, miR-199b-5p did indeed down-regulate HES1 expression. At this stage, we could exclude effects of miR-199a-5p on HES1 3'UTR in different cell types too.

We then evaluated the expression levels of mature miR-199b-5p using a real-time approach (see Experimental Procedures) in Daoy and D283MED cells (FIG. 9C). MiR-199b-5p showed low expression levels in SH-SY5Y cells, a neuroblastoma cell line, while the Daoy cells expressed more miR-199b-5p. There were also differences in the expression levels of the two miRNAs in the D283MED MB cell line, which was derived from the ascites fluid of a metastatic MB patient, unlike the Daoy cell line [1]. Here, the expression of miR-199b-5p was $10^4$-fold lower when compared to the Daoy cells, potentially reflecting the different tumor cell type origins [2]. The expression of miR-199a* was also evaluated (data not shown), which is also known as miR-199a-3p, and which has recently been linked to the MET proto-oncogene [3]. After over-expression of pre-miR-199a, we did not see over-expression of miR-199a* in Daoy cells. This is probably due to a specific processing of pre-miR-199b-5p towards the production of miR-199a (data not shown). MiR-199b-5p expression was also evaluated in normal human tissues (FIG. 9D): its expression was high in the duodenum and lymph nodes, with lower expression seen in adult (whole) brain and cortex.

To confirm the effects of miR-199b-5p on different MB cell lines, we transiently transfected D283MED cells and evaluated the down-regulation of HES1 by Western blotting. As shown in FIG. 9G, the over-expression of miR-199b-5p led to a decrease in the HES1 protein levels. This effect on HES1 protein translates into a reduction in cell proliferation, as evaluated by the MTS assay (FIG. 10F). In this case, we compared D283MED and ONS76 cell lines transiently transfected with miR-199b-5p; in both cases we saw decreased proliferation, as compared to mock-transfected cells.

So, we asked if miR-199b-5p is involved in the control of cell proliferation at endogenous levels. To answer this, we used a 2-O-methyl-oligoribonucleotide directed against the mature miR-199b-5p sequence (199b-OM), to decrease its endogenous levels. As Daoy cells showed the highest amounts of miR-199b-5p among the MB cell lines tested (data not shown), they were transfected with 199b-OM (FIG. 10G). The cells showed a higher proliferation rate in vitro, compared to the proliferation rate of the Daoy cells transfected with a control OM (a scrambled 2-O-methyl oligoribonucleotide).

Mmu-miR-199b-5p Expression in Developing Cerebellum

To address the question as to how mir199 is expressed during cerebellum development, we made use of the mmu-miR-199b-5p murine homolog and assayed for its expression in the developing mouse cerebellum. We applied the methodology developed for the use of locked nucleic acid probes labeled with digoxygenin (DIG). Embryos at E14.5 and newborn mouse brains at P0 were used in in-situ hybridization experiments, as shown in FIG. 10A. The expression of mmu-miR-199b-5p was compared to that of miR-124a as the control, which is known to be an abundant miRNAs in the central nervous system. The expression of mmu-miR-199b-5p was more diffuse, as compared to miR-124a. Also, mmu-miR-199b-5p expression decreased with development of the cerebellum, while miR-124a retained its expression in the internal granule cell layer (IGL) and in Purkinje neurons. Then, the expression of mmu-miR-199b-5p was evaluated in the mouse cerebellum at different developmental stages, by measuring the levels of mature mRNA and through its expression analyses using real-time PCR. The data showed that even if mmu-miR-199b-5p was expressed at lower levels compared to miR-124a, mmu-miR-199b-5p expression is regulated in development, decreasing from embryonic days 16.5 to the adult developed mouse cerebellum (FIG. 10B).

MiR-199b-5p Regulation of Other Potential Targets.

Among the predicted targets of miR-199b-5p, there is the kinase GSK3-β, a protein involved in signal transduction from the Shh and Wnt pathways, and thus a crucial kinase in the pathways regulating cerebellar cell homeostasis. For this reason, we evaluated the ability of miR-199b-5p to down-regulate GSK3-β using the already obtained stable 199bSC1clone. This clone did not show any significant reductions in the levels of the GSK3-β protein (FIG. 10C). This effect can be explained according to the 3'UTR of GSK3-β not being accessible for binding with miR-199b-5p, as is indeed suggested by the high ΔΔG evaluated by the Pita algorithm (see Table 3; [4]). We also selected three other genes to be tested for their potential regulation by miR-199b-5p: Nanog, NHLH2 and cyclin L1. When down-regulated, these genes could lead to a phenotype similar to that seen in the stable miR-199b-5p clones. We did not detect any down-regulatory effects of miR-199b-5p on these selected gene 3'UTRs (FIG. 10D). More recently, it has been shown that miR-199a* regulates the MET proto-oncogene [3]. Since it shares the same sequence as miR-199b-5p, it will be of interest to check the levels of this proto-oncogene in our analyses, which will be an issue of future studies.

TABLE 3

| Target genes | Gene function | Miranda analysis | | PITA analysis | |
|---|---|---|---|---|---|
| | | Score | P-value | Seed | ΔΔG |
| HES1 | Transcription factor | 18.2355 | 5.80E−03 | 8:0:1 | −8.92 |
| NTRK1 | Neurotrophic tyrosine kinase receptor | 19.4586 | 1.70E−03 | 8:0:1 | 1.21 |
| CCNL1 | Clyclin L1 | 17.4364 | 3.60E−05 | 8:0:0 | −10.28 |
| CDK9 | Cyclin-dependent kinase 9 | 16.488 | 1.40E−04 | 8:0:0 | −5.03 |
| HIRA | HIR histone cell cycle regulation defective homolog A | 16.224 | 2.10E−04 | 8:0:1 | −2.52 |
| HOXC5 | Homeobox protein Hox-C5 | 16.157 | 8.21E−03 | 8:0:1 | 0.09 |
| MAP2K5 | Dual specificity mitogen-activated protein kinase kinase 5 | 16.2892 | 4.35E−02 | 8:0:1 | −4.13 |
| MAP3K12 | Mitogen-activated protein kinase kinase kinase 12 | 15.8078 | 6.10E−03 | 8:0:1 | −6.37 |
| NANOG | Homeobox protein NANOG | 17.3329 | 0.01486 | 8:0:1 | −7.65 |
| NHLH2 | Helix-loop-helix protein 2 (HEN2) | 16.0155 | 4.62E−03 | 8:0:0 | −7.59 |
| OTX1 | Homeobox protein OTX1 | 16.1851 | 2.04E−04 | 8:0:1 | −8.68 |
| GSK3B | Glycogen synthase kinase-3 beta | 16.4041 | 3.80E−02 | 8:0:0 | 0.03 |

Creation of Bioluminescent Daoy Cells Over-Expressing miR-199b-5p for In-Vivo Studies.

Luciferase-based, in-vivo imaging has emerged recently as a powerful tool to investigate the engrafting potential of tumor cells in orthotopic animal models [5]. To determine the role of miR-199b-5p in an in-vivo tumor model, we stabilized the 199bSC1 and control Daoy clones with an expression vector carrying luciferase cDNA. The clones were tested to assess their luciferase expression levels (FIG. 12A, B): these in-vitro experiments showed high correlations between cell numbers and bioluminescent measurements. Thus, this luciferase expression allowed the non-invasive imaging of tumor-associated bioluminescence and quantification of tumor growth. The stable clones obtained were validated for their retention of the parental phenotype, in terms of both miR-199b-5p and HES1 expression, as illustrated in Supplementary FIG. 12C, D. The xenograft from mouse #4 was explanted and processed to determine its morphology, using haematoxylin and eosin staining. The tumors formed on the control side were more invasive and aggressive than those formed on the miR-199b-5p-injected side, as can be seen by the invasion of the former into the muscle tissue (FIG. 12E; black arrows). The staining with an antibody directed against Nestin revealed that the tumor formed on the miR-199b-5p side showed less cells with the characteristic of neural progenitors, in agreement with Notch pathway down-regulation (FIG. 12G, H) [6]. The explants from mouse #5, which formed tumors on both the 199b- and control-injected sides, showed a loss of expression of the transgene (miR-199b-5p), which could be responsible for the recovery of tumor potential (FIG. 12I).

To further characterize the ability of miR-199b-5p to counteract tumor growth in vivo, we established orthotopic implants of Ctl-Luc1 and 199b-Luc4 cells. In addition, we also injected wild-type Daoy cells that were previously infected with a recombinant adenovirus expressing miR-199b-5p (AdV5-199b), followed by in-vivo imaging bioluminescence (BLI technologies), We used both 199b-Luc4- and the AdV-199b-infected cells as controls, and the Ctl-Luc1 clone was then infected with an AdV5-mock virus. The results 4 weeks from injection are shown in FIG. 5, with more BLI analyses of the mice shown at 4 and 8 weeks (FIGS. 4G and 14).

The Daoy Cell Line Treated with DAPT Shows Increased Endogenous Expression of miR-199b and an Embryonic Stem-Cell-Like Gene Expression Signature.

To determine whether we could increase endogenous levels of miR-199b-5p, we treated Daoy cell lines with N—[N-(3,5-difluorophenacetyl)-l-alanyl]-S-phenylglycine t-butylester (DAPT, Sigma-Aldrich), which efficiently blocks the presenilin-secretase complex, and as a consequence, efficiently prevents activation of the Notch response [7,8]. As shown in FIG. 13A, we found that upon treatment with DAPT, the level of miR-199b-5p increased by 9-fold at 12 h. This activation was then followed by rapid inhibition of its expression, within the 24 h of the treatment. These data were then supported by verifying the levels of HES1 using Western blot analyses (FIG. 13B), thus indicating that following miR-199b-5p over-expression, inhibition of the HES1 protein levels was seen. These data prompted us to determine to what extent HES1 loss and miR199 over-expression can influence the gene expression signature of genes involved in embryonic stem (ES) and cancer stem cells upon DAPT treatment.

Following the results presented in one recent study [9], we applied real-time quantitative detection for the expression profiles of the genes (Top-8 list) that were enriched and associated with embryonic stem (ES) cell identity, and the 'stemness' properties of several solid tumors, including breast, bladder, and glioma. Here, we selected markers for stem-cell genes (MB and glioblastoma), such as CD133 and c-Myc, and then genes that are key regulators of ES cell identity: Oct4, KFL5 and Nanog. We also looked at genes associated with adult stem cell/progenitor function, ES and tumor cell proliferation and/or cancer progression. According to these criteria, the gene list comprised: CD133, c-Myc, Oct4, KFL5, Nanog, TCF7L1, HMGA1, HMGB3, ZIC1, MYBL2, TEAD4 and ILF3. As shown in Supplementary FIG. S5C, the expression of CD133 and c-Myc genes was down-regulated in the Daoy cell line induced with DAPT. Then the expression levels of the Oct4, Nanog, KFL5, TCF7L1, HMGA1 HMGB3, ZIC1, MYBL2 and TEAD4 genes were also seen to be down-regulated in Daoy DAPT-induced over-expression of miR-199b-5p, primers and raw 2^DCt values are listed in Tab S3. This thus confirmed that miR-199b-5p up-regulation is concurrent with inhibition of the Notch pathway, which regulates stem-cell populations, as seen by those selected markers that are already known to be involved 'directly' or 'indirectly' in this phenomena. At present, it remains to be determined to what extent the over-expression of miR-199b-5p can be modulated by inhibition of the Notch pathway. These questions will be an issue for future studies.

Additional studies have demonstrated over-expression of PDGFR-A, PDGFR-B and SPARC genes in metastatic MB patients and in MB cell lines [10,11]. We thus also analysed the expression of PDGFR-A, PDGFR-B and SPARC genes in the Daoy cell line model as presented above, with its up-regulation of endogenous miR199b upon treatment with DAFT. As shown in FIG. 13D, the expression of PDGFR-B and SPARC were down-regulated in the Daoy cell line treated with DAPT, as compared with vehicle only treatment, while low up-regulation of PDGFR-A also seen. At this time, it remains to be determined if this low increase in the expression of PDGFR-A through the RAS/MAPK pathway will be sufficient to drive the metastatic potential of MB cells overexpressing miR-199b-5p; this is an opposite effect to that we obtained by verifying expression of miR199b-5p in tumors. These results are also somehow contradictory with the data in the literature, although in framework of an erratum [11], the over-expression of PDGFR-A found in MB metastatic tumors was miss-judged due to an incorrect sequence and probe annotation by GenBank and Affymetrix: although GenBank sequence J03278 includes the complete coding region of PDGFR-B, the locus was given as 'PDGFRA', and Affymetrix probe 1771 was annotated as 'J03278 HUMPDGFRA Human platelet-derived growth factor (PDGF) receptor mRNA'. Within these new reported data[10], PDGFR-B was seen to be up-regulated in metastatic MB tumors. These latest results are in line with what we have seen in our Daoy cells lines, where over-expression of miR-199b-5p upon DAPT treatment induced down-regulation of expression of PDGFR-B and SPARC. This in turn correlates with the loss of expression of miR199b-5p in metastatic patients, and definitively strengthens the importance of miR-199b-5p expression and its involvement in MB cancer development, impairing their metastatic potential. Finally, the data here presented confirmed the role of miR-199b-5p over-expression by linking its main function to inhibiting ES and cancer stem cell maintenance operated by genes already involved in these mechanisms of action.

Very recently, a specific expression pattern from childhood MB patients showed nine miRNAs, which included miR-199b-5p, also clustered with ErbB2- and/or c-Myc-over-expressing tumors [12]. In particular, they showed higher expression of miR-135a and b, miR-10b, miR-125b and miR-153, while miR-199b showed lower expression in these ErB2-positive patients. Of note Gilbertson et al. [13] have show that ErbB2-HER4-positive tumors behave as independent prognostic markers in childhood MB, and in particular Erb-2 is a worse prognostic marker given its negative survival effect in MB. Overall, those results from the literature strengthen further the importance of mir199b-5p, the expression of which is down-regulated in MB tumors and associated with aggressiveness of these Erb-2-positive cohorts.

High-Resolution Molecular Imaging by Small-Animal PET and SPECT-CT Analyses.

Animal Preparation and PET/CT Imaging

The mice were kept in a ventilated cage (26° C.) for 1 h prior to imaging studies. Anesthesia was performed with intraperitoneal administration of a mixture of ketamine (100 mg/kg) and xylazine (10 mg/kg) (injection volume, 100 µl/10 g). PET was performed 1 h after administration of 3'-deoxy-3'-[$^{18}$F]fluorothymidine ([$^{18}$F]FLT), a marker of tumor proliferation (50 µL; 7.4 MBq; scan time, 18 min), in a lateral caudal vein, using an animal PET scanner (GE Healthcare eXplore Vista, FWHM 1.6 mm). High resolution CT studies (GE Healtcare eXplore Locus; spatial resolution, 45 µm) were performed within 24 h from the PET.

Data Analysis

Maximum (SUVmax) and mean (SUVmean) standardized uptake values (SUVs) were calculated from the PET studies (SUV=tissue activity (MBq/cc)/[injected dose (MEN)/body weight (g)]). The PET/CT images were post-processed to obtain multiplanar reconstructions (MPRs), maximum intensity projections (MIPs), 3D volume rendering, and fusion images, using Osirix 3.3 (MAC OS 10.5 operating system). Additional 3D reconstructions were obtained using Micro-View (GE eXplore Locus).

Lesion volumes were calculated from PET data using in-house-developed software (based on IDL, ITT Vis Inc), by summarizing all spatially connected voxels with SUV>50% SUVmax. Lesion profiles defined with these procedures were used for ROI-based comparison between AdV5-Mock and AdV5-199b.

Discussion

The interconnections between the signaling pathways altered in MB remain largely unknown, and it is still difficult to define specific patient stratification according to risk classes that would lower therapy-linked mortality and morbidity. In the present study, we have identified a mechanism of HES1 gene regulation via the miRNA miR-199b-5p. HES1 is a key regulator of cerebellum development, as indicated by recent findings that treatment of cerebellar granule cells with Shh increases the levels of HES1 [20]. This suggests that HES1 is a transcriptional target of both the Shh and Notch2 signaling cascades.

We report here a novel level of regulation of HES1 expression that is driven by miR-199b-5p, which binds to the HES1 3'UTR and leads to unproductive translation. Of note, we have also investigated the actions of miR-199b-5p on a reporter construct fused with the 3'UTR of NHLH2, cyclin L1 and Nanog (FIG. 10D). Among the predicted targets for miR-199b-5p, which were obtained using two different algorithms (Table 3), these genes were possible candidates related to the phenotype obtained after miR-199b over-expression. Nonetheless, we did not obtain down-regulation of reporter activity when tested under the same conditions where we obtained effects on HES1 3'UTR. Furthermore, the stable 199bSC1 clone has a GSK3-β protein level comparable to the control. Of note, when analyzed according to the Pita algorithm, the value of ΔΔG for the binding of miR-199b-5p to the 3'UTR of GSK3-β is very high, indicating poor accessibility to the 3'UTR [41] (Table 3). Recently it has also been shown that miR-199a*, which has the same sequence as miR-199b-5p, is involved in caspase activation by potentially acting through Met proto-oncogene down-regulation [42]. It will be of interest for future studies to also determine the down-regulation of this target by miR-199b, even if it appears unlikely because of the lack of induction of apoptosis after miR-199b over-expression in our cellular systems.

The analysis of the over-expressing miR-199b-5p clones suggested that miR-199b-5p can impair the proliferation and engrafting potential of MB cells. Indeed loss of Cyclin D1 in over-expressing miR-199b-5p clones are a reminder of the similar effects seen in Ccnd1−/− mice, which have decreased early GNP proliferation and early ataxia as a consequence of a delay in acquiring normal cerebellar function, thus affecting progression of the pre-neoplastic lesions to MBs [43].

Our data are also in agreement with the in-vivo data reported from murine cells genetically knocked down for Hes1. While the effects of miR-199b-5p could be explained by triggering of apoptosis, our cytofluorimetric assays suggested that impairment of MB cell proliferation is not linked to extensive apoptosis of cells over-expressing miR-199b-5p (see cell cycle assay on FIG. 1A). This is in agreement with reported data for neural progenitors obtained from Hes1−/− mice, where apoptotic indications were only seen in restricted cell types [22].

The correlation that we show between miR-199b-5p and tumor M stage indicates that miR-199b-5p expression levels can be investigated concomitant with tumor resection. This will allow identification of a subset of patients who should develop an aggressive tumor and have future metastasis formation, noting that disseminated disease is the most powerful independent factor associated with poor survival. Despite the correlation with M status, the over-expression of miR-199b-5p did not lead to a decrease in cell motility of Daoy cells (FIG. 10E). This may well be due to the extremely high motility of Daoy cells, indicating that to overcome this phenotype, a further step beyond regulation of the Notch pathway needs to take place. However, of note, the expression of PDGFR-B and SPARC, two genes recently correlated with metastatic MB [44,45], is reduced in the presence of over-expression of miR-199b-5p, as we show in FIG. 13D and describe in Supplementary Materials.

Figure 6:
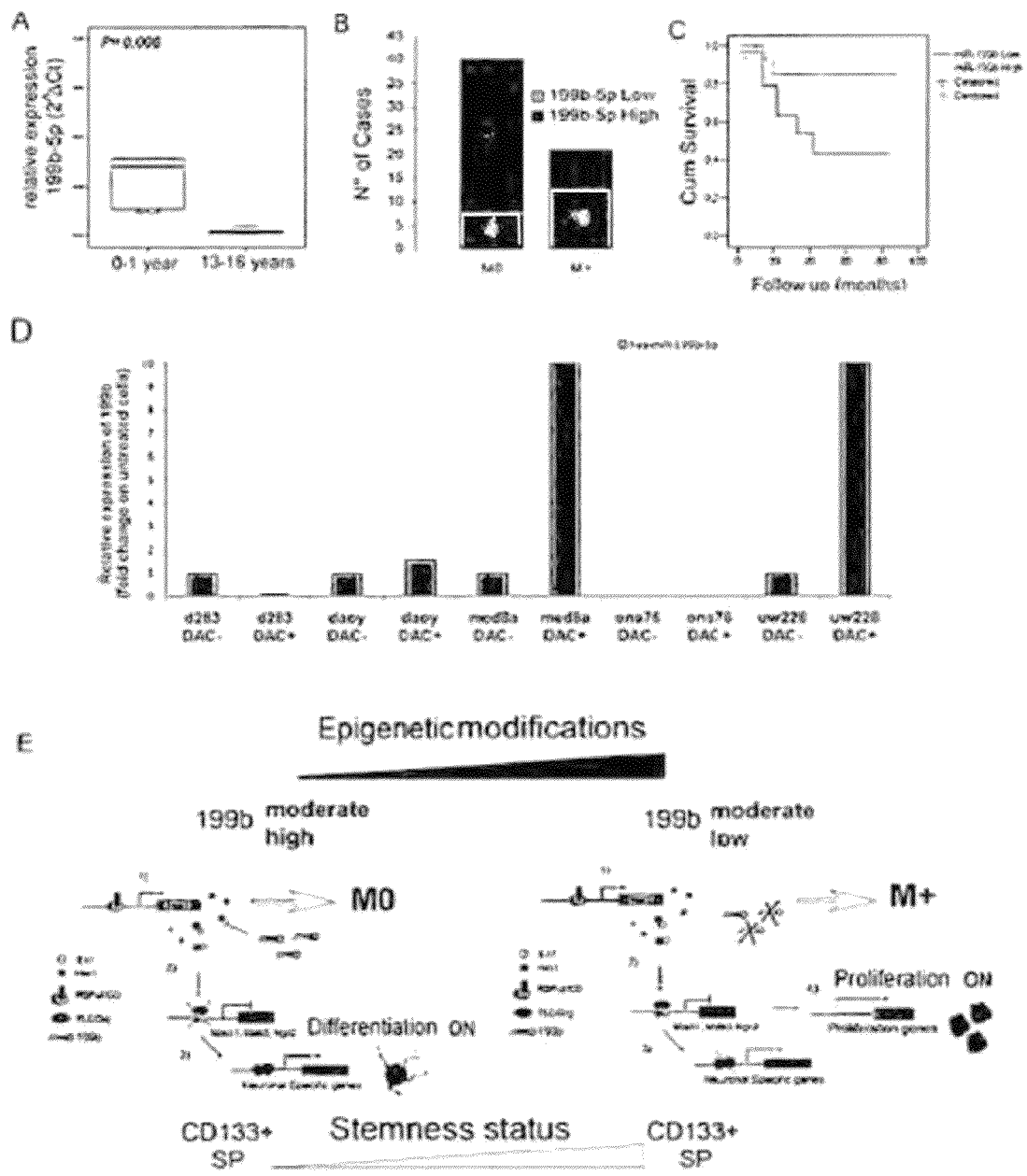
Figure 7:
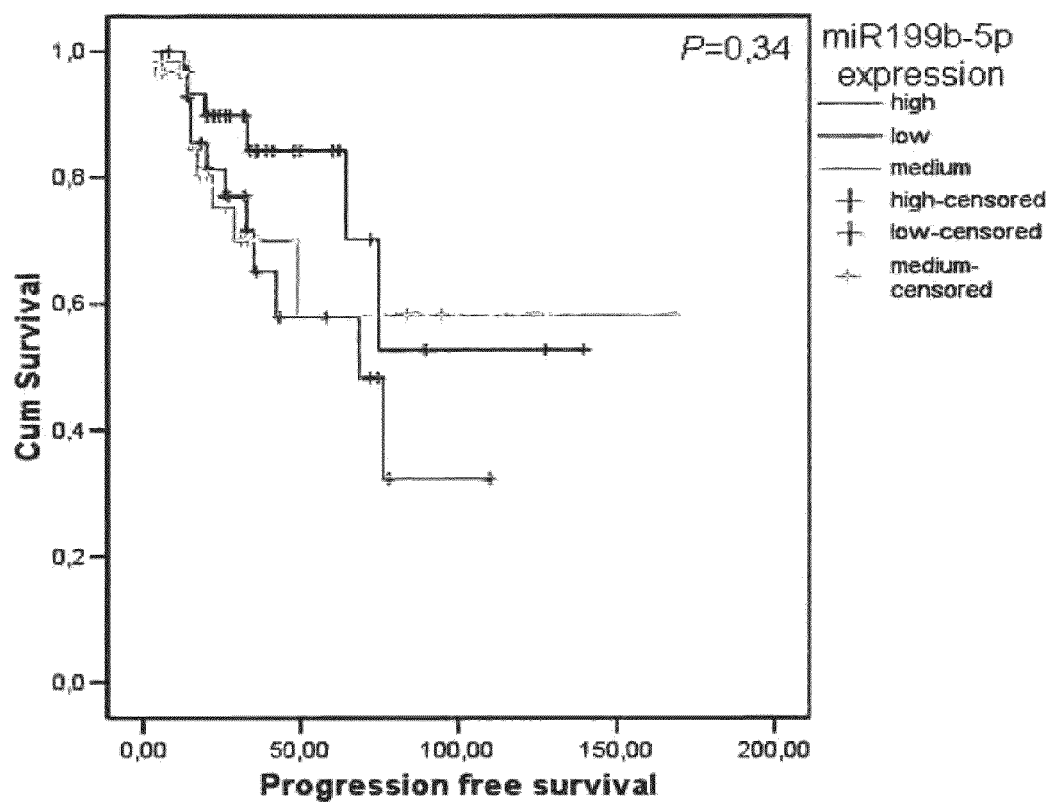
FIG. 7 shows the association of miR199b-5p expression with the survival of MB patients: the Kaplan-Meier analysis shows the patients with low level of miR199b-5p in respect to patients with high levels (33° and 66° percentile) of Mir-199b-5p (follow-up data for 90/108 patients available).
Figure 8:
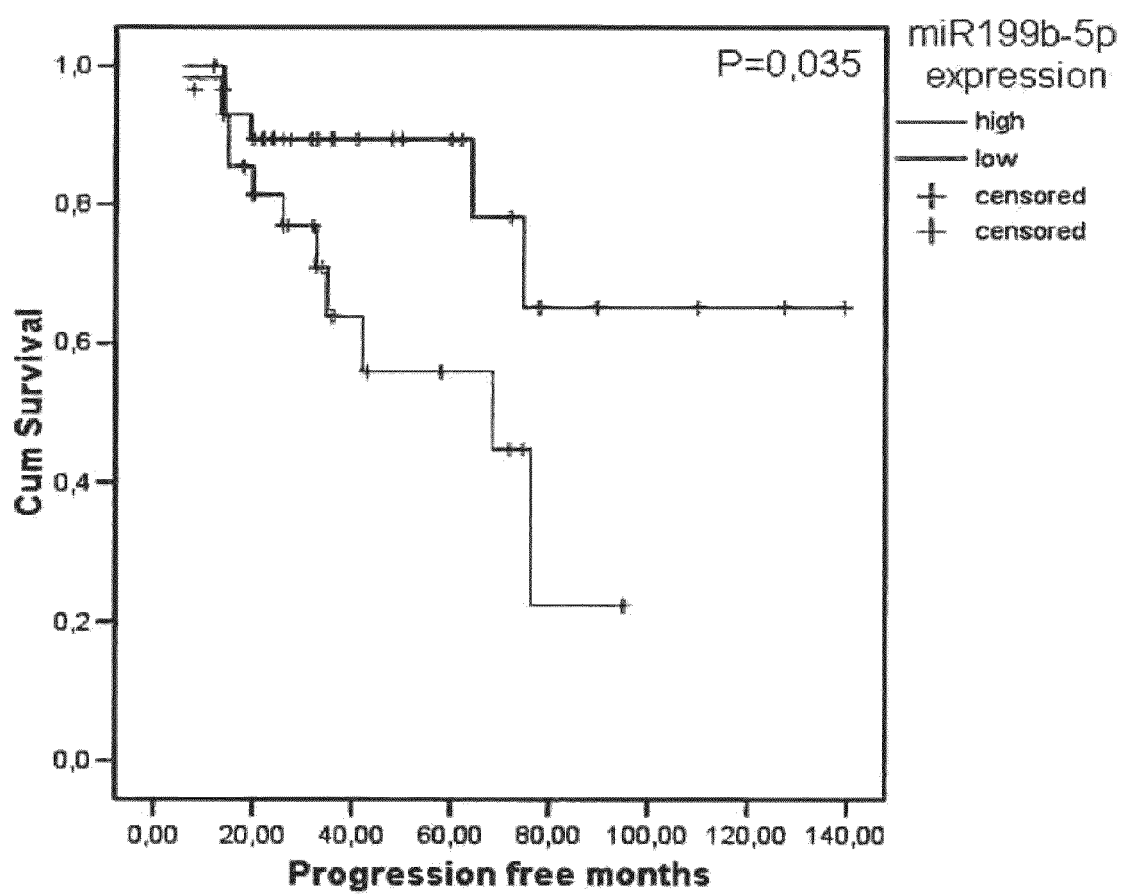
FIG. 8 shows the association of miR199b-5p expression with the survival of MB patients: the Kaplan-Meier analysis shows the patients with low level of miR199b-5p in respect to patients with high levels (33° and 66° percentile) of Mir-199b-5p (follow-up data for 90/108 patients available).

In the light of our data on the regulation of the Notch pathway via miR-199b-5p modulation, it will be of interest to focus future studies on the role of Notch-regulated genes in metastatic MB patients. Additionally, developing mouse models that better reproduce the human disease is an important task. Within this scenario, the findings that the homozygous Smo/Smo mouse model has leptomeningeal spread confirms involvement of the Notch pathway in regulation of MB growth [25,46]. As shown in FIG. 6 and in Table 2, we show great variability in the miR-199b-5p expression levels, which might be due to genetic chromosomal alterations or epigenetic silencing in a subset of patients with worse outcome. Our data on a panel of MB cell lines (see FIG. 6D) support this last hypothesis. The reason why some of the MB cell lines do not respond to the treatment with increasing miR-199b could be due to genetic loss of the gene itself, or to a strict cell-type regulation of miR-199b expression, reflecting the different origins of the cell lines.

At present, there is growing interest in the elucidation of the mechanisms that confer unique properties to the 'cancer stem cells' [47]. Recently, it was shown that glioblastoma CD133+ cells have a better chance of survival after ionizing radiation, through the induction of the repair of damaged DNA [48]. Indeed, Daoy cells expressing the CD133 antigen are radio-resistant, thus supporting the hypothesis that Daoy cells represent a model for the study of a tumor stem-cell compartment [49]. Here miR-199b-5p can influence this side population and the CD133+ population of Daoy cells, namely the cancer stem cells.

Together with CD133, we also evaluated the expression levels of several cancer stem-cell genes that have recently been shown to be correlated with the aggressiveness of solid tumors; as shown in Supplementary FIG. S5B, the expression of these genes is in agreement with an overall reduction in the 'stemness' phenotype of Daoy cells treated with N—[N-(3, 5-difluorophenacetyl)-l-alanyl]-S-phenylglycine t-butylester (DAPT). This prevents activation of the Notch response (see Supplementary Materials), thus blocking the presenilin-secretase complex and enhancing miR199b-5p expression [50,51]. To date, this is the first report that expression of an miRNA can deplete this tumor cell compartment, indicating an interesting therapeutic approach for the targeting of these cells in brain tumors.

There is a strong indication from published series that children with medulloblastoma presenting at over 3 years of age benefit greatly from radiotherapy, but the treatment of younger children remains a challenge. The absence of significant differences in survival rates between patients with total or subtotal excision of MB supports the view that the total excision of MB can be avoided when the risk for potential neurological deficits is high. Recent trials have demonstrated a beneficial effect of chemotherapy, although this was not universally seen [52,53]. Here, we envisage the use and delivery of miR199b-5p in situ into the cerebellum of MB-affected children under 3 years of age (and positive to HES1), to thus impair the maintenance of the tumor-initiating CD133+ cancer cells. Combined with chemotherapy, and with the potential to abrogate radiotherapy and avoid brain damage due to total tumor excision, this should provide an overall improvement in the present treatments for MB. Thus we foresee the possibility of treating MBs with the use of encapsulated stable nucleic acid lipid particles (SNALP). These have been demonstrated to be effective in non-human primates for systemic delivery, and would by-passing the blood-brain barrier using encapsulated nano-particles containing agomir 199b-5p molecules [54]. How these gene-therapy approaches will progress further will be an issue for future pre-clinical animal studies.

As illustrated in our model (FIG. 6E), we picture two different expression levels of miR-199b-5p in M0 and M+ patients, which might be due to epigenetic regulation during carcinogenesis. In our 'moderate high' model, an increase in miR-199b-5p expression represses HES1, which then leads to an increase in pro-neural bHLHs gene expression, driving the cell towards differentiation processes. In the 'moderate low' model, miR-199b-5p expression is lowered due to epigenetic control mechanisms, and then HES1 is over-expressed, leading to cell proliferation and induction of the SP and hence an increase in CD133+ cells. As for many other transcription factors, HES1 is a point of integration between and among different signal transduction pathways, and its balance of expression determines fundamental cell decisions, such as whether or not to start a differentiation program. With this scenario, miR-199b-5p can be seen as part of the complex Notch signal-transduction pathway, as a fine tuner of the levels of expression of the HES1 bHLH transcription factor. These phenomenon could be considered to occur in a variety of tissues and cancers where an activated Notch pathway is involved.

EXAMPLE 2

Evaluation of the Effects of the Treatment of MB, Colon Carcinoma and Breast Carcinoma Cell Lines with the SNALP miR199b-5p Material and Methods:
SNALP Formulation
SNALP (stable nucleic acid lipid particles) technology used in other work (71-73) were formulated for the mir 199b-5p and its relative control scramble (named CTR in the figures) by different lipids provided by Lipoid GMBH (Cam, Switzerland). Analytical grade solvent from Carlo Erba Reagenti were used. In the extrusion process, Nucleopore Track Membrane 25 mm polycarbonate filters were from Whatman (Brentford, UK). Membranes for dialysis, the salts and all the other chemicals were purchased from Sigma-Aldrich (Milan, Italy).

SNALPs were prepared by a lipid mix composed of the ionisable aminolipid dioleoyldimethylammonium propane (DODAP), associated with other neutral lipids, i.e. distearoylphosphatidylcholine (DSPC), egg phosphatidylcholine (EPC) and distearoylphosphatidylethanolamine-polyethylenglycol 2000 ($DSPE_{2000}$). The encapsulation of miRNA into SNALPs were chieved by hydration of a lipid layer with an aqueous solution of miRNA. The resulting suspension was passed 10 times through three stacked 100 nm polycarbonate filters by using a Thermobarrel Extruder Systems (Northern. Lipids Inc., Vancouver, BC, Canada). The preparation was dialyzed against 300 mM citrate buffer, pH 4.0 for approximately 1 h to remove excess ethanol; then further dialyzed against HBS (20 mM HEPES, 145 mM NaCl, pH 7.6) for 12-18 h to remove the citrate buffer, neutralize the DODAP and release any miRNA associated with the surface of the vesicles. Non-encapsulated ODN were removed by DEAE-Sepharose CL-6B column chromatography. Experimental conditions, i.e. the concentration on miRNA in the aqueous solution and the ratio between the different lipids, were optimized in order to encapsulate high amounts of miRNA into the vesicles. After preparation, SNALPs were solubilized in organic solvent and miRNA will be extracted in an aqueous solution and quantified by UV spectrophotometry. Particle mean diameter and size distribution of the different SNALP formulation will be investigated by photon correlation spectroscopy (N5 Beckmann Coulter, Miami). The SNALP zeta potential were determined by using M3-PALS technology (Zetasizer Nano, Malvern, Worcestershire, UK). MiRNA/lipid stealth nanocomplexes was prepared by mixing of a suspension of cationic liposomes based on (N-[1-(2,3-Dioleoyloxy)propyl]-N,N,Ntrimethylammonium methylsulfate (DOTAP)/cholesterol or DOTAP/cholesterol/$DSPE-PEG_{2000}$ with an aqueous solution containing protamine, and an aqueous solution of calf thymus DNA and miRNA or only miRNA, followed by incubation at room temperature for 10-15 min. In the case of liposome based on DOTAP/cholesterol, the resulting particles were then incubated with a micelle dispersion of DSPE-PEG at 50° C. for 10-15 min. NP was allowed to stand at room temperature for 10 min. The percentage of complexed miRNA, was determined by ultracentrifugation of the complexes and UV analysis of the supernatant. Formulation conditions, i.e. concentration of miRNA in the initial aqueous solution, presence of protamine, amount of cationic lipid used, was optimized in order to obtain the higher complexation efficiency. Particle mean diameter and size distribution of the nanocomplexes was investigated by photon correlation spectroscopy, while zeta potential was determined by M3-PALS technology.

The sequence of the oligonucleotide miR199b-5p in the SNALP e: CCCAGUGUUUAGACUAUCUGUUC (SEQ ID NO:11) and its relative sequence scramble CTR: gguuguaugcauucccuaucuac (SEQ ID NO:12).

Proliferation Assay MTS

Proliferation assay (MTS) was made by kit CellTiter96 AQueous Non-Radioactive Cell Proliferation Assay (Promega) for 72 h. The cell lines daoy, MDA-231T and 4t1 treated with the control SNALP and with the miR 199b-5p were transferred in 96 multiwell at the concentration of 1000 and 3000 cells (daoy, MDA-231T and 4t1, respectively) in 100 µl of complete medium. For each experimental point were done 5 replicates. After 24, 48 e 72 h in each well was added 20 µl of 5× solution. After 4 h was read the absorbance of the formazane at 490 nm by Multilabel counter Victor3 (Perkin Elmer).

Apoptosy Assay

The apoptosis assay in the daoy, MDA-231T and 4t1 treated with control SNALP and miR199b-5p SNALP were made by FACSCalibur (Becton Dickinson, San Jose, Calif.) with the software CELL Quest version 3.3. The Annexin V analysis was made by antibody Miltenyi Biotec (Auburn, Calif.). The cells were stained with Propidium iodure and then incubated with an anti-Annexin V anticorpo FITC (Miltenyi Biotec), for 10 min in the dark at 4° C. The cells were then washed with PBS.

Western Blotting Hes1: see Below

RT Syber Green 199b and CD133: see Below

Cell Culture

The murine breast carcinoma cell line 4T1 was, obtained by the American Type Culture Collection (reference 74, ATCC, Manassas, Va.) and was subculture in Dulbecco's modified Eagle's medium (DMEM; Sigma) supplemented with 10% FBS, 10 U/ml penicillin e 0.1 mg/ml streptomycin (Celbio Pero, Milan, Italy). The cell lines HT29 (human colon carcinoma) and MDA-231T (human breast carcinoma) were obtained by the American Type Culture Collection (ATCC, Manassas, Va.) and maintained in Dulbecco's modified Eagle's medium (DMEM; Sigma) with 10% FBS, 10 U/ml penicillin and 0.1 mg/ml streptomycin (Celbio Pero, Milan, Italy).

Results

MiR 199b-5p Carried by SNALP in Medulloblastoma, Breast Carcinoma and Colon Carcinoma Cell Lines with Evaluation of Toxicity and of the Target Hes1 Inhibition.

The mature form of miR199b-5p (ribonucleotide sequence) was formulated by SNALP as described in material and methods with the relative control. The Daoy, MDA231T, HT29 and 4T1 cell lines were treated with 1 µg of oligonucleotide and was evaluated the vitality by proliferation assay MTS (FIGS. 17A e 18A). As showed in FIGS. 17A, 18A, 19A-B, the lines, showed a decreased proliferation rate at 24, 48 e 72 h after the treatment with miR199b-5p SNALP in respect with the control. After 72 h of treatment, the expression of the miR199b-5p was increased in both the cell lines (FIGS. 17B e 18B). The toxicity of the treatment was evaluated by Annexin V analysis after 72 h of treatment (FIGS. 17C e 18C). As showed in FIGS. 17C and 18C both the cell lines did not showed differences in the apoptosis levels between the control and the miR199b-5p. Furthermore, after 72 h of treatment, the Hes1 expression was evaluated by western blotting as showed in FIGS. 17D e 18D. The over-expression of the miR199b-5p by SNALP showed the reduction of Hes1, demonstrating the effectiveness of the treatment.

Expression of the miR199b-5p in Breast and Colon Carcinoma Tissues

The expression of the miR199b-5p was evaluated in breast (29 tissues) and colon carcinoma (13 tissues). As showed in FIGS. 20 and 21 the expression levels of miR199b-5p are lower in carcinoma tissues in respect to healthy controls, demonstrating that also in these tumors the miR199b-5p is silenced during the tumor progression. The expression levels of the gene Cd133 is also lower in healthy controls in respeact to carcinoma tissues, because it is a cancer stem cells marker.

REFERENCES

1. Bartel D P (2004) MicroRNAs: genomics, biogenesis, mechanism, and function. Cell 116: 281-297.

2. Hammond S M (2006) MicroRNAs as oncogenes. Curt Opin Genet Dev 16: 4-9.
3. O'Donnell K A, Wentzel E A, Zeller K I, Dang C V, Mendell J T (2005) c-Myc-regulated microRNAs modulate E2F1 expression. Nature 435: 839-843.
4. Calin G A, Dumitru C D, Shimizu M, Bichi R, Zupo S, et al. (2002) Frequent deletions and down-regulation of micro-RNA genes miR15 and miR16 at 13q14 in chronic lymphocytic leukemia. Proc Natl Acad Sci USA 99: 15524-15529.
5. Ciafre S A, Galardi S, Mangiola A, Ferracin M, Liu C G, et al. (2005) Extensive modulation of a set of microRNAs in primary glioblastoma. Biochem Biophys Res Commun 334: 1351-1358.
6. Michael M Z, SM O C, van Hoist Pellekaan N G, Young G P, James R J (2003) Reduced accumulation of specific microRNAs in colorectal neoplasia. Mol Cancer Res 1: 882-891.
7. Fabbri M, Garzon R, Cimmino A, Liu Z, Zanesi N, et al. (2007) MicroRNA-29 family reverts aberrant methylation in lung cancer by targeting DNA methyltransferases 3A and 3B. Proc Natl Acad Sci USA 104: 15805-15810.
8. Ma L, Teruya-Feldstein J, Weinberg R A (2007) Tumour invasion and metastasis initiated by microRNA-10b in breast cancer. Nature 449: 682-688.
9. Gilbertson R J, Ellison O W (2008) The origins of medulloblastoma subtypes. Annu Rev Pathol 3: 341-365.
10. Buhren J, Christoph A N, Buslei R, Albrecht S, Wiestler O D, et al. (2000) Expression of the neurotrophin receptor p75NTR in medulloblastomas is correlated with distinct histological and clinical features: evidence for a medulloblastoma subtype derived from the external granule cell layer. J Neuropathol Exp Neurol 59: 229-240.
11. Katsetos C D, Krishna L, Frankfurter A, Karkavelas G, Wolfe D E, et al. (1995) A cytomorphological scheme of differentiating neuronal phenotypes in cerebellar medulloblastomas based on immunolocalization of class III beta-tubulin isotype (beta III) and proliferating cell nuclear antigen (PCNA)/cyclin. Clin Neuropathol 14: 72-81.
12. Marino S (2005) Medulloblastoma: developmental mechanisms out of control. Trends Mol Med 11: 17-22.
13. MacDonald T J (2008) Aggressive infantile embryonal tumors. J Child Neurol 23: 1195-1204.
14. Yang S Y, Wang K C, Cho B K, Kim Y Y, Lim S Y, at al, (2005) Radiation-induced cerebellar glioblastoma at the site of a treated medulloblastoma: case report. J Neurosurg 102: 417-422.
15. Patrice S J, Tarbell N J, Goumnerova L C, Shrieve D C, Black P M, at al. (1995) Results of radiosurgery in the management of recurrent and residual medulloblastoma. Pediatr Neurosurg 22: 197-203.
16. Kombogiorgas D, Sgouros S, Walsh A R, Hockley A D, Stevens M, et al. (2007) Outcome of children with posterior fossa medulloblastoma: a single institution experience over the decade 1994-2003. Childs Nery Syst 23: 399-405.
17. Huntly B J, Gilliland D G (2005) Cancer biology: summing up cancer stem cells. Nature 435: 1169-1170.
18. Singh S K, Clarke I D, Hide T, Dirks P B (2004) Cancer stem cells in nervous system tumors. Oncogene 23: 7267-7273,
19. Yang Z J, Ellis T, Markant S L, Read T A, Kessler J D, et al. (2008) Medulloblastoma can be initiated by deletion of Patched in lineage-restricted progenitors or stem cells. Cancer Cell 14: 135-145.
20. Solecki D J, Liu X L, Tomoda T, Fang Y, Hatten M E (2001) Activated Notch2 signaling inhibits differentiation of cerebellar granule neuron precursors by maintaining proliferation. Neuron 31: 557-568.
21. Ishibashi M, Moriyoshi K, Sasai Y, Shiota K, Nakanishi S, et al. (1994) Persistent expression of helix-loop-helix factor HES-1 prevents mammalian neural differentiation in the central nervous system. Embo J 13: 1799-1805.
22. Ishibashi M, Ang S L, Shiota K, Nakanishi S, Kageyama R, et al. (1995) Targeted disruption of mammalian hairy and Enhancer of split homolog-1 (HES-1) leads to up-regulation of neural helix-loop-helix factors, premature neurogenesis, and severe neural tube defects. Genes Dev 9: 3136-3148.
23. Nakamura Y, Sakakibara S, Miyata T, Ogawa M, Shimazaki T, et al. (2000) The bHLH gene hes1 as a repressor of the neuronal commitment of CNS stem cells. J Neurosci 20: 283-293.
24. Fan X, Mikolaenko I, Elhassan I, Ni X, Wang Y, et al. (2004) Notch1 and notch2 have opposite effects on embryonal brain tumor growth. Cancer Res 64: 7787-7793.
25. Hallahan A R, Pritchard J I, Hansen S, Benson M, Stoeck J, et al. (2004) The SmoA1 mouse model reveals that notch signaling is critical for the growth and survival of sonic hedgehog-induced medulloblastomas. Cancer Res 64: 7794-7800.
26. Leung C, Lingbeek M, Shakhova O, Liu J, Tanger E, et al. (2004) Bmi1 is essential for cerebellar development and is overexpressed in human medulloblastomas. Nature 428: 337-341.
27. Griffiths-Jones S (2004) The microRNA Registry. Nucleic Acids Res 32: D109-111.
28. Yanaihara N, Caplen N, Bowman E, Seike M, Kumamoto K, et al. (2006) Unique microRNA molecular profiles in lung cancer diagnosis and prognosis. Cancer Cell 9: 189-198.
29. Sandberg A A (2002) Cytogenetics and molecular genetics of bladder cancer: a personal view. Am J Med Genet. 115: 173-182.
30. Gramantieri L, Ferracin M, Formari F, Veronese A, Sabbioni S, et al. (2007) Cyan G1 is a target of miR-122a, a microRNA frequently down-regulated in human hepatocellular carcinoma. Cancer Res 67: 6092-6099.
31. Jiang J, Gusev Y, Aderca I, Mettler T A, Nagorney D M, et al. (2008) Association of MicroRNA expression in hepatocellular carcinomas with hepatitis infection, cirrhosis, and patient survival. Clin Cancer Res 14: 419-427.
32. Murakami Y, Yasuda T, Saigo K, Urashima T, Toyoda H, et al. (2006) Comprehensive analysis of microRNA expression patterns in hepatocellular carcinoma and non-tumorous tissues. Oncogene 25: 2537-2545.
33. Izant J G, McIntosh JR (1980) Microtubule-associated proteins: a monoclonal antibody to MAP2 binds to differentiated neurons. Proc Natl Acad Sci USA 77: 4741-4745.
34. Li X N, Parikh S, Shu Q, Jung H L, Chow C W, et al. (2004) Phenylbutyrate and phenylacetate induce differentiation and inhibit proliferation of human medulloblastoma cells. Clin Cancer Res 10: 1150-1159.
35. Hatakeyama J, Bessho Y, Katoh K, Ookawara S, Fujioka M, et al. (2004) Hes genes regulate size, shape and histogenesis of the nervous system by control of the timing of neural stem cell differentiation. Development 131: 5539-5550.
36. Fan X, Matsui W, Khaki L, Stearns D, Chun J, et al. (2006) Notch pathway inhibition depletes stem-like cells and blocks engraftment in embryonal brain tumors. Cancer Res 66: 7445-7452.
37. Kondo T, Setoguchi T, Taga T (2004) Persistence of a small subpopulation of cancer stem-like cells in the C6 glioma cell line. Proc Natl Acad Sci USA 101: 781-786.
38. Goodell M A, Brose K, Paradis O, Conner A S, Mulligan R C (1996) Isolation and functional properties of murine hematopoietic stem cells that are replicating in vivo. J Exp Med 183: 1797-1806.

39. Singh S K, Hawkins C, Clarke I D, Squire J A, Bayani J, et al. (2004) Identification of human brain tumour initiating cells. Nature 432: 396-401.
40. Eberhart C G (2007) In search of the medulloblast: neural stem cells and embryonal brain tumors. Neurosurg Clin N A m 18: 59-69, viii-ix.
41. Kertesz M, Iovino N, Unnerstall U, Gaul U, Segal E (2007) The role of site accessibility in microRNA target recognition. Nat Genet. 39: 1278-1284.
42. Kim S, Lee U J, Kim M N, Lee E J, Kim J Y, et al. (2008) MicroRNA miR-199a* regulates the MET proto-oncogene and the downstream extracellular signal-regulated kinase 2 (ERK2). J Biol Chem 283: 18158-18166.
43. Pogoriler J, Millen K, Utset M, Du W (2006) Loss of cyclin D1 impairs cerebellar development and suppresses medulloblastoma formation. Development 133: 3929-3937.
44. Gilbertson R J, Clifford S C (2003) PDGFRB is overexpresed in metastatic medulloblastoma. Nat Genet. 35: 197-198.
45. MacDonald T J, Brown K M, LaFleur B, Peterson K, Lawlor C, et al. (2001) Expression profiling of medulloblastoma: PDGFRA and the RAS/MAPK pathway as therapeutic targets for metastatic disease. Nat Genet. 29: 143-152.
46. Hatton B A, Villavicencio E H, Tsuchiya K D, Pritchard J I, Ditzler S, et al. (2008) The Smo/Smo model: hedgehog-induced medulloblastoma with 90% incidence and leptomeningeal spread. Cancer Res 68: 1768-1776.
47. Fan X, Eberhart C G (2008) Medulloblastoma stem cells, J Clin Oncol 26: 2821-2827.
48. Bao S, Wu Q, McLendon R E, Hao Y, Shi Q, et al. (2006) Glioma stem cells promote radioresistance by preferential activation of the DNA damage response. Nature 444: 756-760.
49. Blazek E R, Foutch J L, Maki G (2007) Daoy medulloblastoma cells that express CD133 are radioresistant relative to CD133-cells, and the CD133+ sector is enlarged by hypoxia. Int J Radiat Oncol Biol Phys 67: 1-5.
50. Ben-Porath I, Thomson M W, Carey V J, Ge R, Bell G W, et al. (2008) An embryonic stem cell-like gene expression signature in poorly differentiated aggressive human tumors. Nat Genet. 40: 499-507.
51. Gao J X (2008) Cancer stem cells: the lessons from pre-cancerous stem cells. J Cell Mol Med 12: 67-96.
52. Grill J, Dufour C, Kalifa C (2006) High-dose chemotherapy in children with newly-diagnosed medulloblastoma. Lancet Oncol 7: 787-789.
53. Grill J, Sainte-Rose C, Jouvet A, Gentet J C, Lejars O, et al. (2005) Treatment of medulloblastoma with postoperative chemotherapy alone: an SFOP prospective trial in young children. Lancet Oncol 6: 573-580.
54. Zimmermann T S, Lee A C, Akinc A, Bramlage B, Bumcrot D, et al, (2006) RNAi-mediated gene silencing in non-human primates. Nature 441: 111-114.

SUPPORTING INFORMATION REFERENCES

1. Friedman H S, Burger P C, Bigner S H, Trojanowski J Q, Wikstrand C J, et al. (1985) Establishment and characterization of the human medulloblastoma cell line and transplantable xenograft D283 Med. J Neuropathol Exp Neurol 44: 592-605.
2. Jacobsen P F, Jenkyn D J, Papadimitriou J M (1985) Establishment of a human medulloblastoma cell line and its heterotransplantation into nude mice. J Neuropathol Exp Neurol 44: 472-485.
3. Kim S, Lee U J, Kim M N, Lee E J, Kim J Y, et al. (2008) MicroRNA miR-199a* regulates the MET proto-oncogene and the downstream extracellular signal-regulated kinase 2 (ERK2). J Biot Chem 283: 18158-18166.
4. Kertesz. M, Iovino N, Unnerstall U, Gaul U, Segal E (2007) The role of site accessibility in microRNA target recognition. Nat Genet 39: 1278-1284.
5. Rubin J B, Kung A L, Klein R S, Chan J A, Sun Y, et al. (2003) A small-molecule antagonist of CXCR4 inhibits intracranial growth of primary brain tumors. Proc Natl Acad Sci USA 100: 13513-13518.
6. Fan X, Matsui W, Khaki L, Stearns D, Chun J, et al. (2006) Notch pathway inhibition depletes stem-like cells and blocks engraftment in embryonal brain tumors. Cancer Res 66: 7445-7452.
7. Dovey H F, John V, Anderson J P, Chen L Z, de Saint Andrieu P, et al. (2001) Functional gamma-secretase inhibitors reduce beta-amyloid peptide levels in brain. J Neurochem 76: 173-181.
8. Geling A, Steiner H, Willem M, Bally-Cuif L, Haass C (2002) A gamma-secretase inhibitor blocks Notch signaling in vivo and causes a severe neurogenic phenotype in zebrafish. EMBO Rep 3: 688-694.
9. Ben-Porath I, Thomson M W, Carey V J, Ge R, Bell G W, et al, (2008) An embryonic stem cell-like gene expression signature in poorly differentiated aggressive human tumors. Nat Genet. 40: 499-507.
10. MacDonald T J, Brown K M, LaFleur B, Peterson K, Lawlor C, et al. (2001) Expression profiling of medulloblastoma: PDGFRA and the RAS/MAPK pathway as therapeutic targets for metastatic disease. Nat Genet. 29: 143-152.
11. Gilbertson R J, Clifford S C (2003) PDGFRB is overexpressed in metastatic medulloblastoma. Nat Genet. 35: 197-198.
12. Ferretti E, De Smaele E, Po A, Di Marcotullio L, Tosi E, et al. (2008) MicroRNA profiling in human medulloblastoma. Int J Cancer 124: 568-577.
13. Gilbertson R J, Pearson A D, Perry R H, Jaros E. Kelly P J (1995) Prognostic significance of the c-erbB-2 oncogene product in childhood medulloblastoma. Br J Cancer 71: 473-477.
14. Giangaspero F, Wellek S, Masuoka J, Gessi M, Kleihues P, et al. (2006) Stratification of medulloblastoma on the basis of histopathological grading. Acta Neuropathol 112: 5-12.

The invention claimed is:
1. A diagnostic kit in vitro for assessing a histopathological stage of tumour and presence of metastases, wherein the assessing is performed by detecting in a biological sample expression of a sequence comprising SEQ ID NO: 1 through PCR Real-time and detecting one or more genes express in cancer stem cells chosen among CD133, c-myc, Nanog, Oct4, TCFL1, ZIC1, KLF5, HMGA1, HMGB3, wherein the kit comprises:
a) a pair of amplification primers for detecting the sequence comprising SEQ ID NO:1, including:

```
primer Forward:
                                    (SEQ ID NO: 3)
CGGGAATTCCCAGAGGACACCTCCAC; and primer Reverse:
                                    (SEQ ID NO: 4)
CGGCTCGAGCCGAGGGTCTAACCCAG
``` b) a pair of control primers for normalizing an expression value of the sequence comprising SEQ ID NO: 1;
c) one or more of a pair of primers together with a probe for detecting the one or more genes, including:

```
cd133:
primer Forward:
                                    (SEQ ID NO: 49)
TCCACAGAAATTTACCTACATTGGAA;

primer Reverse:
                                    (SEQ ID NO: 50)
GGGTCAGCAGAGAGCAGATGA; and probe:
                                    (SEQ ID NO: 51)
AGTATGATTCATACTGGTGGCTGGGTGGC cmyc:
primer forward:
                                    (SEQ ID NO: 52)
GCTGGATTTTTTTCGGGTAGTG;

primer reverse:
                                    (SEQ ID NO: 53)
TAGTTCCTGTTGGTGAAGCTAACG; and probe
                                    (SEQ ID NO: 54)
CAGCAGCCTCCCGCGACG nanog:
primer forward:
                                    (SEQ ID NO: 55)
CCGAAGAATAGCAATGGTGTGA;

primer reverse:
                                    (SEQ ID NO: 56)
GCATCCCTGGTGGTAGGAAGA; and probe:
                                    (SEQ ID NO: 57)
CAGCACCTACCTACCCCAGCCTTTA oct 4:
primer forward:
                                    (SEQ ID NO: 58)
AACCCGGAGGAGGTAGTCCTT;

primer reverse:
                                    (SEQ ID NO: 59)
AATAACCTACCCACAAATGTCATTCA; and probe:
                                    (SEQ ID NO: 60)
CATGCATGAGTCAGTGAACAGGGAA tcfl1:
primer forward:
                                    (SEQ ID NO: 61)
CCAAGGAAGAGAACGTTGACATAG;

primer reverse:
                                    (SEQ ID NO: 62)
CCGAGGGAGCAGGATCAAG; and probe:
                                    (SEQ ID NO: 63)
AGGCTCTTTGTGTTTTTCCTTGTCTTTTGTCC zic 1:
primer forward:
                                    (SEQ ID NO: 64)
CGCGCTCCGAGAATTTAAAG;

primer reverse:
                                    (SEQ ID NO: 65)
CGGTCACAGCCCTCAAACTC; and probe:
                                    (SEQ ID NO: 66)
TCCACAAAAGGACGCACACAGGG KLF5:
Primer forward:
                                    (SEQ ID NO: 67)
TTTAACCCCACCTCCATCCTATG;

Primer reverse:
                                    (SEQ ID NO: 68)
GGCAGGGTGGTGGGTAAATT; and probe:
                                    (SEQ ID NO: 69)
TGCTTCTAAACTGGCAATTCACAATC HMGA1:
Primer forward:
                                    (SEQ ID NO: 70)
CCCCAGGCAGACCTTATATGAG;
Primer reverse:
                                    (SEQ ID NO: 71)
TGCTTGAGGTCAGGAGTTCGA; and probe:
                                    (SEQ ID NO: 72)
CATGGGAGTCCCACCGTATTGTCCA; and
and HMGB3:
primer forward:
                                    (SEQ ID NO: 73)
CGCTATGATCGGGAAATGAAG;

primer reverse:
                                    (SEQ ID NO: 74)
TGGCCTTTTGGGAGCATTAG; and probe:
                                    (SEQ ID NO: 75)
ATTATGGACCAGCTAAGGGAGGCAAG;
and
``` d) a pair of primers and a probe for normalizing an expression value of the genes in c), including:

```
primer Forward:
                                    (SEQ ID NO: 81)
GCCAACCGCGAGAAGATG;

primer Reverse:
                                    (SEQ ID NO: 82)
ACAGCCTGGATAGCAACGTACA; and
```

-continued
```
probe:
                                         (SEQ ID NO: 83)
CCCAATCATGTTTGAGACCTTCAAC.
```

2. The kit according to claim 1 wherein the pair of control primers in b) for normalizing the expression of the sequence comprising SEQ ID NO: 1 is:

```
                                         (SEQ ID NO: 5)
primer Forward: GAA AAG CCT TGT TTG TGC TTG C;
and (SEQ ID NO: 6)
primer Reverse: GGG CCA TGC TAA TCT TCT CTG T.
```

3. A diagnostic kit in vitro for assessing a histopathological stage of tumour and presence of metastases, wherein the assessing is performed by detecting, in a biological sample through Taqman PCR Real-time, expression of a sequence comprising SEQ ID NO:1 and one or more genes expressed in cancer stem cells chosen among CD133, c-myc, Nanog, Oct4, TCFL1, ZIC1, KLF5, HMGA1, HMGB3, wherein the kit comprises:

a1) a pair of primers and a probe for detecting the expression of the sequence comprising SEQ ID NO: 1, including:

```
    primer Forward:
                                         (SEQ ID NO: 7)
    AGGACACCTCCACTCCGTCTAC;

primer reverse:
                                         (SEQ ID NO: 8)
    GCCTAACCAATGTGCAGACTACTG; and probe:
                                         (SEQ ID NO: 9)
    CAGTGTTTAGACTATCTGTTCAGGACTCCCAAATTG
``` b1) one or more of a pair of primers together with related probes for detecting the expression of the one or more genes, including:

```
    cd133:
    primer Forward:
                                         (SEQ ID NO: 49)
    TCCACAGAAATTTACCTACATTGGAA;

primer Reverse:
                                         (SEQ ID NO: 50)
    GGGTCAGCAGAGAGCAGATGA; and probe:
                                         (SEQ ID NO: 51)
    AGTATGATTCATACTGGTGGCTGGGTGGC c myc:
    primer forward:
                                         (SEQ ID NO: 52)
    GCTGGATTTTTTTCGGGTAGTG;

primer reverse:
                                         (SEQ ID NO: 53)
    TAGTTCCTGTTGGTGAAGCTAACG; and probe
                                         (SEQ ID NO: 54)
    CAGCAGCCTCCCGCGACG nanog:
    primer forward:
                                         (SEQ ID NO: 55)
    CCGAAGAATAGCAATGGTGTGA;

primer reverse:
                                         (SEQ ID NO: 56)
    GCATCCCTGGTGGTAGGAAGA; and probe:
                                         (SEQ ID NO: 57)
    CAGCACCTACCTACCCCAGCCTTTA oct 4:
    primer forward:
                                         (SEQ ID NO: 58)
    AACCCGGAGGAGGTAGTCCTT;

primer reverse:
                                         (SEQ ID NO: 59)
    AATAACCTACCCACAAATGTCATTCA; and probe:
                                         (SEQ ID NO: 60)
    CATGCATGAGTCAGTGAACAGGGAA tcfl1:
    primer forward:
                                         (SEQ ID NO: 61)
    CCAAGGAAGAGAACGTTGACATAG;

primer reverse:
                                         (SEQ ID NO: 62)
    CCGAGGGAGCAGGATCAAG; and probe:
                                         (SEQ ID NO: 63)
    AGGCTCTTTGTGTTTTTCCTTGTCTTTTGTCC zic 1:
    primer forward:
                                         (SEQ ID NO: 64)
    CGCGCTCCGAGAATTTAAAG;

primer reverse:
                                         (SEQ ID NO: 65)
    CGGTCACAGCCCTCAAACTC; and probe:
                                         (SEQ ID NO: 66)
    TCCACAAAAGGACGCACACAGGG KLF5:
    Primer forward:
                                         (SEQ ID NO: 67)
    TTTAACCCCACCTCCATCCTATG;

Primer reverse:
                                         (SEQ ID NO: 68)
    GGCAGGGTGGTGGGTAAATT; and probe:
                                         (SEQ ID NO: 69)
    TGCTTCTAAACTGGCAATTCACAATC HMGA1:
    Primer forward:
                                         (SEQ ID NO: 70)
    CCCCAGGCAGACCTTATATGAG;

Primer reverse:
                                         (SEQ ID NO: 71)
    TGCTTGAGGTCAGGAGTTCGA; and probe:
                                         (SEQ ID NO: 72)
    CATGGGAGTCCCACCGTATTGTCCA HMGB3:
    primer forward:
                                         (SEQ ID NO: 73)
    CGCTATGATCGGGAAATGAAG;

primer reverse:
                                         (SEQ ID NO: 74)
    TGGCCTTTTGGGAGCATTAG; and
```

-continued

```
probe:
                                     (SEQ ID NO: 75)
ATTATGGACCAGCTAAGGGAGGCAAG;
and
``` c1) a pair of primers and a probe for normalizing an expression value of the one or more genes, including:

```
primer forward:
                                     (SEQ ID NO: 81)
GCCAACCGCGAGAAGATG;

primer reverse:
                                     (SEQ ID NO: 82)
ACAGCCTGGATAGCAACGTACA; and probe:
                                     (SEQ ID NO: 83)
CCCAATCATGTTTGAGACCTTCAAC.
``` wherein the probe of a1) or of c1) or one or more of the probes of b1) comprise TaqMan PCR Real-time assay compatible labelled probes.

4. A diagnostic kit in vitro for assessing a histopathological stage of tumour and presence of metastases, wherein the assessing is performed by detecting, in a biological sample through Taqman PCR Real-time, expression of a sequence comprising SEQ ID NO:1 and one or more genes expressed in cancer stem cells chosen among CD133, c-myc, Nanog, Oct4, TCFL1, ZIC1, KLF5, HMGA1, HMGB3, wherein the kit comprises:

a3) a pair of primers and a probe for detecting the expression of the sequence comprising SEQ ID NO: 1, including:

```
primer Forward:
                                     (SEQ ID NO: 7)
AGGACACCTCCACTCCGTCTAC;

primer reverse:
                                     (SEQ ID NO: 8)
GCCTAACCAATGTGCAGACTACTG;
and probe:
                                     (SEQ ID NO: 9)
CAGTGTTTAGACTATCTGTTCAGGACTCCCAAATTG probe:
                                     (SEQ ID NO: 66)
TCCACAAAAGGACGCACACAGGG
``` b3) one or more of a pair of primers together with related probes for detecting the expression of the one or more genes, including:

```
cd133:
primer Forward:
                                     (SEQ ID NO: 49)
TCCACAGAAATTTACCTACATTGGAA, primer Reverse:
                                     (SEQ ID NO: 50)
GGGTCAGCAGAGAGCAGATGA, probe:
                                     (SEQ ID NO: 51)
AGTATGATTCATACTGGTGGCTGGGTGGC, c myc:
primer forward:
                                     (SEQ ID NO: 52)
GCTGGATTTTTTTCGGGTAGTG, primer reverse:
                                     (SEQ ID NO: 53)
TAGTTCCTGTTGGTGAAGCTAACG, probe
                                     (SEQ ID NO: 54)
CAGCAGCCTCCCGCGACG, nanog:
primer forward:
                                     (SEQ ID NO: 55)
CCGAAGAATAGCAATGGTGTGA, primer reverse:
                                     (SEQ ID NO: 56)
GCATCCCTGGTGGTAGGAAGA, probe:
                                     (SEQ ID NO: 57)
CAGCACCTACCTACCCCAGCCTTTA oct 4:
primer forward:
                                     (SEQ ID NO: 58)
AACCCGGAGGAGGTAGTCCTT, primer reverse:
                                     (SEQ ID NO: 59)
AATAACCTACCCACAAATGTCATTCA, probe:
                                     (SEQ ID NO: 60)
CATGCATGAGTCAGTGAACAGGGAA, tcfl1:
primer forward:
                                     (SEQ ID NO: 61)
CCAAGGAAGAGAACGTTGACATAG, primer reverse:
                                     (SEQ ID NO: 62)
CCGAGGGAGCAGGATCAAG, probe:
                                     (SEQ ID NO: 63)
AGGCTCTTTGTGTTTTTCCTTGTCTTTTGTCC, zic 1:
primer forward:
                                     (SEQ ID NO: 64)
CGCGCTCCGAGAATTTAAAG, primer reverse:
                                     (SEQ ID NO: 65)
CGGTCACAGCCCTCAAACTC, probe:
                                     (SEQ ID NO: 66)
TCCACAAAAGGACGCACACAGGG, KLF5:
Primer forward:
                                     (SEQ ID NO: 67)
TTTAACCCCACCTCCATCCTATG, Primer reverse:
                                     (SEQ ID NO: 68)
GGCAGGGTGGTGGGTAAATT, probe:
                                     (SEQ ID NO: 69)
TGCTTCTAAACTGGCAATTCACAATC, HMGA1:
Primer forward:
                                     (SEQ ID NO: 70)
CCCCAGGCAGACCTTATATGAG,
```

-continued
Primer reverse:
TGCTTGAGGTCAGGAGTTCGA, (SEQ ID NO: 71)

probe:
CATGGGAGTCCCACCGTATTGTCCA (SEQ ID NO: 72)
and

HMGB3:
primer forward:
CGCTATGATCGGGAAATGAAG, (SEQ ID NO: 73)

primer reverse:
TGGCCTTTTGGGAGCATTAG, (SEQ ID NO: 74)

probe:
ATTATGGACCAGCTAAGGGAGGCAAG; (SEQ ID NO: 75)
and wherein one or more of the probes of one or more of a3), b3), and c3) comprise a detectable label selected from the group comprising fluorophores and quenchers.

5. A diagnostic kit in vitro for assessing a histopathological stage of tumour and presence of metastases, wherein the assessing is performed by detecting, in a biological sample through Taqman PCR Real-time, expression of a sequence comprising SEQ ID NO:1 and one or more genes expressed in cancer stem cells chosen among CD133, c-myc, Nanog, Oct4, TCFL1, ZIC1, KLF5, HMGA1, HMGB3,
wherein the kit comprises:
  a4) a pair of primers and a probe for detecting the expression of the sequence comprising SEQ ID NO: 1, including:

primer Forward:
AGGACACCTCCACTCCGTCTAC; (SEQ ID NO: 7)

primer reverse:
GCCTAACCAATGTGCAGACTACTG; and (SEQ ID NO: 8)

probe:
CAGTGTTTAGACTATCTGTTCAGGACTCCCAAATTG (SEQ ID NO: 9)

b4) a pair of primers and a probe for detecting the expression of the zic1 gene, including:

primer forward:
CGCGCTCCGAGAATTTAAAG; (SEQ ID NO: 64)

primer reverse:
CGGTCACAGCCCTCAAACTC; (SEQ ID NO: 65)
and probe:
TCCACAAAAGGACGCACACAGGG (SEQ ID NO: 66)

c4) one or more of a pair of primers together with related probes for detecting the expression of the one or more genes, including:

cd133
primer Forward:
TCCACAGAAATTTACCTACATTGGAA; (SEQ ID NO: 49)

-continued
primer Reverse:
GGGTCAGCAGAGAGCAGATGA; (SEQ ID NO: 50)
and probe:
AGTATGATTCATACTGGTGGCTGGGTGGC (SEQ ID NO: 51)

c myc:
primer forward:
GCTGGATTTTTTCGGGTAGTG; (SEQ ID NO: 52)

primer reverse:
TAGTTCCTGTTGGTGAAGCTAACG; (SEQ ID NO: 53)
and probe
CAGCAGCCTCCCGCGACG (SEQ ID NO: 54)

nanog:
primer forward:
CCGAAGAATAGCAATGGTGTGA; (SEQ ID NO: 55)

primer reverse:
GCATCCCTGGTGGTAGGAAGA; (SEQ ID NO: 56)
and probe:
CAGCACCTACCTACCCCAGCCTTTA (SEQ ID NO: 57)

oct 4:
primer forward:
AACCCGGAGGAGGTAGTCCTT; (SEQ ID NO: 58)

primer reverse:
AATAACCTACCCACAAATGTCATTCA; (SEQ ID NO: 59)
and probe:
CATGCATGAGTCAGTGAACAGGGAA (SEQ ID NO: 60)

tcfl1:
primer forward:
CCAAGGAAGAGAACGTTGACATAG; (SEQ ID NO: 61)

primer reverse:
CCGAGGGAGCAGGATCAAG; (SEQ ID NO: 62)
and probe:
AGGCTCTTTGTGTTTTTCCTTGTCTTTTGTCC (SEQ ID NO: 63)

KLF5:
Primer forward:
TTTAACCCCACCTCCATCCTATG; (SEQ ID NO: 67)

Primer reverse:
GGCAGGGTGGTGGGTAAATT; (SEQ ID NO: 68)
and probe:
TGCTTCTAAACTGGCAATTCACAATC (SEQ ID NO: 69)

```
-continued
HMGA1:
Primer forward:
                                             (SEQ ID NO: 70)
CCCCAGGCAGACCTTATATGAG;

Primer reverse:
                                             (SEQ ID NO: 71)
TGCTTGAGGTCAGGAGTTCGA;
and probe:
                                             (SEQ ID NO: 72)
CATGGGAGTCCCACCGTATTGTCCA HMGB3:
primer forward:
                                             (SEQ ID NO: 73)
CGCTATGATCGGGAAATGAAG;

primer reverse:
                                             (SEQ ID NO: 74)
TGGCCTTTTGGGAGCATTAG;
and probe:
                                             (SEQ ID NO: 75)
ATTATGGACCAGCTAAGGGAGGCAAG;
and
``` d4) a pair of primers and a probe for normalizing an expression value of the one or more genes including:

```
primer forward:
                                             (SEQ ID NO: 81)
GCCAACCGCGAGAAGATG;

primer reverse:
                                             (SEQ ID NO: 82)
ACAGCCTGGATAGCAACGTACA;
and probe:
                                             (SEQ ID NO: 83)
CCCAATCATGTTTGAGACCTTCAAC.
```

6. A diagnostic kit in vitro for assessing a histopathological stage of tumour and presence of metastases, wherein the assessing is performed by detecting, in a biological sample through Taqman PCR Real-time, expression of a sequence comprising SEQ ID NO: 1 and one or more genes expressed in cancer stem cells chosen among CD133, c-myc, Nanog, Oct4, TCFL1, ZIC1, KLF5, HMGA1, HMGB3, wherein the kit comprises:

a5) a pair of primers and a probe for detecting the expression of the sequence comprising SEQ ID NO: 1, including:

```
primer Forward:
                                             (SEQ ID NO: 7)
AGGACACCTCCACTCCGTCTAC;

primer reverse:
                                             (SEQ ID NO: 8)
GCCTAACCAATGTGCAGACTACTG;
and probe:
                                             (SEQ ID NO: 9)
CAGTGTTTAGACTATCTGTTCAGGACTCCCAAATTG
``` b5) a pair of primers and a probe for detecting the expression of the tcfl1 gene, including:

```
primer forward:
                                             (SEQ ID NO: 61)
CCAAGGAAGAGAACGTTGACATAG;

primer reverse:
                                             (SEQ ID NO: 62)
CCGAGGGAGCAGGATCAAG;
and probe:
                                             (SEQ ID NO: 63)
AGGCTCTTTGTGTTTTTCCTTGTCTTTTGTCC
``` c5) one or more of a pair of primers together with related probes for detecting the expression of the one or more genes, including:

```
cd133
primer Forward:
                                             (SEQ ID NO: 49)
TCCACAGAAATTTACCTACATTGGAA;

primer Reverse:
                                             (SEQ ID NO: 50)
GGGTCAGCAGAGAGCAGATGA;
and probe:
                                             (SEQ ID NO: 51)
AGTATGATTCATACTGGTGGCTGGGTGGC c myc:
primer forward:
                                             (SEQ ID NO: 52)
GCTGGATTTTTTTCGGGTAGTG;

primer reverse:
                                             (SEQ ID NO: 53)
TAGTTCCTGTTGGTGAAGCTAACG;
and probe
                                             (SEQ ID NO: 54)
CAGCAGCCTCCCGCGACG nanog:
primer forward:
                                             (SEQ ID NO: 55)
CCGAAGAATAGCAATGGTGTGA;

primer reverse:
                                             (SEQ ID NO: 56)
GCATCCCTGGTGGTAGGAAGA;
and probe:
                                             (SEQ ID NO: 57)
CAGCACCTACCTACCCCAGCCTTTA oct 4:
primer forward:
                                             (SEQ ID NO: 58)
AACCCGGAGGAGGTAGTCCTT;

primer reverse:
                                             (SEQ ID NO: 59)
AATAACCTACCCACAAATGTCATTCA;
and probe:
                                             (SEQ ID NO: 60)
CATGCATGAGTCAGTGAACAGGGAA
```

95

-continued zic 1:
primer forward:
(SEQ ID NO: 64)
CGCGCTCCGAGAATTTAAAG;

primer reverse:
(SEQ ID NO: 65)
CGGTCACAGCCCTCAAACTC;
and probe:
(SEQ ID NO: 66)
TCCACAAAAGGACGCACACAGGG KLF5:
Primer forward:
(SEQ ID NO: 67)
TTTAACCCCACCTCCATCCTATG;

Primer reverse:
(SEQ ID NO: 68)
GGCAGGGTGGTGGGTAAATT;
and probe:
(SEQ ID NO: 69)
TGCTTCTAAACTGGCAATTCACAATC HMGA1:
Primer forward:
(SEQ ID NO: 70)
CCCCAGGCAGACCTTATATGAG;

Primer reverse:
(SEQ ID NO: 71)
TGCTTGAGGTCAGGAGTTCGA;
and probe:
(SEQ ID NO: 72)
CATGGGAGTCCCACCGTATTGTCCA HMGB3:
primer forward:
(SEQ ID NO: 73)
CGCTATGATCGGGAAATGAAG;

primer reverse:
(SEQ ID NO: 74)
TGGCCTTTTGGGAGCATTAG;
and probe:
(SEQ ID NO: 75)
ATTATGGACCAGCTAAGGGAGGCAAG;
and d5) a pair of primers and a probe for normalizing an expression value of th one or more genes, including:

primer forward:
(SEQ ID NO: 81)
GCCAACCGCGAGAAGATG;

primer reverse:
(SEQ ID NO: 82)
ACAGCCTGGATAGCAACGTACA;
and probe:
(SEQ ID NO: 83)
CCCAATCATGTTTGAGACCTTCAAC.

7. A diagnostic method in vitro for evaluating a histopathological stage of tumour and presence of metastases, the method comprising:

96 detecting in a biological sample expression of a sequence comprising SEQ ID NO:1, and detecting expression of one or more genes expressed in the cancer stem cells chosen among CD133, c-myc, nanog, oct4, TCFL1, ZIC1, KLF5, HMGA1, HMGB3;

wherein detecting expression of the sequence comprising SEQ ID NO:1 is performed by amplifying the sequence comprising SEQ ID NO: 1 by PCR Real Time using a pair of amplification primers including:

primer Forward:
(SEQ ID NO: 3)
CGGGAATTCCCAGAGGACACCTCCAC, primer Reverse:
(SEQ ID NO: 4)
CGGCTCGAGCCGAGGGTCTAACCCAG;

and a pair of control primers for normalizing an expression value of the sequence comprising SEQ ID NO: 1.

8. The method according to claim 7, wherein the control primers for normalizing the expression value of the sequence comprising SEQ ID NO: 1 include:

primer Forward:
(SEQ ID NO: 5)
GAA AAG CCT TGT TTG TGC TTG C; and primer Reverse:
(SEQ ID NO: 6)
GGG CCA TGC TAA TCT TCT CTG T.

9. The method according to claim 7 wherein detecting expression of the sequence comprising SEQ ID NO: 1 is performed by the following steps:
retrotranscribing RNA; and
expressing the sequence comprising SEQ ID NO: 1 by TaqMan assay using a pair of primers and a probe sequence including:

primer Forward:
(SEQ ID NO: 7)
AGGACACCTCCACTCCGTCTAC;

primer reverse:
(SEQ ID NO: 8)
GCCTAACCAATGTGCAGACTACTG;
and probe:
(SEQ ID NO: 9)
CAGTGTTTAGACTATCTGTTCAGGACTCCCAAATTG.

10. The method according to claim 7, wherein detecting expression of the one or more genes is performed by:
amplifying at least one sequence through PCR real time using a pair of amplification primers and a pair of control primers for normalizing an expression value of the at least one sequence,
wherein the at least one sequence is selected from the group consisting of:

CD133:
(SEQ ID NO: 13)
CTATGTGGTACAGCCGCGTGATTTCCCAGAAGATACTTTGAGAAAATTC
TTACAGAAGGCATATGAATCCAA AATTGATTA c-myc:
(SEQ ID NO: 14)
AGGAGGAACAAGAAGATGAGGAAGAAATCGATGTT -continued
```
Nanog:
                                         (SEQ ID NO: 15)
GCAAATGTCTTCTGCTGAGATGCCTCACACGGAGACTGTCTCTCCTCTT
CCTTCCTCCATGGATCTGCTTATTCAGGACAGC Oct4:
                                         (SEQ ID NO: 16)
ACTGCAGCAGATCAGCCACATCGCCCAGCAGCTTGGGCTCGAGAAGGAT
GTGGTCCGAGTGTGGTTCTGTAACCGGCGCCA TCFL1:
                                         (SEQ ID NO: 17)
CCGCGGGACTATTTCGCCGAAGTGAGAAGGCCTCAGGACAGCGCGTTC
TTT ZIC1:
                                         (SEQ ID NO: 18)
CAGTTCGCTGCGCAAACACATGAAGGTCCACGAATCCTCCTCGCAGGGC
TC KLF5:
                                         (SEQ ID NO: 19)
GCATCCACTACTGCGATTACCCTGGTTGCACAAAAGTTTATACCAAGTCT
TCTCA HMGA1:
                                         (SEQ ID NO: 20)
AAAAACAAGGGTGCTGCCAAGACCCGGAAAACCACCACAACTCCAGG
AAGG
and HMGB3:
                                         (SEQ ID NO: 21)
TTTTCCAAGAAGTGCTCTGAGAGGTGGAAGACGATGTCCGGGAAAGA
GAAA;
``` wherein the pair of amplification primers is selected from the group consisting of:

```
    CD133:
    Primer Forward:
                                         (SEQ ID NO: 22)
    CTATGTGGTACAGCCGCGTG, Primer Reverse:
                                         (SEQ ID NO: 23)
    TAATCAATTTTGGATTCATATGCCTTC c-myc:
    primer Forward:
                                         (SEQ ID NO: 24)
    ATGAGGAGACACCGCCCAC, primer Reverse:
                                         (SEQ ID NO: 25)
    AACATCGATTTCTTCCTCATCTTCTT Nanog:
    primer Forward:
                                         (SEQ ID NO: 26)
    GCAAATGTCTTCTGCTGAGATGC, primer Reverse:
                                         (SEQ ID NO: 27)
    GCTGTCCTGAATAAGCAGATCCAT Oct4:
    primer Forward:
                                         (SEQ ID NO: 28)
    ACTGCAGCAGATCAGCCACA, primer Reverse:
                                         (SEQ ID NO: 29)
    TGGCGCCGGTTACAGAAC TCFL1:
    primer Forward:
                                         (SEQ ID NO: 30)
    CCGCGGGACTATTTCGC, primer Reverse:
                                         (SEQ ID NO: 31)
    AAAGAACGCGCTGTCCTGAG ZIC1:
    primer Forward:
                                         (SEQ ID NO: 32)
    CAGTTCGCTGCGCAAACA, primer Reverse:
                                         (SEQ ID NO: 33)
    GAGCCCTGCGAGGAGGAT KLF5:
    primer Forward:
                                         (SEQ ID NO: 34)
    GCATCCACTACTGCGATTACCC, primer Reverse:
                                         (SEQ ID NO: 35)
    TGAGAAGACTTGGTATAAACTTTTGTGC HMGA1:
    primer Forward:
                                         (SEQ ID NO: 36)
    AAAAACAAGGGTGCTGCCAA, primer Reverse:
                                         (SEQ ID NO: 37)
    CCTTCCTGGAGTTGTGGTGGT;
    and HMGB3:
    primer Forward:
                                         (SEQ ID NO: 38)
    TTTTCCAAGAAGTGCTCTGAGAGG, primer Reverse:
                                         (SEQ ID NO: 39)
    TTTCTCTTTCCCGGACATCG
    and
``` wherein the pair of control primers are:

```
    primer forward:
                                         (SEQ ID NO: 79)
    CGT GCT GCT GAC CGA GG,
    and primer reverse:
                                         (SEQ ID NO: 80)
    GAA GGT CTC AAA CAT GAT CTG GGT.
```

11. The method according to claim 7, wherein detecting expression of the one or more genes is performed by:

amplifying at least one sequence through real time TaqMan assay using a pair of primers and a probe for the amplifying the at least one sequence, and a pair of control primers and a control probe for normalizing an expression value of the at least one sequence, wherein the at least one sequence is selected from the group consisting of:

```
cd133:
                                         (SEQ ID NO: 40)
TCCACAGAAATTTACCTACATTGGAAGAGTATGATTCATACTGGTGGCTG
GGTGGCCTGGTCATCTGCTCTCTGCTGACCC cmyc:
                                         (SEQ ID NO: 41)
GCTGGATTTTTTTCGGGTAGTGGAAAACCAGCAGCCTCCCGCGACGATG
CCCCTCAACGTTAGCTTCACCAACAGGAACTA
```

-continued nanog:
(SEQ ID NO: 42)
CCGAAGAATAGCAATGGTGTGACGCAGAAGGCCTCAGCACCTACCTAC
CCCAGCCTTTACTCTTCCTACCACCAGGGATG oct4:
(SEQ ID NO: 43)
AACCCGGAGGAGGTAGTCCTTTGTTACATGCATGAGTCAGTGAACAGGGA
ATGGGTGAATGACATTTGTGGGTAGGTTATT tcfl1:
(SEQ ID NO: 44)
CCAAGGAAGAGAACGTTGACATAGAAGGCTCTTTGTGTTTTTCCTTGTCT
TTTGTCCTCAGACTTGATCCTGCTCCCTCGG zic1:
(SEQ ID NO: 45)
CGCGCTCCGAGAATTTAAAGATCCACAAAAGGACGCACACAGGGAGAAGC
CCTTCAAGTGCGAGTTTGAGGGCTGTGACC KLF5:
(SEQ ID NO: 46)
TTTAACCCCACCTCCATCCTATGCTGCTACAATTGCTTCTAAACTGGCAA
TTCACAATCCAAATTTACCCACCACCCTGCC HMGA1:
(SEQ ID NO: 47)
CCCCAGGCAGACCTTATATGAGACATGGGAGTCCCACCGTATTGTCCA
GGCTGGTCTCGAACTCCTGACCTCAAGCA
and HMGB3:
(SEQ ID NO: 48)
CGCTATGATCGGGAAATGAAGGATTATGGACCAGCTAAGGGAGGCAA
GAAGAAGAAGGATCCTAATGCTCCCAAAAGGCCA;

wherein the pair of primers and the probe for amplifying the at least one sequence are selected from the group consisting of:

cd133:
primer Forward:
(SEQ ID NO: 49)
TCCACAGAAATTTACCTACATTGGAA, primer Reverse:
(SEQ ID NO: 50)
GGGTCAGCAGAGAGCAGATGA, probe:
(SEQ ID NO: 51)
AGTATGATTCATACTGGTGGCTGGGTGGC cmyc:
primer forward:
(SEQ ID NO: 52)
GCTGGATTTTTTTCGGGTAGTG, primer reverse:
(SEQ ID NO: 53)
TAGTTCCTGTTGGTGAAGCTAACG, probe
(SEQ ID NO: 54)
CAGCAGCCTCCCGCGACG, nan-og:
primer forward:
(SEQ ID NO: 55)
CCGAAGAATAGCAATGGTGTGA, primer reverse:
(SEQ ID NO: 56)
GCATCCCTGGTGGTAGGAAGA, probe:
(SEQ ID NO: 57)
CAGCACCTACCTACCCCAGCCTTTA, oct 4:
primer forward:
(SEQ ID NO: 58)
AACCCGGAGGAGGTAGTCCTT, primer reverse:
(SEQ ID NO: 59)
AATAACCTACCCACAAATGTCATTCA, probe:
(SEQ ID NO: 60)
CATGCATGAGTCAGTGAACAGGGAA, tcfl1:
primer forward:
(SEQ ID NO: 61)
CCAAGGAAGAGAACGTTGACATAG, primer reverse:
(SEQ ID NO: 62)
CCGAGGGAGCAGGATCAAG, probe:
(SEQ ID NO: 63)
AGGCTCTTTGTGTTTTTCCTTGTCTTTTGTCC zic 1:
primer forward:
(SEQ ID NO: 64)
CGCGCTCCGAGAATTTAAAG, primer reverse:
(SEQ ID NO: 65)
CGGTCACAGCCCTCAAACTC, probe:
(SEQ ID NO: 66)
TCCACAAAAGGACGCACACAGGG KLF5:
Primer forward:
(SEQ ID NO: 67)
TTTAACCCCACCTCCATCCTATG, Primer reverse:
(SEQ ID NO: 68)
GGCAGGGTGGTGGGTAAATT, probe:
(SEQ ID NO: 69)
TGCTTCTAAACTGGCAATTCACAATC, HMGA1:
Primer forward:
(SEQ ID NO: 70)
CCCCAGGCAGACCTTATATGAG, Primer reverse:
(SEQ ID NO: 71)
TGCTTGAGGTCAGGAGTTCGA, probe:
(SEQ ID NO: 72)
CATGGGAGTCCCACCGTATTGTCCA;
and HMGB3:
primer forward:
(SEQ ID NO: 73)
CGCTATGATCGGGAAATGAAG, primer reverse:
(SEQ ID NO: 74)
TGGCCTTTTGGGAGCATTAG, probe:
(SEQ ID NO: 75)
ATTATGGACCAGCTAAGGGAGGCAAG;
and wherein the pair of control primers and the control probe are:

```
primer Forward:
                                    (SEQ ID NO: 81)
GCCAACCGCGAGAAGATG, primer Reverse:
                                    (SEQ ID NO: 82)
ACAGCCTGGATAGCAACGTACA, probe:
                                    (SEQ ID NO: 83)
CCCAATCATGTTTGAGACCTTCAAC.
```

* * * * *